US010975167B2

(12) United States Patent
Garcia

(10) Patent No.: US 10,975,167 B2
(45) Date of Patent: Apr. 13, 2021

(54) METHOD TO REDUCE PULMONARY ARTERIAL HYPERTENSION BY ADMINISTERING INHIBITORS OF NICOTINAMIDE PHOSPHORIBOTRANSFERASE

(71) Applicant: Arizona Board of Regents on Behalf of the University of Arizona, Tucson, AZ (US)

(72) Inventor: Joe G. N. Garcia, Tucson, AZ (US)

(73) Assignee: Arizona Board of Regents on Behalf of The University of Arizona, Tucson, AZ (US)

(*) Notice: Subject to any disclaimer, the term of this patent is extended or adjusted under 35 U.S.C. 154(b) by 0 days.

(21) Appl. No.: 16/604,517

(22) PCT Filed: Apr. 16, 2018

(86) PCT No.: PCT/US2018/027780
§ 371 (c)(1),
(2) Date: Oct. 10, 2019

(87) PCT Pub. No.: WO2018/191747
PCT Pub. Date: Oct. 18, 2018

(65) Prior Publication Data
US 2020/0148789 A1 May 14, 2020

Related U.S. Application Data

(60) Provisional application No. 62/485,870, filed on Apr. 14, 2017.

(51) Int. Cl.
| | |
|---|---|
| C07K 16/40 | (2006.01) |
| A61K 9/00 | (2006.01) |
| A61K 31/444 | (2006.01) |
| A61K 45/06 | (2006.01) |
| C12N 15/113 | (2010.01) |
| A61K 39/00 | (2006.01) |

(52) U.S. Cl.
CPC ............ C07K 16/40 (2013.01); A61K 9/0053 (2013.01); A61K 31/444 (2013.01); A61K 45/06 (2013.01); C12N 15/113 (2013.01); A61K 2039/505 (2013.01); C07K 2317/54 (2013.01); C07K 2317/55 (2013.01); C07K 2317/76 (2013.01)

(58) Field of Classification Search
CPC .......................... C07K 16/40; C07K 2317/34; C07K 2317/54; C07K 2317/55; C07K 2317/76; A61K 9/0053; A61K 31/444; A61K 45/06; A61K 2039/505; A61K 2039/545; A61K 31/403; A61K 31/4045; A61K 31/4406; A61K 31/453; C12N 15/113; A61P 9/12

See application file for complete search history.

(56) References Cited

U.S. PATENT DOCUMENTS

| | | | |
|---|---|---|---|
| 7,754,703 B2 | 7/2010 | Lynch | |
| 8,329,676 B2 | 12/2012 | Lynch | |
| 9,409,983 B2 | 8/2016 | Garcia | |
| 2008/0249070 A1 | 10/2008 | Lynch | |
| 2009/0042954 A1 | 2/2009 | Hale | |
| 2010/0003242 A1 | 1/2010 | Sabbadini | |
| 2016/0031880 A1 | 2/2016 | Clark | |

FOREIGN PATENT DOCUMENTS

| | | |
|---|---|---|
| WO | 2012118910 | 9/2012 |
| WO | 2014144821 | 9/2014 |
| WO | 2016016898 | 2/2016 |
| WO | 2017031213 | 2/2017 |
| WO | 2017041114 | 3/2017 |

OTHER PUBLICATIONS

Oita, RC, et al. (May 22, 2017) American Journal of Respiratory and Critical Care Medicine 195:A4402. B80-A. Mechanisms and Models of Acute Lung Injury. Thematic Poster Session.*
https://www.novusbio.com/products/pbef-visfatin-nampt-antibody_nb100-594 (retrieved from the internet Jan. 12, 2021).*
https://www.bethyl.com/antibody/pca_a-z/NAMPT+PBEF+Visfatin (retrieved from the internet Jan. 12, 2021).*
Albert, et al., "Novel Immunomodulator FTY720 IS Phosphorylated in Rats and Humans to Form a Single Stereoisomer. Identification, Chemical Proof, and Biological Characterization of the Biologically Active Species and Its Enantiomer", J. Med. Chem., 48:5373-5377 (2005).
Almagro, et al., "Antibody Modeling Assessment", Proteins, 79:3050-3066 (2011).
Anscher, et al., "Plasma transforming growth factor beta1 as a predictor of radiation pneumonitis", Int. J. Radiat. Oncol. Biol. Phys., 41:1029-35 (1998).

(Continued)

*Primary Examiner* — Robert S Landsman
(74) *Attorney, Agent, or Firm* — Pabst Patent Group LLP

(57) ABSTRACT

It has been established that inhibition of the expression and function of nicotinamide phosphoribosyltransferase (NAMPT) can treat Pulmonary Arterial Hypertension (PAH) in a patient in need thereof. Compositions and methods of an effective amount of one or more inhibitors of intracellular NAMPT (iNAMPT), extracellular NAMPT (eNAMPT), or a receptor of eNAMPT, to treat PAH are provided. The compositions and methods reduce, or reverse the physiological vascular changes associated with the onset and progression of PAH. Inhibitors of NAMPT or receptors of NAMPT include small molecules, antibodies and antigen binding fragments thereof. Dosage forms including monoclonal antibody inhibitors of NAMPT or NAMPT receptors in an amount between 10 mg and 400 mg are provided. Dosage forms including small molecule inhibitors of NAMPT in an amount between 10 mg/kg and 3.5 mg/kg body weight of the recipient are also provided.

22 Claims, 12 Drawing Sheets

Specification includes a Sequence Listing.

(56) References Cited

OTHER PUBLICATIONS

Baker, et al., "Identification and Removal of Immunogenicity in Therapeutic Proteins", Curr. Opin. Drug. Discov. Devel., 10:219-227 (2007).

Berdyshev, et al., "De Novo Biosynthesis of Dihydrosphingosine-1-Phophate by Sphingosine Kinase 1 in Mammalian Cells", Cell Signal, 18:1779-92 (2006).

Berdyshev, et al., "Quantitative analysis of Sphingoid base-1-phophates as Bisacetylated derivatives by liquid Chromatography-Tandem Mass Spectrometry", Anal. Biochem., 339:129-36 (2005).

Brigham, et al., "Endotoxin and lung injury", Am. Rev. Respir. Dis., 133:913-27 (1986).

Camp, et al., "Synthetic Analogs of FTY720 [2, Amino-2-[4-octylphenyl]ethyl)-1,3-propanediol] Differentially Regulate Pulmonary Vascular Permeability in Vivo and in Vitro", The Journal of Pharmacology and Experimental Ther., 331(1):54-64 (2009).

Camp, et al., "Unique Toll-Like Receptor 4 Activation by NAMPT/PBEF Induces NFkB signaling and Inflammatory Lung Injury", Scientific Report, 5:13135(2015).

Carruthers, et al., "Total Body Irradiation and Pneumonitis Risk: A Review of Outcomes", British Journal of Cancer, 90:2080-2084 (2004).

Chen, et al., "Nicotinamide Phospphoribosyltransferase Promotes Pulmonary Vascular Remodeling and is a Therapeutic Target in Pulmonary Arterial Hypertension", Circulation, 135(16):1532-1546 (2017).

Chen, et al., "Radiation Pneumonitis and Early Circulatory Cytokine Markers", Semin. Radiat. Oncol., 12:26-33 (2002).

Cho, et al., "Nrf2 Defends the Lung From Oxidative Stress", Antioxid. Redox. Signal, 8:76-87 (2006).

Diab, et al. "Stimulation of Sphingosine 1-Phophate Signaling as an alveolar Cell survival Strategy in Emphysema", Am. J. Respir. Crit. Care Med., 181:344-352 (2010).

Dinkova-Kostova, et al., "Direct and Indirect Antioxidant Properties of Inducers of Cytoprotective Proteins", Mol. Nutr. Food Res., 52 Suppl, 1:S128-138 (2008).

Dudek, et al., "Cytoskeletal Regulation of Pulmonary Vascular Permeability", J. Appl. Physiol., 91(4):1487-1500 (2001).

Dudek, et al., "Pulmonary Endothelial Cell Barrier Enhancement by FTY720 Does Not Require the S1P1 Receptor", Cell Signal, 19:1754-1764 (2007).

Dudek, et al., "Pulmonary Endothelial cell Barrier Enhancement by Sphingosine 1-phosphate: Roles for Cortactin and Myosin light Chain Kinase", J. Biol. Chem., 279:24692-24700 (2004).

Dziarski, et al., "Role of MD-2 in tlr2-And TLR4-mediated Recognition of Gram-negative and Gram-positive bacteria and Activation of Chemokine Genes", J. Endotoxin Res. 6(5):401-5 (2000).

Foncea, et al., "Endothelial Cell Oxidative Stress and Signal Transduction", Biological Research, 33:89-96 (2000).

Forrest, et al., "Immune Cell Regulation and Cardiovascular Effects of Sphingosine 1-Phosphate Receptor Agonists in Rodents Are Mediated Via Distinct Receptor Subtypes", J. Pharmacol. Exp. Ther., 309:758-68 (2004).

Foss, et al., "Synthesis, Stability, and implications of phosphothioate agonists of sphingosine-1-phosphate receptors", Bioorganic & Medicinal Chemistry Letters, 15:4470-4474 (2005).

Garcia, et al., "Sphingosine 1-phosphate Promotes Endothelial Cell Barrier Integrity by Edg-dependent Cytoskeletal Rearrangement", J. Clin. Invest. 108:689-701 (2001).

Garcia, et al., "Thrombin-induced Increase in Albumin Permeability Across the Endothelium", J. Cell Physiol., 128:96-104 (1986).

Georgel, et al., "The Heterogeneous Allelic Repertoire of Human Toll-Like Receptor (TLR) Genes", PLoS One, 4(11): e7803 (2009).

Ghafoori, et al., Radiation-Induced Lung Injury: Assessment, Management, and Prevention, Oncology, 22(1):37-47 (2008).

Ghio, et al., "Pulmonary Arterial Compliance: How and why Should We Measure It?" Glob. Cardiol. Sci. Pract. 2015(4): 58 (2015).

Giaid, et al., "Inducible Nitric Oxide Synthase and Nitrotyrosine in Mice With radiation-Induced Lung Damage", Am. J. Clin. Oncol., 26:e67-72 (2003).

Girgis, et al., "Attenuation of Chronic Hypoxic Pulmonary Hypertension by simvastatin", Am. J. Physiol. Heart Circ. Physiol., 285:H938-945 (2003).

Goggel, et al., "PAF-mediated Pulmonary Edema: A New Role for Acid Sphingomyelinase and Ceramide", Nat. Med., 10:155-60 (2004).

Gon, et al., "S1P3 receptor-Induced Reorganization of Epithelial Tight Junctions Compromises Lung Barrier Integrity and Is Potentiated by TNF", Proc. Natl. Acad. Sci., 102:9270-75 (2005).

Gross, "Experimental radiation Pneumonitis. IV. Leakage of Circulatory Proteins Onto the Alveolar Surface", J. Lab Clin Med., 95:19-31 (1980).

Grynkiewcz, et al., "A New Generation of Ca2+ Indicators with greatly Improved Fluorescence Properties", J. Biol. Chem., 260:3440-3450 (1985).

Hallahan, et al., "Nuclear Factor kappaB Dominant Negative Genetic Constructs Inhibit X-ray Induction of Cell Adhesion molecules in the Vascular Endothelium", Cancer Res., 58:5484-5488 (1998).

Harbeck, et al., "Simultaneous Optical measurements of Cytosolic Ca2+ and cAMP in Single Cells", Sci. STKE, 16 (2006).

Harris, et al., "Identification of Multiple Sources of Charge Heterogeneity in a Recombinant Antibody", J. Chromatogr. B. Biomed. Sci. Appl., 752:233-245 (2001).

Honegger, et al., "The Influence of the Framework Core Residues on the Biophysical Properties of Immunoglobulin Heavy Chain Variable Domains", Protein Eng. Des. Sel., 22:121-134 (2009).

Hong, et al., "Essential Role of pre-B-cell Colony enhancing Factor in Ventilator-Induced Lung Injury", Am J. Respir. Crit. Care Med., 178:605-617 (2008).

Hong, et al., "Rapid Induction of Cytokine Gene Expression in the Lung After Single and Fractionated doses of Radiation", Int. J Radiat. Biol., 75:1421-7 (1999).

International Search Report and Written Opinion for corresponding PCT PCT/US2018/27780 dated Jul. 11, 2018.

International Search Report and Written Opinion for PCT PCT/US2018/27799 dated Jul. 3, 2018.

International Search Report for PCT application PCT/US2011/027074 dated May 24, 2011.

Iwakawa, et al., "Strain Dependent Differences in a Histological Study of CD44 and Collagen Fibers With an Expression Analysis of Inflammatory Response-Related Genes in Irradiated Murine Lung", J. Radiat. Res., 45:423-433 (2004).

Jacobson, et al., "Cytoskeletal Activation and Altered Gene Expression in Endothelial barrier Regulation by Simvastatin", Am. J. Respir. Cell Moo. Biol., 30:662-670 (2004).

Jacobson, et al., "Simvastatin Attenuates Vascular Leak and Inflammation in Murine Inflammatory Lung Injury", Am. J. Physiol. Lung Cell Mol. Physiol., 288:L1026-1032 (2005).

Johnson, et al., "Adjusting Batch Effects in Microarray Expression Data using Empirical Bayes Methods", Biostatistics, 8:118-27 (2007).

Kim, et al., "Crystal structure of visfatin/pre-B Cell colony-Enhancing Factor 1/nicotinamide Phosphoribosyltransferase, Free and in Complex With the anti-Cancer Agent FK-866", J. Mol. Biol., 362:66-77 (2006).

Kovarik, et al., "Overview of FTY720 Clinical Pharmacokinetics and Pharmacology", Ther. Drug. Monit., 26:585-587 (2004).

Koyrakh, et al., "The Heart Rate Decrease Caused by Acute FTY720 Administration is Mediated by the G Protein-Gated Potassium Channel 1", American Journal of Transplantation, 5:529-536 (2005).

Kureishi, et al., "The HMG-CoA Reductase Inhibitor Simvastatin Activate the Protein Kinase Akt and promotes Angiogenesis in Normocholesterolemic Animals", Nat. Med., 6:1004-1010 (2000).

Kwok, et al., "Corticosteroids and Azathioprine Do Not Prevent Radiation-Induced Lung Injury", Can. Respir. J., 5:211-214 (1998).

Li, et al., "Model-base Analysis of Oligonucleotide Arrays: Model Validation, Design Issues and Standard Error Application", Genome Biol., 2:Research0032 (2001).

(56) References Cited

OTHER PUBLICATIONS

Liu, et al., "Sphingosine-1-Phosphate and Its Analogue FTY720 Diminish Acute Pulmonary Injury in Rats With acute Necrotizing Pancreatitis", Pancreas, 36(3)e10-e15 (2008).
Lu, et al., "Radiation-induced Changes in Gene Expression involve Recruitment of existing Messenger RNAS to and Away From Polysomes", Cancer Research, 66:1052-1061 (2006).
Marchesini, et al., "Acid and Neutral Sphingomyelinases: Roles and Mechanisms of Regulation", Biochem. Cell Biol., 82:27-44 (2004).
Mathew, et al., "Simvastin Attenuates Radiation-Induced Murine Lung Injury and Dysregulated Lung Gene Expression", Am. J. Respir. Cell Mol. Biol., ePublicatino only, PMID: 20508068 (2010).
Matloubian, et al., "Lymphocyte Egress from Thymus and Peripheral Lymphoid Organs IS Dependent on S1P Receptor 1", Nature, 427:355-360 (2004).
McVerry, et al., "Sphingosine 1-Phosphate Reduces Vascular Leak in murine and Canine Models of Acute Lung Injury", Am. J. Respir. Crit. Care Med., 170:987-993 (2004).
Meyer, et al., "GADD45a Is a Novel candidate gene in Inflammatory Lung Injury via Influence on Akt Signaling", Faseb. J., 23:1325-1337 (2009).
Moitra, et al., "A Transgenic Mouse With Vascular Endothelial Over-Expression of the Non-Muscle Myosin Light Chain Kinase-2 Isoform Is Susceptible to Inflammatory Lung Injury: Role of Sexual Dimorphism and Age", Trans!. Res., 151:141-153 (2008).
Moitra, et al., "Re-Evaluation of Evans Blue Dye As a Marker of Albumin Clearance in Murine Models of Acute Lung Injury", Trans, Res., 150:253-265 (2007).
Molteni, et al., "Control of Radiation-Induced Pneumopathy and Lung Fibrosis by Angiotensin-Converting Enzyme Inhibitors and an Angiotensin II Type 1 Receptor Blocker", Int. J. Radiat. Biol., 76:523-532 (2000).
Moreno-Vinasco, et al., "Attenuation of Rodent Lung Ischemia-Reperfusion Injury by Sphingosine 1-Phosphate", Journal of Organ Dysfunction, 4:106-114 (2008).
Nonas, et al., "Use of Consomic Rats for Genomic Insights Into Ventilator-Associated Lung Injury", Am. J. Physiol. Lung Cell Mol. Physiol., 293:L92-302 (2007).
North, et al., "A New Clustering of Antibody CDR Loop Conformations", J. Mol. Biol., 406:228-256 (2011).
Ogata, et al., "Early Administration of IL-6RA Does Not Prevent Radiation-Induced Lung Injury in Mice", Radiat. Oncol., 5:26 (2010).
Ostrau, et al., "Lovastatin attenuates ionizing radiation-induced normal tissue damage in vivo", Radiother. Oncol., 92:492-499 (2009).
Peng, et al., "Protective Effects of sphingosine 1-phosphate in Murine Endotoxin-Induced Inflammatory Lung Injury", Am. J. Respir. Crit. Care Med., 169:1245-51 (2004).
Petrache, et al., "Ceramide Upregulation Causes Pulmonary Cell Apoptosis and Emphysema-Like Disease in Mice", Nat Med., 11:491-8 (2005).
Philippe, et al., "Drug-Induced respiratory disease in patients with hematological diseases", Seminars in respiratory and critical care medicine, 26(5):458-81 (2005).
Pollack, et al., "The Importance of Protein Kinase A in Prostate Cancer: Relationship to Patient Outcome in radiation Therapy oncology Group Trial 92-02", Clin, Cancer Res., 15:5478-84 (2009).
Qin, et al., "Differential Regulation of oxidative and Osmotic Stress Induced Syk Activation by Both Autophosphorylation and SH2 Domains", Biochemistry, 37:5481-5486 (1998).
Rabbani, et al., "Hypoxia Inducible Factor 1alpha Signaling in fractionalized radiation-Induced Lung Injury: Role of Oxidative Stress and Tissue Hypoxia", Radiat. Res., 173:165-74 (2010).
Ragaller, et al., "Acute lung injury and acute respiratory distress syndrome", J. Emerg. Trauma Shock., 3(1):43051 (2010).
Remick, et al., "Role of Tumor Necrosis factor-Alpha in Lipopolysaccharide-Induced Pathologic Alterations", Am. J. Pathol., 136:49-60 (1990).

Roberts, et al., "Radiation Pneumonitis: A Possible Lymphocyte-Mediated Hypersensitivity Reaction", Ann. Intern. Med., 118:696-700 (1993).
Rodrigues, et al., "Prediction of Radiation Pneumonitis by Dose-Volume Histogram Parameters in Lung Cancer—a Systematic Review", Radiother. Oncol., 71:127-138 (2004).
Rosendeldt, et al., "Sphingosine-1-phosphate Stimulates Contraction of Human Airway Smooth Muscle Cells", FASEB J., 17:1789-99 (2003).
Roviezzo, et al., "Sphingosine-1-phosphate/sphingosine Kinase Pathway Is Involved in Mouse Airway Hyperresponsiveness", Am. J. Respir. Cell Mol. Biol., 36:757-62 (2007).
Rubin, et al., "A Perpetual Cascade of Cytokines Postirradiation Leads to Pulmonary Fibrosis", Int. J. Radiat. Oncol. Biol. Phys., 33:99-109 (1995).
Sakai, et al., "CD44 and Bak Expression in IL-6 or TNF-alpha Gene Knockout Mice After Whole Lung Irradiation", Journal Radiat. Res., 49:409-416 (2008).
Samal, et al., "Cloning and Characterization of the cDNA Encoding a Novel human pre-B-cell Colony-Enhancing Factor", Mol. Cell. Biol., 14(2):1431-1437 (1994).
Sammani, et al., "Differential Effects pf Sphingosine 1-phosphate Receptors on Airway and Vascular Barrier Function in the Murine Lung", Am. J. Respir. Cell Mol. Biol., 43(4):394-402 (2010).
Sanchez, et al., "Phosphorylation and Action of the Immunomodulator FTY720 Inhibits Vascular Endothelial Cell Growth Factor-induced Vascular Permeability", J. Biol. Chem., 278:4781-47290 (2003).
Sanchez, et al., "Structural and Functional Characteristics of S1P Receptors", J. Cell. Biochem., 92:913-22 (2004).
Shea, et al., "Prolonged exposure to Sphingosine 1-phosphate receptor-1 Agonists Exacerbates Vascular leak, Fibrosis, and Mortality After Lung Injury", Am. J. Respir. Cell Mol. Biol., 43(6):662-73 (2010).
Simonneau, et al., "Updated Clinical Classification of Pulmonary Hypertension", J. Am. Coll. Cardiol., 54:S43-54 (2009).
Singleton, et al., "CD44 Regulates Hepatocyte Growth Factor-Mediated vascular Integrity. Role of c-Met, Tiam1/Rac1, Dynamin 2, and Cortactin", J. Biol. Chem., 282:30642-30657 (2007).
Singleton, et al., "Regulation of Sphingosine 1-phosphate-induced Endothelial Cytoskeletal Rearrangement and Barrier Enhancement by S1P1 Receptor, P13 Kinase, Tiam1/Rac1, and Alpha-Actinin", FASEB J., 19:1646-1656 (2005).
Stas, et al., "Immunogenicity Assessment of Antibody Therapeutics", Cambridge University Press, Cambridge, (2009).
Sun, et al., "Pre-B Cell Colony Enhancing Factor (PBEF), a Cytokine With Multiple Physiological Functions", Cytokine & growth factor reviews, 24(5):433-442 (2013).
Takahashi, et al., "Structure and reaction mechanism of human nicotinamide phosphoribosyltransferase", J. Biochem., 147: 95-107 (2010).
Tao, et al., "Mogroside IIIE, a Novel Anti-Fibrotic Compound, Reduces Pulmonary Fibrosis through Toll-Like Receptor 4 Pathways", J. of Pharmacol. Exp. Ther., 361:268-279 (2017).
Travis, et al., "Early Indicators of radiation Injury in the Lung: Are They useful Predictors for Late Changes?", Int. J. Radiat. Oncol. Biol. Phys., 6:1267-1269 (1980).
Tusher, et al., "Significance analysis of Microarrays Applied to the Ionizing Radiation Response", Proc. Natl., Acad. Sci., 98:5116-5121 (2001).
Undas, et al., "Anti-inflammatory and Antithrombotic Effects of Statins in the Management of Coronary Artery Disease", Clin. Lab., 48:287-296 (2002).
Van Walle, et al., "Immunogenicity Screening in Protein Drug Development", Expert Opin. Biol. Ther., 7:405-418 (2007).
Villar, et al., "Current definitions of acute lung injury and the acute respiratory distress syndrome do not reflect their true severity and outcome", Intensive Care Med., 25:930-935 (1999).
Vitali, et al., "The Sugen 5416/hypoxia Mouse Model of Pulmonary Hypertension Revisited: Long-term Follow-Up", Pulm. Circ. 4(4): 619-629 (2014).

(56) References Cited

OTHER PUBLICATIONS

Vujaskovic, et al., "The physical parameters and molecular events associated with radiation-induced lung toxicity", Semin. Radiat. Oncol., 10:296-307 (2000).

Wang, et al., "Structure of Nampt/PBEF/visfatin, a Mammalian NAD+ Biosynthetic Enzyme", Nat. Struct. Mol. Biol., 13:661-662. (2006).

Wheeler, et al., "Acute Lung Injury and the Acute Respiratory Distress Syndrome: A Clinical review", Lancet, 369:1553-64 (2007).

Williams, et al., "Effect of Administration of Lovastatin on the Development of Late Pulmonary effects After Whole-Lung Irradiation in a Murine Model", Radiat. Res., 161:560-567 (2004).

Yeager, et al., "Animal Models of Pulmonary Hypertension: Matching Disease Mechanisms to Etiology of the Human Disease", Pulm. Respir. Med. 4(4): 198 (2014).

Zhao, et al., "Inflammation and chronic oxidative Stress in Radiation-Induced Late Normal tissue injury: Therapeutic Implications", Curr. Med. Chem., 16:130-143 (2009).

Zhao, et al., "Intracellular Generation of Sphingosine 1-phosphate in human lung endothelial cells: Role of Lipid Phosphate phosphatae-1 and Sphingosine Kinase 1", J. Biol. Chem., 282:14165-77 (2007).

Zisman, et al., "A Controlled Trial of Sildenafil in Advanced Idiopathic Pulmonary Fibrosis", N. Engl. J. Med., 363(7):620-628 (2010).

* cited by examiner

METHOD TO REDUCE PULMONARY ARTERIAL HYPERTENSION BY ADMINISTERING INHIBITORS OF NICOTINAMIDE PHOSPHORIBOTRANSFERASE

CROSS-REFERENCE TO RELATED APPLICATIONS

This application is a National Phase application under 35 U.S.C. 371 of PCT/US2018/027780, filed on Apr. 16, 2018, which claims priority to and benefit of U.S. Provisional Application No. 62/485,870 entitled "Methods for treating pulmonary hypertension" filed Apr. 14, 2017, the contents of which are herein incorporated by reference in their entirety.

STATEMENT REGARDING FEDERALLY SPONSORED RESEARCH OR DEVELOPMENT

This invention was made with US. government support under grant number U01-HL125208-01, U01 HL066583, P50 HL073994, R41 HL110707, RO1 HL094394, P01 HL134610 and R35-HL135807-01 by the National Heart, Lung, and Blood Institute. The US. Government has certain rights in the invention.

REFERENCE TO SEQUENCE LISTING

The Sequence Listing submitted as a text file named "UA_17_159_PCT_ST25" created on Apr. 16, 2018, and having a size of 17,397 bytes is hereby incorporated by reference.

FIELD OF THE INVENTION

The field of the invention is generally related to compositions, and methods for reducing morbidity and mortality associated with patients who have pulmonary hypertension.

BACKGROUND OF THE INVENTION

Pulmonary arterial hypertension (PAH) is an often fatal disease with a dismal prognosis due to the lack of effective curative therapies. PAH is a progressive disease caused by functional and structural changes in the pulmonary vasculature. The changes lead to increased pulmonary vascular resistance and, eventually right ventricular failure and death. PAH is characterized by vasoconstriction, in situ thrombosis, vascular inflammation, and the proliferation and resistance to programmed cell death (apoptosis) by pulmonary artery smooth muscle cells (PASMC) and pulmonary artery endothelial cells (PAEC). PAEC dysfunction and injury plays a critical role in the pathogenesis of the disease and triggers PASMC proliferation and migration through activation of growth factors and/or disruption of cell survival mediators. A key feature of the pathobiology of PAH is profound pulmonary vascular remodeling for which new therapeutic strategies are desperately needed. Despite recent progress, the precise cellular and molecular basis of PAH development continues to evolve.

Several drugs are currently used for clinical treatment of PAH, including vasodilators, endothelin receptor antagonists, phosphodiesterase inhibitors such as sildenafil and tadalafil, high-dose calcium channel blockers and anticoagulants. However, no current therapeutic regimens produce a cure in PAH, and fails to reduce or reverse the pathology of PAH. The mitigation of PAH physiology and symptoms requires continuous re-dosing, often involving adverse side-effects. Other options for mitigating PAH include surgical procedures, such as atrial septostomy (open heart surgery) are for a limited number of patients with PAH. In addition, these surgeries are complex and can have serious complications, including heart rhythm abnormalities (arrhythmias). For younger patients with idiopathic pulmonary arterial hypertension, a lung or heart-lung transplant may be an option. However, major risks of any type of transplantation include rejection of the transplanted organ and serious infection, and recipients must take immunosuppressant drugs for life to help reduce the chance of rejection. In summary, effective treatments for reducing and/or reversing the effects of chronic and acute PAH in patients have yet to be developed.

Recent work has identified the nicotinamide phosphoribosyltransferase enzyme (NAMPT), also called visfatin and pre-B cell colony-enhancing factor (PBEF), as being associated with cellular processes involved in vascular remodeling. NAMPT is a multifunctional protein with extracellular pro-inflammatory cytokine-like activity as well as intracellular enzymatic activity as a phosphoribosyltransferase, which regulates NAD levels. NAMPT activity has been linked to several processes involving cellular adaptation to stress responses. These include resistance to senescence, apoptosis and increases in cell proliferation and regulation of cellular redox state. At the pathological level, NAMPT promotes inflammatory responses by increasing inflammatory cell survival and increasing pro-inflammatory cytokine production. In vascular cells, NAMPT promotes endothelial cell survival and angiogenic activity as well as smooth muscle cell survival. The precise significance of NAMPT in the onset and progression of chronic and acute PAH has yet to be elucidated.

Therefore, it is an object of the invention to provide compositions, and methods of use thereof for preventing, reducing and reversing the pathophysiological processes that lead to the onset and progression of pulmonary arterial hypertension in a subject.

It is also an object of the invention to provide compositions, devices, grafts, and methods of use thereof to reduce or prevent inappropriate or deleterious vascular remodeling in a subject.

It is a further object of the invention to provide dosage formulations of compositions effective to treat or prevent one or more symptoms of pulmonary arterial hypertension in a subject.

SUMMARY OF THE INVENTION

Inhibition of the expression and function of nicotinamide phosphoribosyltransferase ("NAMPT") reduces and potentially prevents pathophysiological processes that lead to the onset and progression of Pulmonary Arterial Hypertension (PAH) in humans. Compositions including one or more NAMPT inhibitors in an amount effective to reduce or prevent the development and progression of PAH in a human are described. Dosage formulations including an amount of one or more NAMPT inhibitors effective to treat or prevent PAH in a subject in need thereof are also provided.

Provided are pharmaceutical compositions to reduce or prevent Pulmonary Arterial Hypertension (PAH) in a subject in need thereof including one or more inhibitors of nicotinamide phosphoribosyltransferase (NAMPT) enzymatic activity, or one or more inhibitors of NAMPT as a ligand for an inflammatory receptor or one or more inhibitors of the NAMPT receptor. These inhibitors, or combinations thereof, and a pharmaceutically acceptable excipient for administration into the body are provided. The compositions are effective to reduce or prevent vascular remodeling in a subject relative to a control subject. For example, in one embodiment, the compositions are effective to reduce or prevent one or more of the cellular activities associated with vascular remodeling, including vascular inflammation, vascular smooth muscle cell activation, smooth muscle cell proliferation, and endothelial cell to mesenchymal cell transition in a subject relative to a control subject. Inhibitors of NAMPT enzymatic activity, inhibitors of NAMPT as a ligand, or inhibitors of the NAMPT receptor include antibodies, antibody fragments, and proteins having the binding specificity of an antibody. In some embodiments, the inhibitor is an F(Ab) fragment of an antibody, or a divalent F(Ab)2' fragment of an antibody.

An exemplary receptor of NAMPT is human Toll-Like Receptor 4 or TLR4. Therefore, exemplary compositions of inhibitors of NAMPT or NAMPT receptor ligation include antibodies, antibody fragments, or proteins having the binding specificity of antibodies that bind NAMPT or TLR4 and prevent or reduce interaction between NAMPT and TLR4. In some embodiments the anti-NAMPT antibody, or fragment thereof, or protein having the binding affinity thereof binds to an epitope on the NAMPT protein including one or more residues selected from the group consisting of Glu445, Gly446, Lys447, Gly448, Asp449, Leu450, Glu451, Glu452, Tyr453, Gly454, His455, Asp456 and Leu457. In other embodiments, the inhibitor of NAMPT binds to the NAMPT molecule to prevent or reduce the homo-dimerization of NAMPT. In other embodiments, the inhibitor of NAMPT binds to the TLR4 receptor to prevent receptor activation by NAMPT.

Dosage forms depend upon the exact NAMPT inhibitor deployed but include a range between about 30 mg and about 400 mg, inclusive, of one or more antibody or antibody fragment inhibitors of NAMPT for administration by intravenous infusion. In some embodiments, an inhibitor of NAMPT is a F(Ab)2' fragment in an amount for administration by intravenous infusion of between about 30 mg and about 400 mg, inclusive.

Inhibitors of NAMPT expression or function, NAMPT receptor ligation, or inhibitors of the NAMPT receptor TLR4, or combinations thereof, in the form of a functional nucleic acid are also provided. Exemplary functional nucleic acids include antisense molecule, siRNA, miRNA, aptamers, ribozymes, triplex forming molecules, RNAi, and external guide sequences. In some embodiments, one or more functional nucleic acids are expressed from an expression vector.

Inhibitors of NAMPT expression or function, NAMPT receptor ligation, or inhibitors of the NAMPT receptor TLR4, or combinations thereof in the form of a small molecule (defined as having a molecular weight of 2,000 Daltons, more preferably less than 1,000 Daltons) are also provided. Exemplary small molecule inhibitors include FK-866, MS-1-82, Rari049, and A1-pii135. Dosage formulations include between about 10 µg/kg and 3.5 mg/kg body weight of the recipient, inclusive, of one or more small molecule inhibitors of NAMPT enzymatic function, NAMPT receptor ligation, or inhibitors of the NAMPT receptor TLR4. In some embodiments, small molecule inhibitors of NAMPT are administered via the oral route. Therefore, dosage forms of one or more small molecule inhibitors of NAMPT in an effective amount to treat PAH are provided. In an exemplary embodiment, the small molecule inhibitor is Rari049 in an amount of about 2.5 mg/kg body weight of the recipient.

The compositions can also include a delivery vehicle. Preferred vehicles are sterile aqueous solutions. The composition can also include one or more additional therapeutic agents. Exemplary additional therapeutic agents include vasoactive compounds, anti-neointima agents, chemotherapeutic agents, steroidal and non-steroidal anti-inflammatories, conventional immunotherapeutic agents, immune-suppressants, cytokines, chemokines, and growth factors.

Methods including administering anti-NAMPT antibodies, antibody fragments thereof, or NAMPT inhibitor proteins having the binding specificity thereof to a subject by infusion in an amount between 1 mg and 400 mg, more preferably between 20 mg and 200 mg are provided. The methods reduce or prevent vascular inflammation and remodeling in a subject relative to an untreated control subject. In some embodiments, the infusion is carried out over the course of one hour. The administration can be repeated, for example, once per hour, once per day, once per week, once per month, or less frequently. Small molecules are preferably administered orally once a week and antibody and antibody fragments are preferably administered intravenously once a month for a period of time. The methods can administer combinations of NAMPT inhibitors and one or more vasoactive drugs to the subject.

The methods can treat PAH, and/or reduce of prevent one or more symptoms of PAH, in a subject in need thereof. Symptoms of PAH that can be reduced, prevented or otherwise managed include dyspnea, fatigue, angina pectoris (chest pain), syncope, edema (swelling/redness), right heart failure, reduced oral intake, dizziness, tachycardia, and palpitations.

In some embodiments, the subject is at risk of developing, or has developed, PAH and/or other related vascular disorders. The methods can treat acute or chronic PAH, and/or treat, prevent or manage one of more of the symptoms of acute or chronic PAH in the subject relative to an untreated control subject. Acute PAH may occur in the intensive care setting. For example, the methods can treat PAH resulting from one or more of vascular injury, fibro-proliferative disease, immune dysfunction, infectious disease, cardiovascular disease, or drug intake in the subject, relative to an untreated control subject.

BRIEF DESCRIPTION OF THE DRAWINGS

FIG. 5D is a horizontal bar graph showing genome-wide transcriptomic profiling of NAMPT silenced-lung ECs and pathway analysis identifying differentially-regulated pathways.

FIG. 7B is a cartoon illustration showing alignment between the MD-2-TLR4-binding loop (left of FIG. 7B, and FIG. 7C) (99D-111E) and the aligned binding NAMPT loop (457L-445E, and FIG. 7D) (right of FIG. 9B); FIG. 7E is a cartoon illustration showing signature residues in LPS-binding pocket of MD-2-LPS complex: F1 19; I52; L74; L94; LPS-binding pocket; TLR4-binding loop.

FIG. 11A shows Relative NAMPT protein level for Control siRNA and NAMPT siRNA. FIGS. 11B and 11C show BrdU incorporation for each of vehicle, FBS, Control siRNA and NAMPT iRNA.

FIG. 12A shows number of migrated hPAMCs for each of Control, NAMPT and NAMPT+FK866 groups, respectively. FIG. 12B shows % wound closure for each of Control, siRNA, and NAMPT siRNA groups, respectively.

FIG. 14A is a graph of RVSP (mm Hg); FIG. 14B is a graph of RV/(LV+S) (mm Hg); and FIGS. 14C and 14C are graphs of medial thickness index for 50 µM (FIG. 14C) and 100 µM (FIG. 14D) arterioles, for control, anti-NAMPT antibody treated control, MCT and MCT treated with anti-NAMPT antibody.

DETAILED DESCRIPTION OF THE INVENTION

I. Definitions

Figure 1A:
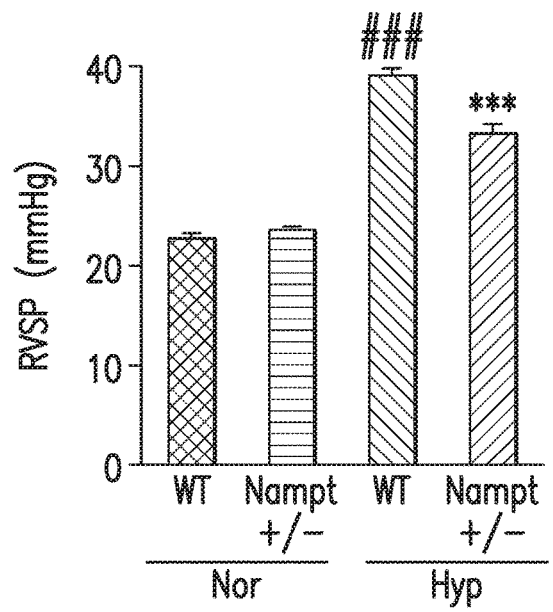
FIG. 1A-1D are bar graphs showing protective effect of reduced NAMPT expression on indices of PAH exhibited by heterozygous NAMPT+/− mice compared to WT controls (WT), with or without exposure to hypoxia. Significant differences were observed in measurements of RVSP (in mmHg) (FIG. 1A), RV hypertrophy (RVH) and RV/(LV+S) (FIG. 1B), and ratios of wall area to total vessel area of PAs<50 um (FIG. 1C) and 50-100 urn in diameter (FIG. 1D). n=10/gp. *p<0.05; p<0.01; *p<0.001 vs hypoxia WT.
Figure 1B:
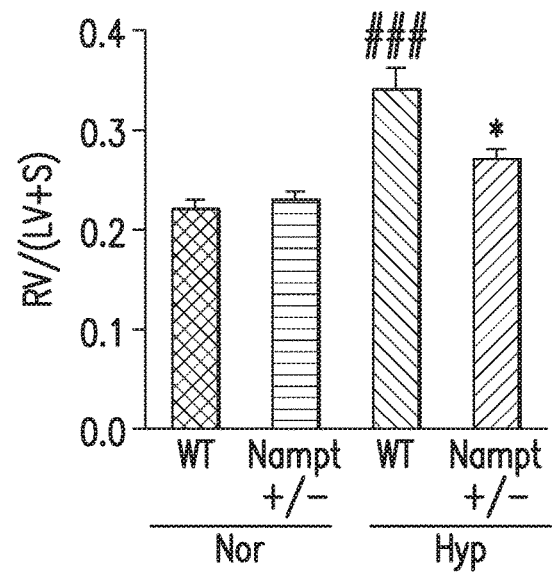
Figure 1C:
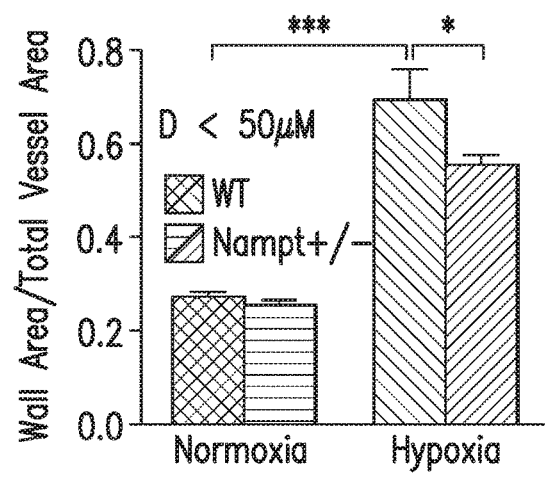
Figure 1D:
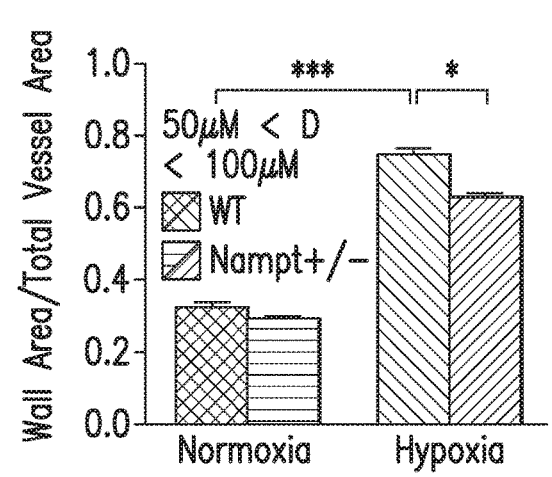

The term "dosing" or "dosage", refers to the administration of a substance (e.g., an anti-NAMPT antibody) to achieve a therapeutic objective (e.g., the treatment of a NAMPT-associated disorder).

The term "pharmaceutically-acceptable carrier" encompasses any of the standard pharmaceutical carriers, such as a phosphate-buffered saline solution, water and emulsions such as an oil/water or water/oil emulsion, and various types of wetting agents.

The term "inhibit" or other forms of the word such as "inhibiting" or "inhibition" means to hinder or restrain a particular characteristic. It is understood that this is typically in relation to some standard or expected value, i.e., it is relative, but that it is not always necessary for the standard or relative value to be referred to. For example, "inhibits" means hindering, interfering with or restraining the activity of the gene relative to a standard or a control. "Inhibits" can also mean to hinder or restrain the synthesis, expression or function of the protein relative to a standard or control.

"Treatment" or "treating" means to administer a composition to a subject or a system with an undesired condition (e.g., hypertension or a cardiovascular disorder). The condition can be a disease or a predisposition to a disease. The effect of the administration of the composition to the subject (either treating and/or preventing symptoms) can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur.

The term "binding" refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Binding partner" or "ligand" refers to a molecule that can undergo specific binding with a particular molecule. "Biological binding" defines a type of interaction that occurs between pairs of molecules including proteins, peptides, nucleic acids, glycoproteins, carbohydrates, or endogenous small molecules. "Specific binding" refers to molecules, such as polynucleotides, that are able to bind to or recognize a binding partner (or a limited number of binding partners) to a substantially higher degree than to other, similar biological entities.

The term "antibody" refers to natural or synthetic antibodies that bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that bind the target antigen. Thus, the term "antibody" encompasses a molecule having at least one variable region from a light chain immunoglobulin molecule and at least one variable region from a heavy chain molecule that in combination form a specific binding site for the target antigen. The antibody can be a IgG antibody, for example, the antibody can be a IgG1, IgG2, IgG3, or IgG4 antibody.

An "antibody fragment" or "antigen binding fragment" (Fab) of an antibody is defined as at least a portion of the variable region of the immunoglobulin molecule that binds to its target, i.e., the antigen-binding region. An antibody can be in the form of an antigen binding antibody fragment including a Fab fragment, F(ab')$_2$ fragment, a single chain variable region, and the like. Fragments of intact molecules can be generated using methods well known in the art and include enzymatic digestion and recombinant means.

As used herein, the term "single chain Fv" or "scFv" as used herein means a single chain variable fragment that includes a light chain variable region ($V_L$) and a heavy chain variable region ($V_H$) in a single polypeptide chain joined by a linker which enables the scFv to form the desired structure for antigen binding (i.e., for the $V_H$ and $V_L$ of the single polypeptide chain to associate with one another to form a Fv). The $V_L$ and $V_H$ regions may be derived from the parent antibody or may be chemically or recombinantly synthesized.

The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917).

The term "Framework Region" or "FR" residues are those variable domain residues other than the hypervariable region residues as herein defined.

A "neutralizing antibody", (or an "antibody that inhibits NAMPT activity"), is intended to refer to an antibody whose binding to NAMPT results in inhibition of the biological activity of NAMPT. This inhibition of the biological activity of NAMPT, or its ligands, can be assessed by measuring one or more indicators of NAMPT biological activity, such as quantities of extracellular NAMPT (either in vitro or in vivo), NAMPT-induced cellular activation (e.g., NFkB phosphorylation) and NAMPT binding to NAMPT ligands. These indicators of NAMPT biological activity can be assessed by one or more of several standard in vitro or in vivo assays known in the art (see Examples). For example, in one embodiment, the ability of an antibody to inhibit NAMPT activity is assessed by inhibition of NAMPT-induced activation of endothelial cells. As an additional or alternative parameter of NAMPT activity, the ability of an antibody to inhibit NAMPT-induced transcription activities via NFKB as a measure of NAMPT-induced cellular activation, can be assessed.

Any form of the "antigen" can be used to generate an antibody that is specific for a target antigen. Thus, the eliciting antigen may contain a single epitope, multiple epitopes, or can be the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA). Any genetic vectors suitable for transformation of the cells of interest may be employed, including but not limited to adenoviral vectors, plasmids, and non-viral vectors, such as cationic lipids.

As used herein, the term "specifically binds" refers to the binding of an antibody to its cognate antigen while not significantly binding to other antigens. Preferably, an antibody "specifically binds" to an antigen with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with that second molecule.

As used herein, the term "monoclonal antibody" or "MAb" refers to an antibody obtained from a substantially homogeneous population of antibodies, i.e., the individual antibodies within the population are identical except for possible naturally occurring mutations that may be present in a small subset of the antibody molecules.

As used herein, the terms "inhibit" and "inhibition" mean to decrease an activity, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, the term "fusion protein" refers to a polypeptide formed by the joining of two or more polypeptides through a peptide bond formed between the amino terminus of one polypeptide and the carboxyl terminus of another polypeptide or through linking of one polypeptide to another through reactions between amino acid side chains (for example disulfide bonds between cysteine residues on each polypeptide). The fusion protein can be formed by the chemical coupling of the constituent polypeptides or it can be expressed as a single polypeptide from a nucleic acid sequence encoding the single contiguous fusion protein. Fusion proteins can be prepared using conventional techniques in molecular biology to join the two genes in frame into a single nucleic acid sequence, and then expressing the nucleic acid in an appropriate host cell under conditions in which the fusion protein is produced.

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest. The term "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or includes a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "$K_{off}$", is intended to refer to the off rate constant for dissociation of an interaction between a molecule and its ligand, for example, an antibody from the antibody/antigen complex.

The term "$K_d$", as used herein, is intended to refer to the dissociation constant of a particular antibody-antigen interaction.

The term "vascular remodeling" refers to a combined physiological process excessive cellular proliferation, fibrosis, and reduced apoptosis/programmed cell death in the vessel walls, caused by inflammation, disordered metabolism and dysregulation of certain growth factors.

The terms "monthly dosing regimen", "monthly dosing", and "monthly administration", as used herein, refer to the time course of administering a substance (e.g., an anti-NAMPT antibody) to a subject to achieve a therapeutic objective (e.g., the treatment of a NAMPT-associated disorder). The monthly dosing regimen is not intended to include a weekly dosing regimen. Preferably, the substance is administered every 26-36 days, more preferably, every 28-31 days, even more preferably, every 28-30 days, and most preferably, every 30 days.

The term "human NAMPT" (abbreviated herein as hNAMPT, or simply NAMPT), as used herein, is intended to refer to a human nicotinamide phosphoribosyltransferase enzyme that exists as a 120 kD secreted dimeric form, the biologically active form of which is composed of a dimer of noncovalently bound 55-60 kD molecules. The structure of NAMPT is described further in, for example, Kim, et al. *J Mol Biol.*; 362:66-77 (2006).

The term NAMPT is intended to include recombinant human NAMPT, which can be prepared by standard recombinant expression methods. The human NAMPT gene is referred to as NAMPT.

II. Compositions

Dosage formulations include one or more inhibitors of NAMPT and/or one or more inhibitors of a NAMPT receptor effective to treat one or more symptoms of PAH in a human. Compositions for treatment of PAH include: i) inhibitors of the expression and function of the NAMPT gene; ii) inhibitors of the enzymatic activity of the NAMPT gene product; iii) manipulation of the interaction of the NAMPT gene product with its receptor, TLR4 (NAMPT/TLR4), iv) neutralization of circulating extracellular NAMPT (eNAMPT); v) manipulation of one or more of the downstream cellular signaling events associated with NAMPT/TLR4 such as NFkB phosphorylation/activation. Loss of function of the NAMPT gene product gives rise to abnormal function in cellular processes associated with vascular remodeling, resulting in an associated reduction in the onset, development and severity of PAH in human subjects.

Compositions for treating diseases and/or symptoms characterized by vascular remodeling by blockade of expression and/or function of the NAMPT enzyme are provided.

A. Targets of Enzymatic Inhibition

1. Nicotinamide Phosphoribosyltransferase (NAMPT)

In some embodiments, the target of inhibition is nicotinamide phosphoribosyltransferase (NAMPT). The NAMPT gene product is the rate-limiting enzyme in the nicotinamide adenine dinucleotide (NAD+) salvage pathway that converts nicotinamide to nicotinamide mononucleotide in mammals to enable NAD+ biosynthesis.

The mature form of the extracellular NAMPT protein is a homodimer of approximately 120 kDa, each monomer having approximately 500 amino acid residues (Takahashi, et al., *J. Biochem.* 147: 95-107 (2010)).

It has been established that mutations which reduce or inhibit the function of the NAMPT enzyme reduce or prevent the pathophysiological processes that give rise to PAH. It is believed that modulation of the NAMPT enzyme provides a means to modulate pathophysiological processes that give rise to vascular remodeling associated with PAH.

a. The NAMPT Gene

The human NAMPT gene (NAMPT) is located at chromosome 7, (segment 7q22.3; base pairs 106,248,285 to 106,286,326). Nucleic acid sequences for the human NAMPT gene product are known in the art. See, for example, NCBI Reference Sequence: NM_005746.2, *Homo sapiens* nicotinamide phosphoribosyltransferase (NAMPT), mRNA, which provides the nucleic acid sequence:

(SEQ ID NO: 1)
```
ATGAATCCTG CGGCAGAAGC CGAGTTCAAC ATCCTCCTGG CCACCGACTC CTACAAGGTT

ACTCACTATA AACAATATCC ACCCAACACA AGCAAAGTTT ATTCCTACTT TGAATGCCGT

GAAAAGAAGA CAGAAAACTC CAAATTAAGG AAGGTGAAAT ATGAGGAAAC AGTATTTTAT

GGGTTGCAGT ACATTCTTAA TAAGTACTTA AAAGGTAAAG TAGTAACCAA AGAGAAAATC

CAGGAAGCCA AAGATGTCTA CAAAGAACAT TTCCAAGATG ATGTCTTTAA TGAAAAGGGA

TGGAACTACA TTCTTGAGAA GTATGATGGG CATCTTCCAA TAGAAATAAA AGCTGTTCCT

GAGGGCTTTG TCATTCCCAG AGGAAATGTT CTCTTCACGG TGGAAAACAC AGATCCAGAG

TGTTACTGGC TTACAAATTG GATTGAGACT ATTCTTGTTC AGTCCTGGTA TCCAATCACA

GTGGCCACAA ATTCTAGAGA GCAGAAGAAA ATATTGGCCA AATATTTGTT AGAAACTTCT

GGTAACTTAG ATGGTCTGGA ATACAAGTTA CATGATTTTG GCTACAGAGG AGTCTCTTCC
```

```
                                        -continued
CAAGAGACTG CTGGCATAGG AGCATCTGCT CACTTGGTTA ACTTCAAAGG AACAGATACA

GTAGCAGGAC TTGCTCTAAT TAAAAAATAT TATGGAACGA AAGATCCTGT TCCAGGCTAT

TCTGTTCCAG CAGCAGAACA CAGTACCATA ACAGCTTGGG GGAAAGACCA TGAAAAAGAT

GCTTTTGAAC ATATTGTAAC ACAGTTTTCA TCAGTGCCTG TATCTGTGGT CAGCGATAGC

TATGACATTT ATAATGCGTG TGAGAAAATA TGGGGTGAAG ATCTAAGACA TTTAATAGTA

TCGAGAAGTA CACAGGCACC ACTAATAATC AGACCTGATT CTGGAAACCC TCTTGACACT

GTGTTAAAGG TTTTGGAGAT TTTAGGTAAG AAGTTTCCTG TTACTGAGAA CTCAAAGGGT

TACAAGTTGC TGCCACCTTA TCTTAGAGTT ATTCAAGGGG ATGGAGTAGA TATTAATACC

TTACAAGAGA TTGTAGAAGG CATGAAACAA AAAATGTGGA GTATTGAAAA TATTGCCTTC

GGTTCTGGTG GAGGTTTGCT ACAGAAGTTA ACAAGAGATC TCTTGAATTG TTCCTTCAAG

TGTAGCTATG TTGTAACTAA TGGCCTTGGG ATTAACGTCT TCAAGGACCC AGTTGCTGAT

CCCAACAAAA GGTCCAAAAA GGGCCGATTA TCTTTACATA GGACGCCAGC AGGGAATTTT

GTTACACTGG AGGAAGGAAA AGGAGACCTT GAGGAATATG GTCAGGATCT TCTCCATACT

GTCTTCAAGA ATGGCAAGGT GACAAAAAGC TATTCATTTG ATGAAATAAG AAAAAATGCA

CAGCTGAATA TTGAACTGGA AGCAGCACAT CATTAG.
```

Nucleotide sequences that have at least 80%, 85%, 90%, 95%, 99% or 100% amino acid sequence identity to SEQ ID NO: 1 are also disclosed.

b. The NAMPT Enzyme

The NAMPT polypeptide is a 473 amino acid cytoplasmic protein (also known as nicotinamide phosphoribosyltransferase, pre-B-cell colony-enhancing factor (PBEF) protein) with a molecular weight of approximately 52,521 Da. There are three mRNA variants, with lengths of 2.0, 2.4, and 4.0 kilobases (kb), transcribed by the NAMPT gene. The 2.4-kb variant is the most abundant and its open reading frame encodes a protein of 473 amino acids (aa) in length, with a predicted size of approximately 52 kDa (Samal, et al. *Mol. Cell. Biol.* 14 (2), 1431-1437 (1994)). It has been found in human endothelial cells, where it is able to induce angiogenesis through upregulation of VEGF and VEGFR and secretion of MCP-1. In human umbilical endothelial cells, NAMPT increases levels of the protease MMP 2/9. NAMPT has also been found in a variety of immune cells other than B cells and has been shown to inhibit apoptosis of macrophages and endothelial cells. Extracellular NAMPT (eNAMPT) has been shown to increase NFkB activation and subsequent induction of inflammatory cytokines, such as TNF-α, IL-1β, IL-16, and TGF-β1, and the chemokine receptor CCR3. NAMPT also increases the production of IL-6, TNF-α, and IL-1β in CD14+ monocyctes, macrophages, and dendritic cells, enhances the effectiveness of T cells, and is involved in the development of both B and T lymphocytes (Sun, et al., Cytokine & growth factor reviews 24(5):433-442 (2013)).

The NAMPT enzyme crystal structure is described in detail in Kim, et al. *J Mol Biol.;* 362:66-77 (2006). NAMPT is a dimeric type II phosphoribosyltransferase. The active site of the enzyme is at the dimer interface where the two NAMPT molecules interact. In the apoenzyme structure, a sulfate ion binds in place of the phosphate of NMN. A hydrogen bond between Asp219 and the amide of nicotinamide prevents the enzyme from forming a hydrogen bond to nicotinic or quinolinic acid. Crystal structures of NAMPT are available in the Protein Data Bank as PDB ID Nos. 2G95, 2G96 and 2G97 Amino acid sequences of the human NAMPT enzyme are known in the art. See, for example, GenBank Accession No. NP_005737.1:

```
                                                              (SEQ ID NO: 2)
              10         20         30         40         50
         MNPAAEAEFN ILLATDSYKV THYKQYPPNT SKVYSYFECR EKKTENSKLR 60         70         80         90        100
         KVKYEETVFY GLQYILNKYL KGKVVTKEKI QEAKDVYKEH FQDDVFNEKG 110        120        130        140        150
         WNYILEKYDG HLPIEIKAVP EGFVIPRGNV LFTVENTDPE CYWLTNWIET 160        170        180        190        200
         ILVQSWYPIT VATNSREQKK ILAKYLLETS GNLDGLEYKL HDFGYRGVSS 210        220        230        240        250
         QETAGIGASA HLVNFKGTDT VAGLALIKKY YGTKDPVPGY SVPAAEHSTI 260        270        280        290        300
         TAWGKDHEKD AFEHIVTQFS SVPVSVVSDS YDIYNACEKI WGEDLRHLIV 310        320        330        340        350
         SRSTQAPLII RPDSGNPLDT VLKVLEILGK KFPVTENSKG YKLLPPYLRV
```

```
        360        370        380        390        400
IQGDGVDINT LQEIVEGMKQ KMWSIENIAF GSGGGLLQKL TRDLLNCSFK 410        420        430        440        450
CSYVVTNGLG INVFKDPVAD PNKRSKKGRL SLHRTPAGNF VTLEEGKGDL 460        470        480        490
EEYGQDLLHT VFKNGKVTKS YSFDEIRKNA QLNIELEAAH H
```

NAMPT polypeptides that have, for example, at least 80%, 85%, 90%, 95%, 99% or 100% amino acid sequence identity to SEQ ID NO: 2.

The NAMPT enzyme has been associated with many diverse cellular activities, however the biological function of the NAMPT enzyme in the onset and progression of PAH have been unknown.

The region of dimerization within the mature form of the NAMPT enzyme is described in the X-ray crystal structure of NAMPT, described in Wang, et al., *Nat Struct Mol Biol*, 13, 661-662. (2006). Residues involved in the interface include Ser199 and Ser200. It may be that the NAMPT protein interacts with one or more ligands through interaction by hydrogen bonding with one or more residues selected from Glu445, Gly446, Lys447, Gly448, Asp449, Leu450, Glu451, Glu452, Tyr453, Gly454, Gln455, Asp456 and Leu457. These residues form a loop that may interact with TLR4 in a manner analogous to MD-2.

2. NAMPT Receptors

In some embodiments, the target of inhibition are the receptors for NAMPT, such as Toll-like receptor 4 (TLR4). Toll-like receptor 4 is a protein that in humans is encoded by the TLR4 gene. TLR4 is a transmembrane protein and a member of the toll-like receptor family, which belongs to the pattern recognition receptor (PRR) family Its activation leads to an intracellular NF-κB signaling pathway and inflammatory cytokine production which is responsible for activating the innate immune system. It is most well known for recognizing lipopolysaccharide (LPS), a component present in many Gram-negative bacteria (e.g. *Neisseria* spp.) and select Gram-positive bacteria. Its ligands also include several viral proteins, polysaccharide, and a variety of endogenous proteins such as low-density lipoprotein, beta-defensins, and heat shock protein.

The human TLR4 gene (TLR4) is located at chromosome 9, (segment 9q32-q33) (Georgel, et al., *PLoS ONE* 4(11): e7803 (2009)). Nucleic acid sequences for the human TLR4 gene product are known in the art. See, for example, NCBI Reference Sequence: AAY82268.1, *Homo sapiens* toll-like receptor 4 (TLR4), mRNA, which provides the nucleic acid sequence:

```
                                                (SEQ ID NO: 3)
ATGATGTCTG CCTCGCGCCT GGCTGGGACT CTGATCCCAG CCATGGCCTT CCTCTCCTGC

GTGAGACCAG AAAGCTGGGA GCCCTGCGTG GAGGTGGTTC CTAATATTAC TTATCAATGC

ATGGAGCTGA ATTTCTACAA AATCCCCGAC AACCTCCCCT TCTCAACCAA GAACCTGGAC

CTGAGCTTTA ATCCCCTGAG GCATTTAGGC AGCTATAGCT TCTTCAGTTT CCCAGAACTG

CAGGTGCTGG ATTTATCCAG GTGTGAAATC CAGACAATTG AAGATGGGGC ATATCAGAGC

CTAAGCCACC TCTCTACCTT AATATTGACA GGAAACCCCA TCCAGAGTTT AGCCCTGGGA

GCCTTTTCTG GACTATCAAG TTTACAGAAG CTGGTGGCTG TGGAGACAAA TCTAGCATCT

CTAGAGAACT TCCCCATTGG ACATCTCAAA ACTTTGAAAG AACTTAATGT GGCTCACAAT

CTTATCCAAT CTTTCAAATT ACCTGAGTAT TTTTCTAATC TGACCAATCT AGAGCACTTG

GACCTTTCCA GCAACAAGAT TCAAAGTATT TATTGCACAG ACTTGCGGGT TCTACATCAA

ATGCCCCTAC TCAATCTCTC TTTAGACCTG TCCCTGAACC CTATGAACTT TATCCAACCA

GGTGCATTTA AAGAAATTAG GCTTCATAAG CTGACTTTAA GAAATAATTT TGATAGTTTA

AATGTAATGA AAACTTGTAT TCAAGGTCTG GCTGGTTTAG AAGTCCATCG TTTGGTTCTG

GGAGAATTTA GAAATGAAGG AAACTTGGAA AAGTTTGACA AATCTGCTCT AGAGGGCCTG

TGCAATTTGA CCATTGAAGA ATTCCGATTA GCATACTTAG ACTACTACCT CGATGATATT

ATTGACTTAT TTAATTGTTT GACAAATGTT TCTTCATTTT CCCTGGTGAG TGTGACTATT

GAAAGGGTAA AAGACTTTTC TTATAATTTC GGATGGCAAC ATTTAGAATT AGTTAACTGT

AAATTTGGAC AGTTTCCCAC ATTGAAACTC AAATCTCTCA AAAGGCTTAC TTTCACTTCC

AACAAAGGTG GGAATGCTTT TTCAGAAGTT GATCTACCAA GCCTTGAGTT TCTAGATCTC

AGTAGAAATG GCTTGAGTTT CAAAGGTTGC TGTTCTCAAA GTGATTTTGG GACAACCAGC

CTAAAGTATT TAGATCTGAG CTTCAATGGT GTTATTACCA TGAGTTCAAA CTTCTTGGGC
```

```
TTAGAACAAC TAGAACATCT GGATTTCCAG CATTCCAATT TGAAACAAAT GAGTGAGTTT

TCAGTATTCC TATCACTCAG AAACCTCATT TACCTTGACA TTTCTCATAC TCACACCAGA

GTTGCTTTCA ATGGCATCTT CAATGGCTTG TCCAGTCTCG AAGTCTTGAA AATGGCTGGC

AATTCTTTCC AGGAAAACTT CCTTCCAGAT ATCTTCACAG AGCTGAGAAA CTTGACCTTC

CTGGACCTCT CTCAGTGTCA ACTGGAGCAG TTGTCTCCAA CAGCATTTAA CTCACTCTCC

AGTCTTCAGG TACTAAATAT GAGCCACAAC AACTTCTTTT CATTGGATAC GTTTCCTTAT

AAGTGTCTGA ACTCCCTCCA GGTTCTTGAT TACAGTCTCA ATCACATAAT GACTTCCAAA

AAACAGGAAC TACAGCATTT TCCAAGTAGT CTAGCTTTCT TAAATCTTAC TCAGAATGAC

TTTGCTTGTA CTTGTGAACA CCAGAGTTTC CTGCAATGGA TCAAGGACCA GAGGCAGCTC

TTGGTGGAAG TTGAACGAAT GGAATGTGCA ACACCTTCAG ATAAGCAGGG CATGCCTGTG

CTGAGTTTGA ATATCACCTG TCAGATGAAT AAGACCATCA TTGGTGTGTC GGTCCTCAGT

GTGCTTGTAG TATCTGTTGT AGCAGTTCTG GTCTATAAGT TCTATTTTCA CCTGATGCTT

CTTGCTGGCT GCATAAAGTA TGGTAGAGGT GAAAACATCT ATGATGCCTT TGTTATCTAC

TCAAGCCAGG ATGAGGACTG GGTAAGGAAT GAGCTAGTAA AGAATTTAGA AGAAGGGGTG

CCTCCATTTC AGCTCTGCCT TCACTACAGA GACTTTATTC CCGGTGTGGC CATTGCTGCC

AACATCATCC ATGAAGGTTT CCATAAAAGC CGAAAGGTGA TTGTTGTGGT GTCCCAGCAC

TTCATCCAGA GCCGCTGGTG TATCTTTGAA TATGAGATTG CTCAGACCTG GCAGTTTCTG

AGCAGTCGTG CTGGTATCAT CTTCATTGTC CTGCAGAAGG TGGAGAAGAC CCTGCTCAGG

CAGCAGGTGG AGCTGTACCG CCTTCTCAGC AGGAACACTT ACCTGGAGTG GGAGGACAGT

GTCCTGGGGC GGCACATCTT CTGGAGACGA CTCAGAAAAG CCCTGCTGGA TGGTAAATCA

TGGAATCCAG AAGGAACAGT GGGTACAGGA TGCAATTGGC AGGAAGCAAC ATCTATCTGA.
```

Nucleotide sequences that have at least 80%, 85%, 90%, 95%, 99% or 100% amino acid sequence identity to SEQ ID NO: 3 are also disclosed.

Amino acid sequences of the human TLR4 are known in the art. See, for example, GenBank Accession No. AAY82268.1:

```
                                                    (SEQ ID NO: 4)
         10         20         30         40         50
 MMSASRLAGT LIPAMAFLSC VRPESWEPCV EVVPNITYQC MELNFYKIPD 60         70         80         90        100
 NLPFSTKNLD LSFNPLRHLG SYSFFSFPEL QVLDLSRCEI QTIEDGAYQS 110        120        130        140        150
 LSHLSTLILT GNPIQSLALG AFSGLSSLQK LVAVETNLAS LENFPIGHLK 160        170        180        190        200
 TLKELNVAHN LIQSFKLPEY FSNLTNLEHL DLSSNKIQSI YCTDLRVLHQ 210        220        230        240        250
 MPLLNLSLDL SLNPMNFIQP GAFKEIRLHK LTLRNNFDSL NVMKTCIQGL 260        270        280        290        300
 AGLEVHRLVL GEFRNEGNLE KFDKSALEGL CNLTIEEFRL AYLDYYLDDI 310        320        330        340        350
 IDLFNCLTNV SSFSLVSVTI ERVKDFSYNF GWQHLELVNC KFGQFPTLKL 360        370        380        390        400
 KSLKRLTFTS NKGGNAFSEV DLPSLEFLDL SRNGLSFKGC CSQSDFGTTS 410        420        430        440        450
 LKYLDLSFNG VITMSSNFLG LEQLEHLDFQ HSNLKQMSEF SVFLSLRNLI 460        470        480        490        500
 YLDISHTHTR VAFNGIFNGL SSLEVLKMAG NSFQENFLPD IFTELRNLTF
```

```
             510        520        530        540        550
      LDLSQCQLEQ LSPTAFNSLS SLQVLNMSHN NFFSLDTFPY KCLNSLQVLD 560        570        580        590        600
      YSLNHIMTSK KQELQHFPSS LAFLNLTQND FACTCEHQSF LQWIKDQRQL 610        620        630        640        650
      LVEVERMECA TPSDKQGMPV LSLNITCQMN KTIIGVSVLS VLVVSVVAVL 660        670        680        690        700
      VYKFYFHLML LAGCIKYGRG ENIYDAFVIY SSQDEDWVRN ELVKNLEEGV 710        720        730        740        750
      PPFQLCLHYR DFIPGVAIAA NIIHEGFHKS RKVIVVVSQH FIQSRWCIFE 760        770        780        790        800
      YEIAQTWQFL SSRAGIIFIV LQKVEKTLLR QQVELYRLLS RNTYLEWEDS 810        820        830
      VLGRHIFWRR LRKALLDGKS WNPEGTVGTG CNWQEATSI.
```

TLR4 polypeptides that have at least 80%, 85%, 90%, 95%, 99% or 100% amino acid sequence identity to SEQ ID NO: 4 are described.

Lymphocyte antigen 96, also known as "MD2" is a protein that is associated with TLR4 on the cell surface and enables TLR4 to respond to LPS. MD-2 also enables TLR4 to respond to a wide variety of endotoxic LPS partial structures, Gram-negative bacteria, and Gram-positive lipoteichoic acid, but not to Gram-positive bacteria, peptidoglycan, and lipopeptide. MD-2 physically associates with TLR4 and TLR2, but the association with TLR2 is weaker than with TLR4. MD-2 and TLR4 enhance each other's expression (Dziarski, et al., *J Endotoxin Res.* 6(5):401-5 (2000)).

It has been established that TLR4 is a receptor for extracellular NAMPT (eNAMPT). It may be that eNAMPT binds to TLR4 in the region of the interaction with MD2. Therefore, antibodies, small molecules and functional nucleic acids that bind to TLR4 in the region of the interaction with MD2 are described.

B. Inhibitors of NAMPT and NAMPT Receptors

Blockade of NAMPT expression and/or function can reduce or prevent immune processes that give rise to the onset and development of chronic and acute PAH. Agents that inhibit or reduce the transcription, translation or function of the NAMPT enzyme, or which inhibit the interaction of NAMPT with TLR4 (NAMPT/TLR4) are described.

Inhibitors of NAMPT can bind to the NAMPT gene or to NAMPT polypeptide and directly or indirectly block the biological function of NAMPT polypeptide. Inhibitors can also block the biological function of one or more signaling pathways that constitute the down-stream biological function of NAMPT. In some embodiments, inhibitors of NAMPT act by preventing endogenous receptors of the NAMPT polypeptide from interacting with or binding directly to the NAMPT polypeptide. The inhibitors can block protein-protein interactions involving the NAMPT polypeptide, or they can prevent or reduce the functional activity of a complex of the NAMPT enzyme and a receptor. Inhibitors that bind directly to the NAMPT polypeptide may act by direct occlusion of an active site on the NAMPT polypeptide, or through indirect occlusion, such as by stearic blockade of NAMPT interactions. For example, in some embodiments the inhibitor obstructs or occludes the function of a protein interaction domain, such as the enzyme active site, or the site of homo-dimerization between two NAMPT monomers within the active NAMPT polypeptide, or the site of interaction with a receptor, for example, the site of interaction with TLR4. In other embodiments, inhibitors bind to a location that is spatially distinct from an active site. Therefore, in certain embodiments, inhibitors that bind to the NAMPT polypeptide can prevent NAMPT function by mechanisms including, but not limited to, preventing or disrupting dimerization, inducing oligomerization, inducing conformational changes, preventing catalytic functions, inducing degradation, inducing uptake by immune cells, preventing uptake by target cells, preventing ligand binding, preventing phosphorylation, inducing denaturation, preventing one or more post-translational modifications or otherwise altering the native tertiary structure of the NAMPT polypeptide.

It is understood that initiation or transduction of cellular signaling pathways by NAMPT can require binding of a ligand to the NAMPT polypeptide. Therefore, proteins, antibodies or small molecules that block signal transduction pathways involving NAMPT and optionally prevent co-ligation of NAMPT and its receptors are useful immune-modulatory agents. Classes of NAMPT inhibitors discussed below include antibodies, Fab fractions of antibodies and functional nucleic acids that bind directly to the NAMPT polypeptide, as well as antibodies, Fab fractions of antibodies and functional nucleic acids that bind to ligands of NAMPT.

1. Antibodies

Antibodies that inhibit the function of NAMPT by specific interaction directly with the NAMPT enzyme, its receptors, or its accessory molecules are provided. Antibodies can include an antigen binding site that binds to an epitope on the NAMPT enzyme. Binding of an antibody to NAMPT can inhibit or reduce the function of the NAMPT enzyme via one or more distinct mechanisms. Typically, the antibodies can reduce NAMPT biological activity in vitro and in vivo. In some embodiments, the antibodies have high affinity for NAMPT (e.g., $K_d=10^{-8}$ M or less), a slow off rate for NAMPT dissociation (e.g., $K_{off}=10^{-3}$ sec$^{-1}$, or less), or a combination thereof.

Full-length antibodies, antigen binding fragments thereof, and fusion proteins based thereon are provided. Useful antibodies and antigen-binding fragments thereof are typically characterized by binding to NAMPT, or one or more ligands of NAMPT, preferably with high affinity and slow dissociation kinetics. In some embodiments, the antibodies, or antigen-binding fragments thereof inhibit NAMPT activity, including NAMPT-induced transcription through NFKB (in vitro and in vivo) and NAMPT-induced cellular activation. The antibodies can be full-length (e.g., an IgG subtype 1, or IgG4 antibody) or can comprise only an antigen-binding portion (e.g., a Fab, F(ab')2' scFv fragment, or F(Ab) single domain). An exemplary recombinant antibody binds an epitope including two or more of the amino acid residues set forth in SEQ ID NO. 2.

In some embodiments, inhibitors of NAMPT, or ligands of NAMPT, are proteins that have the antigen-binding specificity of an antibody, such as a fragment of an antibody. The term "antigen-binding portion" of an antibody (or simply "antibody portion"), refers to one or more fragments of an antibody that retain the ability to specifically bind to an antigen (e.g., NAMPT).

Various types of antibodies and antibody fragments can be used, including whole immunoglobulin of any class, fragments thereof, and synthetic proteins containing at least the antigen binding variable domain of an antibody. The antibody can be an IgG antibody, such as IgG1, IgG2, IgG3, or IgG$_4$. An antibody can be in the form of an antigen binding fragment including a Fab fragment, F(ab')2 fragment, a single chain variable region, and the like. Antibodies can be polyclonal or monoclonal (mAb).

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., *Proc. Natl. Acad. Sci. USA*, 81: 6851-6855 (1984)).

The antigen-binding function of an antibody can be performed by fragments of a full-length antibody. Examples of binding fragments encompassed within the term "antigen binding portion" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

a. Characteristics of the Antibodies

In some embodiments, the antibody or antigen binding fragment binds specifically to an epitope within the protein encoded by the amino acid sequence of SEQ ID NO: 2. A linear epitope is an epitope that formed by a continuous sequence of amino acids from the antigen. Linear epitopes typically include approximately 5 to about 10 continuous amino acid residues. Antibodies bind a linear epitope based on the primary sequence of the antigen. Thus, in some embodiments, the epitope can be a linear epitope and can include 1, 2, 3, 4, 5, 6, 7, 8, 9, 10, or more consecutive amino acids of the primary sequence of SEQ ID NO: 2. A "conformational epitope" is an epitope that includes discontinuous sections of the antigen's amino acid sequence. Antibodies bind a conformational epitope based on 3-D surface features, shape, or tertiary structure of the antigen. Thus, in some embodiments, the antibody or antigen binding fragment thereof can bind a conformational epitope that includes a 3-D surface feature, shape, or tertiary structure of the NAMPT enzyme. In some embodiments, a 3-D surface feature can include any number of amino acids from SEQ ID NO: 2, or the corresponding residues in a homolog, ortholog, paralog, or variant thereof.

In some embodiments, the antibody or antigen binding fragment thereof interferes with the interaction between NAMPT and TLR4. NAMPT may bind to TLR4 through a binding loop including some or all of the residues in the amino acid sequence EGKGDLEEYGHDL (SEQ ID NO:5) corresponding with amino acids 445 through 457 of SEQ ID NO:2. In some embodiments, SEQ ID NO: 5 serves as part or all of an antigen for producing an anti-NAMPT antibody. In some embodiments, SEQ ID NO: 5, or residues thereof, form part or all of the epitope to which the antibody binds. In some embodiments, SEQ ID NO: 5 forms part or all of a conformation epitope.

In some embodiments, the antibody or antigen binding fragment that binds specifically to an epitope within the protein encoded by the amino acid sequence of SEQ ID NO: 2 can only bind if the protein encoded by the amino acid sequence of SEQ ID NO: 2 is not bound by a ligand or small molecule.

In some embodiments, the antibody or antigen binding portion thereof dissociates from human NAMPT, or a ligand of human NAMPT, with a $K_{off}$ rate constant of $1 \times 10^{-1}/s^{-1}$ or less. Preferably, the antibody, or antigen-binding portion thereof, dissociates from human NAMPT, or a ligand of human NAMPT with a $K_{off}$ rate constant of $5 \times 10^{-4}/s^{-1}$ or less. Even more preferably, the antibody, or antigen binding portion thereof, dissociates from human NAMPT, or a ligand of human NAMPT with a $K_{off}$ rate constant of $1 \times 10/s^{-1}$ or less or less. Typically, the anti-NAMPT antibody binds an epitope formed by two or more amino acid residues at the surface of the tertiary structure of the NAMPT enzyme formed by the amino acid sequence of SEQ ID NO: 2. Exemplary suitable antibodies are also discussed in U.S. Pat. No. 9,409,983.

Commercial antibodies specific for NAMPT are available. For example, polyclonal and monoclonal rabbit, mouse or rat anti-human NAMPT antibodies are commercially available from multiple vendors (e.g., Rabbit anti-human NAMPT polyclonal Antibody (Thermo-Fischer scientific Catalog #PAS-34858); mouse anti-human NAMPT monoclonal antibody 1D3A12 (Thermo-Fischer scientific Catalog #MA5-15388); or rat anti-human NAMPT monoclonal antibody 362616 (Thermo-Fischer scientific Catalog #MA5-24108)).

Rabbit and mouse polyclonal and monoclonal anti-human TLR4 antibodies are commercially available from multiple vendors (e.g., Rabbit anti-human TLR4 polyclonal Antibody (Thermo-Fischer scientific Catalog #48-2300); mouse anti-human TLR4 monoclonal antibody HTA125 (Thermo-Fischer scientific Catalog #14-9917-82); or mouse polyclonal antibody (Thermo-Fischer scientific Catalog #36-3700)).

In some embodiments, a commercially available antibody is used. In some embodiments, the antibody is a humanized or chimeric antibody or an antigen-binding fragment thereof (e.g., a single chain antibody), having one, two, three, four, five, or six CDRs from a commercially available antibody, or having variant CDRs thereof having 65, 70, 75, 80, 85, 90, 95, 96, 97, 98, or 99 percent sequence identity to the corresponding CDRs of commercially available antibody.

In some embodiments, the antibody has the same epitope specificity as a commercially available anti-NAMPT antibody or anti-TRL4 antibody or an anti-NAMPT antibody or anti-TRL4 antibody that is otherwise known in the art. This can be achieved by producing a recombinant antibody that contains the paratope of the commercially or otherwise available antibody.

b. Antibody Composition and Methods of Manufacture

To prepare an antibody that specifically binds to NAMPT or a receptor thereof, purified polypeptides, fragments, fusions, or epitopes thereof, or polypeptides expressed from their nucleic acid sequences, can be used. Using the purified NAMPT, NAMPT ligand polypeptides, or NAMPT receptor fragments, fusions, or epitopes thereof or proteins expressed from their nucleic acid sequences, antibodies can be prepared using any suitable methods known in the art.

The antibodies can be generated in cell culture, in phage, or in mammals such as mice, rabbits, sheep, and horses. Therefore, in some embodiments, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, Antibody Production: Essential Techniques (Wiley, 1997); Shephard, et al., Monoclonal Antibodies (Oxford University Press, 2000); Goding, Monoclonal Antibodies: Principles And Practice (Academic Press, 1993); Current Protocols In Immunology (John Wiley & Sons, most recent edition).

The antibodies can be modified by recombinant means to increase efficacy of the antibody in mediating the desired function. Antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., Mol. Immunol. 30:105-08 (1993). The modification in amino acids includes deletions, additions, substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to NAMPT or NAMPT ligand polypeptides, or fragments, or fusions thereof. See e.g., Antibody Engineering: A Practical Approach (Oxford University Press, 1996).

Suitable antibodies with the desired biologic activities can be identified by in vitro assays including but not limited to: proliferation, migration, adhesion, soft agar growth, angiogenesis, cell-cell communication, apoptosis, transport, signal transduction, and the following in vivo assays such as the inhibition of tumor growth.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

i. Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

Sometimes, CDR-grafting alone can lead to a reduction or complete loss of binding affinity, as a set of supporting framework residues in the Vernier zone are important for maintaining the conformation of the CDRs (Foote and Winter, *J. Mol. Bio.*, 224:487-499 (1992)). This problem can be addressed by reintroducing murine residues into the human framework (Queen, et al., *Proc. Natl. Acad. Sci. USA*, 86(24):10029-33 (1989)); such substitutions are commonly called back-mutations.

Most therapeutic proteins are, to a varying extent, immunogenic (Van Walle et al., *Expert Opin. Biol., Ther.*, 7:405-418 (2007), Stas et al., Cambridge University Press, Cambridge, (2009)) and even so called fully-human antibody therapeutics may contain immunogenic regions (Harding et al., *J. Chromatogr. B. Biomed. Sci. Appl.*, 752:233-245 (2001)). Immunogenicity is the ability to induce a Th (T-helper) response, which is triggered when a unique T-cell receptor recognizes a peptide bound to the HLA class II molecules displayed on antigen presenting cells. The peptides are generated from proteins internalized by the antigen presenting cell which are then processed through the endosomal cleavage pathway. Only peptides with sufficient affinity for the HLA class II molecules will be presented on the cell surface, and could possibly trigger a Th response.

Consequently, it is possible to lower the immunogenicity potential by removing Th epitopes, a process known as deimmunization (Chamberlain, *The Regulatory Review*, 5:4-9 (2002), Baker and Jones, *Curr. Opin. Drug. Discov. Devel.*, 10:219-227 (2007)). This is achieved by predicting which peptides in the therapeutic protein can bind to HLA class II molecules, and subsequently introducing substitutions that eliminate or reduce the peptide binding affinity for HLA class II molecules.

There are several HLA class II genes and almost all are highly polymorphic. Additionally, HLA class II molecules consist of an alpha and beta chain, each derived from a different gene which, with the inherent polymorphism, further increases variation. Every individual expresses the genes: DRA/DRB, DQA/DQB and DPA/DPB. Of these only DRA is non-polymorphic. In addition, a 'second' DRB gene (DRB3, DRB4 or DRB5) may also be present, the product of which also associates with the DRA chain.

The focus during a deimmunization is on the DR allotypes, which are known to express at a higher level than DQ and DP (Laupeze et al., *Hum. Immunol.,* 61:591-97 (1999), Gansbacher and Zier, *Cell Immunol.,* 117:22-34 (1988), Berdoz, et al., *J. Immunol.,* 139:1336-1341 (1987), Stunz et al., "HLA-DRB1 abd-DRB4 genes are differentially regulated at the transcriptional level, *J. Immunol.,* 143:3081-3086 (1989)). The assessment of severity for individual epitopes is based on the criteria of promiscuity, i.e., the number of HLA allotypes a specific epitope binds to, as well as the importance (frequency) of the allotypes in the population and a qualitative assessment of the HLA:peptide complex binding strength. As the T-cell population of an individual has been selected to not recognize "self-peptides" it is possible to screen the protein that is being deimmunized for peptides that correspond to (known) self-peptides which should not normally induce a Th response.

Because an important property of a therapeutic antibody is the binding activity, it is important that substitutions proposed during the humanization and deimmunization do not substantially affect the affinity or stability of the antibody. A large amount of information has been collected in the last 20 years on humanization and grafting of the CDRs (Jones et al., *Nature,* 321, 522-525 (1986), Foote and Winter, *J. Mol. Bio.,* 224:487-499 (1992)), the biophysical properties of antibodies (Ewert et al., *J. Mol. Biol.,* 325:531-553 (2003)), the conformation of the CDR-loops (Chothia and Lesk, *J. Mol. Biol.,* 196:901-917 (1987), Al-Lazikani, et al., *J. Mol. Biol.,* 273:927-948 (1997), North, et al., *J. Mol. Biol.,* 406:228-256 (2011)) and for the frameworks (Vargas-Madrazo and Paz-Garcia, *J. Mol. Recognit.,* 16:113-120 (2003), Honegger, et al., *Protein Eng. Des. Sel.,* 22:121-134 (2009)), which along with advances in protein modeling (Desmet, et al., *Proteins,* 48:31-43 (2002), Almagro, et al., *Proteins,* 79:3050-3066 (2011)) makes it possible to accurately humanize and deimmunize antibodies with substantially retained binding affinity and stability.

For example, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

ii. Single-Chain Antibodies

Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

iii. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

iv. Hybrid Antibodies

The antibody can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., a bivalent antibody has the ability to bind at least two different epitopes simultaneously. Such hybrids can be formed by fusion of hybridomas producing the respective component antibodies, or by recombinant techniques. Such hybrids may, of course, also be formed using chimeric chains.

v. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, Calif.). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin, or diphtheria toxin.

vi. Method of Making Antibodies Using Protein Chemistry

One method of producing proteins such as antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or anitgen binding fragment thereof via similar peptide condensation reactions. For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

2. Functional Nucleic Acids

Functional nucleic acids that inhibit the transcription, translation or function of the NAMPT gene are disclosed. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of the NAMPT gene or they can interact with the NAMPT polypeptide itself. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore the disclosed compositions can include one or more functional nucleic acids designed to reduce expression or function of the NAMPT enzyme.

In some embodiments, the composition includes a functional nucleic acid or polypeptide designed to target and reduce or inhibit expression or translation of NAMPT mRNA; or to reduce or inhibit expression, reduce activity, or increase degradation of NAMPT enzyme. In some embodiments, the composition includes a vector suitable for in vivo expression of the functional nucleic acid.

In some embodiments, a functional nucleic acid or polypeptide is designed to target a segment of the nucleic acid encoding the amino acid sequence of SEQ ID NO: 2, or the complement thereof, or variants thereof having a nucleic acid sequence 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to a nucleic acid encoding the amino acid sequence of SEQ ID NO: 2.

In other embodiments, a functional nucleic acid or polypeptide is designed to target a segment of the nucleic acid sequence of SEQ ID NO: 1, or the complement thereof, or variants thereof having a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1

In some embodiments, the function nucleic acid hybridizes to the nucleic acid of SEQ ID NO: 1, or a complement thereof, for example, under stringent conditions. In some embodiments, the function nucleic acid hybridizes to a nucleic acid sequence that encodes SEQ ID NO: 2, or a complement thereof, for example, under stringent conditions.

Methods of making and using vectors for in vivo expression of the disclosed functional nucleic acids such as antisense oligonucleotides, siRNA, shRNA, miRNA, EGSs, ribozymes, and aptamers are known in the art.

i. Antisense Molecules

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the NAMPT target molecule with a dissociation constant ($K_d$) less than or equal to $10^{-6}$, $10^{-8}$, $10^{-10}$, or $10^{-12}$.

ii. Aptamers

The functional nucleic acids can be aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophylline, as well as large molecules, such as reverse transcriptase and thrombin. Aptamers can bind very tightly with $K_d$'s from the target molecule of less than $10^{-12}$ M. It is preferred that the aptamers bind the NAMPT target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the NAMPT target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

iii. Ribozymes

The functional nucleic acids can be ribozymes. Ribozymes are nucleic acid molecules that are capable of catalyzing a chemical reaction, either intra-molecularly or inter-molecularly. It is preferred that the ribozymes catalyze intermolecular reactions. Different types of ribozymes that catalyze nuclease or nucleic acid polymerase-type reactions which are based on ribozymes found in natural systems, such as hammerhead ribozymes are disclosed. Ribozymes that are not found in natural systems, but which have been engineered to catalyze specific reactions de novo are also disclosed. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for targeting specific cleavage of nucleic acids because recognition of the target substrate is based on the target substrates sequence.

iv. Triplex Forming Oligonucleotides

The functional nucleic acids can be triplex forming oligonucleotide molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

v. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

vi. RNA Interference

In some embodiments, the functional nucleic acids induce gene silencing through RNA interference (siRNA). Expression of the NAMPT gene can be effectively silenced in a highly specific manner through RNA interference.

Gene silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme called Dicer, into double stranded small interfering RNAs (siRNA) 21-23 nucleotides in length that contain 2 nucleotide overhangs on the 3' ends (Elbashir, et al., *Genes Dev.,* 15:188-200 (2001); Bernstein, et al., *Nature,* 409:363-6 (2001); Hammond, et al., *Nature,* 404:293-6 (2000); Nykanen, et al., *Cell,* 107: 309-21 (2001); Martinez, et al., *Cell,* 110:563-74 (2002)). The effect of iRNA or siRNA or their use is not limited to any type of mechanism.

In one embodiment, a siRNA triggers the specific degradation of homologous NAMPT RNA molecules, such as NAMPT mRNAs, within the region of sequence identity between both the siRNA and the target NAMPT RNA.

Sequence specific gene silencing can be achieved in mammalian cells using synthetic, short double-stranded RNAs that mimic the siRNAs produced by the enzyme dicer (Elbashir, et al., *Nature,* 411:494-498 (2001)) (Ui-Tei, et al., *FEBS Lett,* 479:79-82 (2000)).

siRNA can be chemically or in vitro-synthesized or can be the result of short double-stranded hairpin-like RNAs (shRNAs) that are processed into siRNAs inside the cell. For example, WO 02/44321 discloses siRNAs capable of sequence-specific degradation of target mRNAs when base-paired with 3' overhanging ends, herein incorporated by reference for the method of making these siRNAs. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. In some embodiments, the composition includes a vector expressing the functional nucleic acid. The production of siRNA from a vector is more commonly done through the transcription of a short hairpin RNAse (shRNAs). Kits for the production of vectors including shRNA are available, such as, for example, Imgenex's GENESUPPRESSOR™ Construction Kits and Invitrogen's BLOCK-IT™ inducible RNAi plasmid and lentivirus vectors. In some embodiments, the functional nucleic acid is siRNA, shRNA, or miRNA.

3. Small Molecule Inhibitors of NAMPT

Small molecules that specifically inhibit the transcription, translation or function of the NAMPT gene and/or gene product are described. Small molecule inhibitors of NAMPT are molecules that have a specific function, such as binding a target molecule or reducing, preventing or otherwise moderating a specific reaction or interaction. As discussed in more detail below, The term "small molecules" generally includes a molecule of less than 10,000 Da in molecular weight. Small molecules that specifically interact with NAMPT or NAMPT receptors can act as effectors, inhibitors, modulators, and stimulators of a specific activity possessed by a target molecule, or the small molecules can possess a de novo activity independent of any other molecules. Preferred small molecule inhibitors of NAMPT have excellent dose-dependent enzyme inhibitory properties. Exemplary small molecule inhibitors of NAMPT include the NAMPT enzymatic inhibitors FK-866, and FK-866 analogues MS-1-82, Rari049, and Alp-135 (see FIGS. 9A-9E).

a. FK-866

FORMULA I: FK-866

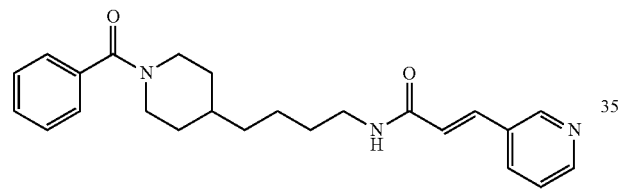

FK-866 ((E)-N-[4-(1-Benzoylpiperidin-4-yl)butyl]-3-pyridin-3-ylprop-2-enamide) is a potent, selective, non-competitive NAMPT inhibitor. which inhibits NAMPT enzymatic activity. FK-866 (formula C24H29N3O2; CAS Number658084-64-1) is available from multiple commercial sources (e.g., Abcam catalog No. ab142148).

b. Analogs of FK-866

To generate functional analogs of the NAMPT inhibitor FK-866, the FK-866 structure was divided into three regions and varied by replacing with N-heterocycles to generate FK866 analogs. Three analogs of FK866 include MS-1-83, RARI-049, and ALP-135. Preliminary studies in MCT-PH show that these inhibitors have promise as a preventive therapy reducing both right ventricular systolic pressure (RVSP), and hypertrophy-ratio of RV and LV plus septal-S weight (RVH-RV).

FORMULA II: MS-1-82

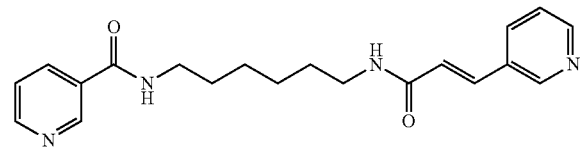

FORMULA III: RARI-049

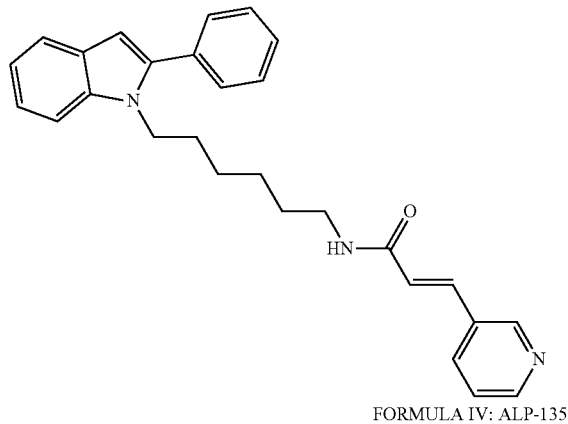

FORMULA IV: ALP-135

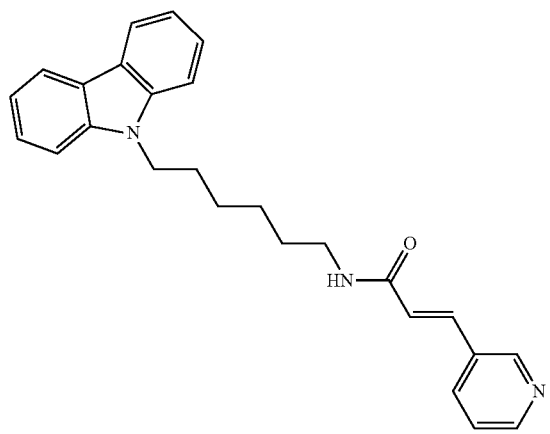

C. Excipients, Delivery Vehicles and Devices

NAMPT inhibitors can be administered with or without the aid of a delivery vehicle. Appropriate delivery vehicles for the inhibitors are known in the art and can be selected to suit the particular inhibitor. In a preferred embodiment, the inhibitor is delivered by intravenous injection or orally. Typical carriers are saline, phosphate buffered saline, and other injectable carriers.

The NAMPT inhibitors can be formulated into pharmaceutical compositions including one or more pharmaceutically acceptable carriers. The formulation may also be in the form of a suspension or emulsion, and optionally include pharmaceutically acceptable diluents, preservatives, solubilizers, emulsifiers, adjuvants and/or carriers. Such compositions include the diluents sterile water, buffered saline of various buffer content (e.g., Tris-HCl, acetate, phosphate), pH and ionic strength and optionally additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

The antibodies, proteins having the binding properties of antibodies, nucleic acids, or small molecules are administered to a subject in an amount effective to treat diseases and disorders in which NAMPT activity is detrimental to the subject. The antibodies are administered with or without one or more additional therapeutic agents. Kits containing a pharmaceutical composition and instructions for dosing, and preloaded syringes containing pharmaceutical compositions are also described.

III. Methods of Use

Methods of using the NAMPT inhibitors include systemically administering to a subject an effective amount of a composition including one or more NAMPT inhibitors to prevent, reduce, or inhibit the expression or function of NAMPT in the subject with an effective amount of a composition including a NAMPT inhibitor to prevent, reduce, or inhibit vascular inflammation and remodeling and PAH the subject; or a combination thereof.

Antibodies, proteins having the binding properties of antibodies, nucleic acids, or small molecules are administered to a subject in an amount effective to treat diseases and disorders in which NAMPT activity is detrimental to the subject. The antibodies are administered with or without one or more additional therapeutic agents. Methods for the repeated dosing regimens for using antibodies specific for NAMPT to treat PAH are provided. Daily, weekly, bi-weekly and monthly dosing regimens are described. In a preferred embodiment, antibodies, F(Ab)s or F(Ab)2's are administered via infusion and dosing is repeated on a monthly basis. Monthly dosing has many advantages over weekly dosing including a lower number of total injections, decreased number of injection site reactions (e.g., local pain and swelling), increased patient compliance (i.e., due to less frequent injections), and less cost to the patient as well as the health care provider.

The methods include utilizing a combination therapy wherein human antibodies are administered to a subject with another therapeutic agent, such as one or more additional antibodies that bind other targets (e.g., antibodies that bind NAMPT, one or more receptors of NAMPT, one or more cytokines, soluble NAMPT receptor (e.g., soluble TLR-4) and/or one or more chemical agents that inhibit NAMPT production or activity (such as small molecule inhibitors of NAMPT), or another vasoactive drug.

A. Methods of Treatment

NAMPT inhibition has therapeutic effects in pulmonary hypertension by reducing vascular inflammation and reversing pulmonary vascular remodeling characterized by medial hypertrophy and neointima formation. Methods of reducing, prevented or reversing vascular remodeling by administration of one or more inhibitors of NAMPT are described. In some embodiments, methods of treating disorders in which NAMPT activity is detrimental include parenteral administration of human antibodies, preferably recombinant human monoclonal antibodies, or antigen binding fragments thereof, that specifically bind to human NAMPT, or one or more specific ligands of NAMPT.

In preferred embodiments, one or more NAMPT inhibitors are effective to reduce, inhibit, or delay one or more symptoms of a disease, disorder or condition associated with the thickening and rigidifying of blood vessels in a human patient.

Methods of using NAMPT inhibitors including, but not limited to, methods designed to inhibit or block transcription, translation, or function of the NAMPT enzyme can be used to modulate cellular functions and prevent, reduce or reverse undesirable vascular remodeling.

B. Treatment of PAH

Methods of using NAMPT inhibitors for treating PAH and are provided.

Pulmonary hypertension (PH) is an elevation in the pressure in the arteries of the lungs. The clinical classification system for PH includes five distinct "Groups" (*J Am Coll Cardiol.* 54:S1-117 (2009); *J Am Coll Cardiol.* 54:S43-54 (2009)) including a very broad spectrum of disease etiology and pathobiology affecting not only the lungs and right ventricle directly, but also secondarily through other organ pathologies.

Group I is pulmonary artery hypertension (PAH). Group II is PH associated with left heart disease. Group III is PH associated with lung disease and/or hypoxia. Group IV is PH associated with chronic thromboembolic disease, and Group V is PH associated with multifactorial mechanisms. Within each classification groups I-IV, there are distinct mechanistic programs that contribute to PH, either on the arterial or venous side of the pulmonary circulation.

The methods can treat pulmonary hypertension (PH) classified into any one of the five clinically-recognized groups.

Pulmonary arterial hypertension (PAH) is a specific subgroup of pulmonary hypertension (PH), characterized by high blood pressure (hypertension) of the main artery of the lungs (pulmonary artery) for no apparent reason (idiopathic). PAH is a rare, progressive disorder with an estimated prevalence of 15 to 50 cases per 1 million people, usually affecting women between the ages of 20-50.

Pulmonary arterial hypertension (PAH) is a currently fatal condition in which pulmonary vascular inflammation and remodeling leads to elevated pulmonary arterial pressure, right ventricular (RV) hypertrophy (RVH), and, ultimately, RV dysfunction and failure. Vascular remodeling can lead to thickening of the interior of blood vessels, leading to the onset and progression of PAH.

The described compositions and devices can be administered to a subject to reduce or inhibit smooth muscle cell proliferation, migration, and a combination thereof in an amount effective to reduce or vascular remodeling and thereby treat or prevent PAH and other vascular disorders in the subject. In some embodiments, the patency of vessels that have been thickened and rigidified by vascular remodeling can be increased using a composition containing a NAMPT inhibitor. Therefore, methods for administering a composition containing a NAMPT inhibitor to the subject prior to or after a vascular injury, surgery or trauma to prevent, reduce or reverse vascular changes due to vascular remodeling in a subject in need thereof are provided.

i. Symptoms of PAH

The clinical symptoms and developmental stages of PAH can be categorized by a clinician to determine disease progression, into one of four classes, including Class I (no symptoms with normal activity); Class II (symptoms at rest, but symptoms such as fatigue, shortness of breath or chest pain with normal activity); Class III (comfortable at rest, but have symptoms whenever physically active); or Class IV (symptoms with physical activity and while at rest).

In some embodiments, one or more inhibitors of NAMPT are administered to treat PAH following open-heart surgery, such as Atrial septostomy surgery (creating an opening between the upper left and right chambers of the heart (atria) to relieve the pressure on the right side of the heart). In other embodiments, one or more inhibitors of NAMPT are administered to treat PAH associated with a lung or heart-lung transplant. A surgeon can apply one or more NAMPT inhibitors to the surgical site at the time of surgery, prior to surgery or following surgery, to enhance the process of wound healing, or to prevent the development of vascular disorders, such as those that give rise to PH or PAH.

Clinical signs of PAH indicative of a need for treatment include any one or more of dyspnea, fatigue, and chest pain. Any of these symptoms can be present only with exertion, or both with exertion and at rest. Additional symptoms include syncope, edema and swelling, dizziness, poor or reduced oral intake, as well as any of the signs and symptoms of right heart failure, increased or faster than normal heart rate and palpitations.

Signs of the improvement in PAH, for example, in response to treatment with one or more inhibitors of NAMPT, include an improvement in any one or more of the above symptoms, and changes in the hemodynamics (reducing PVR, increasing Cardiac Index, etc.).

Criteria constituting treatment failure in PAH include any worsening/no change of the above symptoms, side effects such as issues with toxicity/tolerability/drug-drug interactions with drugs patient already taking, infections due to administration issues, worse/no change in the hemodynamics (increasing PVR, reducing Cardiac Index, etc.), no change or further deterioration in right-ventricle (RV) structure/function, worsening or no change in an observable factor such as 6 minute walk distance, and worsening or no change in cardiopulmonary test results (e.g., worsening oxygen consumption).

Early pharmacological intervention can slow or preclude the onset and development of chronic PAH. For example, compositions of NAMPT inhibitors can reduce or prevent vascular remodeling, but allow normal, healthy vascular neo-tissue growth to occur.

ii. Animal Models for PAH

No single preclinical model could be generated that would serve as an excellent surrogate to study the pathogenesis of PAH, with the possible exception of high altitude PH modeled by chronic exposure to hypobaric hypoxia. Currently, no animal models exists that recapitulate specific pathologies in ways that mirror the classification system for human PH. Experimental models for PAH use test animals such as mice and rats, which have different lung and heart structure/function from humans. Perhaps more importantly, the three most widely-recognized rodent models (MCT, Chronic hypoxia and Sugen/hypoxia models (see Colvin and Yeager, *J Pulm Respir Med.* 4(4): 198, (2014), which is incorporated by reference in its entirety) do not mimic the human condition. For example, the MCT model is based on a toxin, and has little relevance for disease etiology in humans (e.g., the MCT model does not induce many plexiform lesions seen in PAH). The chronic hypoxia model does not induce Group I PH (PAH), nor does it lead to plexiform lesions seen in PAH. The Sugen 5416/hyoxia mouse model of PH (Vitali, et al., *Pulm. Circ.* 4(4): 619-629 (2014)) is a VEGFR-2 and PDGFR inhibitor which can only induce PAH with hypoxia. This model also has little or no patient relevance for disease etiology, and does not result in equivalent right ventricle (RV) failure as is seen in patients with Group 1 PH (PAH). Although nearly all of these models can induce PAH in days to weeks, the models do not mimic the time course of the human condition. Furthermore, doses and tissue delivery of potential therapies, etc. do not equate accurately from animals to humans, and are not considered predictive of successful treatment regimens in human patients.

However, notwithstanding the problems with animal models, data acquired in these systems can provide a guide for the kind of measurements that are required to provide meaningful data in human studies, and can also provide important safety data, especially regarding identification of overt side effects and toxicity.

C. Controls

The effect of a NAMPT inhibitor can be compared to a control. Suitable controls are known in the art and include, for example, untreated cells or an untreated human subject. In some embodiments, the control is untreated tissue from the subject that is treated, or from an untreated subject. Preferably the cells or tissue of the control are derived from the same tissue as the treated cells or tissue. In some embodiments, an untreated control subject suffers from the same disease or condition as the treated subject. For example, in some embodiments, one or more of the pharmacological or physiological markers or pathways affected by anti-NAMPT treatment is compared to the same pharmacological or physiological marker or pathway in untreated control cells or untreated control subjects. For example, anti-NAMPT treated subjects can be compared to subjects treated with other inhibitors of PAH, such as blood vessel dilators (vasodilators), endothelin receptor antagonists, phosphodiesterase inhibitors such as sildenafil and tadalafil, high-dose calcium channel blockers, anticoagulants, digoxin, diuretics, or oxygen.

The subjects treated with other inhibitors of PAH can have a greater incidence of in post-operative PAH, or a reduced reduction of tissue affected by vascular remodeling than do subjects treated with the NAMPT inhibitors.

D. Dosages and Effective Amounts for Treating PAH

In some in vivo approaches, the compositions of NAMPT inhibitors are administered to a subject in a therapeutically effective amount for treatment of one or more of the signs or symptoms of PAH.

The term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, race, genetics etc.), the disease or disorder, and the treatment being effected.

For all of the disclosed compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, for intravenous injection or infusion, dosage may be between 10 and 400 mg. Preferably, the compositions are formulated to achieve a NAMPT inhibitor serum level of between approximately 1 and 1,000 μM.

Pharmaceutical compositions of NAMPT inhibitors are useful for the modulation of cellular processes that contribute to onset and progression of PAH, including vascular inflammation and remodeling. Exemplary cellular processes associated with vascular remodeling include endothelial cell (EC) and smooth muscle cell (SMC) apoptosis, SMC activation and proliferation, and EC to mesenchymal cell transition (EndMT). In some embodiments the compositions reduce or prevent the expression and/or function of the NAMPT enzyme and/or its interaction with its receptors, such as Toll-like Receptor-4 (TLR4). Therefore, compositions and methods for treatment of PAH include compositions and methods that prevent, reduce or otherwise disrupt the physiological interaction between TLR4 and NAMPT (NAMPT/TLR4). Typically, inhibitors of NAMPT/TLR4 are administered in an amount effective to reduce or prevent one or more of the downstream cellular processes associated with the pathophysiological NAMPT/TLR4 interaction. Therefore, methods of reducing or preventing NAMPT/TLR4-mediated activation of NFκB transcriptional activities to treat PAH in a subject are also provided. In preferred embodiments, the amount of one or more NAMPT inhibitors does not prevent or reduce normal, healthy vascular neotissue formation in the subject.

1. Target-Specific Effects

In some embodiments, the NAMPT inhibitors are effective to prevent the biological activities of smooth muscle cells, such as proliferation and activation. In some embodiments, one or more inhibitors can be in an amount effective to increase or stimulate the process of apoptosis in a cell.

In one embodiment the one or more NAMPT inhibitors are in an amount effective to prevent or reduce vascular inflammation and remodeling in a subject. In a preferred embodiment the amount of one or more NAMPT inhibitors does not prevent wound healing or the formation of normal, health vascular neotissue in a subject compared to an untreated control. In another embodiment, the one or more NAMPT inhibitors are in an amount effective to decrease the amount of blood vessel growth at the site of an injury or surgery, to reverse or prevent the deposition of high density cellular and connective tissue that is associated with vascular remodeling. Typically, one or more NAMPT inhibitors are administered to a subject in an amount effective to decrease the amount of soluble extracellular NAMPT in the subject. Accordingly, one or more NAMPT inhibitors can be effective to reduce or prevent one or more biological activities that occur as a result of extracellular NAMPT, or as a result of downstream signaling events controlled by extracellular NAMPT. For example, by reducing or preventing the interaction between extracellular NAMPT and TLR4, NAMPT inhibitors can reduce or prevent TLR4-mediated induction of several signaling pathways controlling cellular activities including cellular proliferation, activation, chemotaxis and actin reorganization. Preferably the amount of one or more NAMPT inhibitors does not prevent the desirable healthy tissue remodeling that occurs as a component of healthy wound healing and tissue regeneration.

Inhibitors of NAMPT can be administered in an amount effective to reduce, prevent or otherwise or modify the amount, expression or functions of the NAMPT gene or NAMPT protein, or one or more receptors of NAMPT. Therefore, in some embodiments, the inhibitors can be administered in an amount effective to reduce one or more of the transcription factors that regulate transcription of NAMPT, such as HIF-1α, HIF-2α, STAT5 and proline hydroxylase-2 (PHD2).

In the case of chronic PAH, the process of vascular remodeling is unnecessary and undesirable, thus, preventing vascular inflammation and remodeling is not detrimental. Therefore, inhibitors of NAMPT can be administered in an amount effective to reduce one or more of the molecular events that give rise to vascular inflammation and remodeling in a subject. For example, the inhibitors can be effective to reduce smooth muscle cell (SMC) proliferation, SMC contraction, SMC activation, resistance of SMC to apoptosis, resistance of lung endothelial cell apoptosis, reduce endothelial cell to mesenchymal cell transition (EndMT), increase expression of EC markers such as PACAM1, reduce expression of mesenchymal cell markers such as Snai1 and Snai2, reduce expression of store-operated Ca2+ entry (SOCE)-related proteins, such as stromal interaction molecule 2 (STIM2) and release-activated Ca2+ modulator 2 (Orai2), and combinations thereof.

Inhibitors of NAMPT can be administered in an amount effective to enhance pulmonary compliance in a subject with PAH.

Pulmonary compliance is a measure of arterial distensibility and, either alone or in combination with pulmonary vascular resistance (PVR), gives clinicians the possibility of a good prognostic stratification of patients with pulmonary hypertension (see Ghio, et al., Glob Cardiol Sci Pract. 2015; (4): 58. (2015)). Measurement of pulmonary arterial compliance is often included in the routine clinical evaluation of such patients. Direct measurements of pulmonary vascular stiffness can be obtained in vivo quantifying arterial diameter as a function of pressure and generating pressure-diameter curves (the stiffer the vessel, the steeper the slope of the curves). The simple hemodynamic measurements obtained during routine right heart catheterization allow calculation of the compliance of the entire pulmonary circulation—that is the capacity of all arteries and arterioles to accumulate blood in systole and release it in diastole. In some embodiments, Inhibitors of NAMPT are administered in an amount effective to reduce, prevent or otherwise moderate one or more physiological effects of pulmonary hypertension. For example, in some embodiments, the inhibitors can be administered in an amount effective to reduce pulmonary vascular resistance, reduce RV stroke work index, reduce muscularization (i.e., reduce smooth muscle cell burden and/or prevent muscularization of normally non-muscularized arterioles), enhance vessel patency, increase PA compliance, increase elastance (i.e., the tendency of a vessel to recoil toward its original dimensions upon removal of a distending or compressing force).

The desired effect can be achieved over a time period consistent with the stage and severity of the disease. For example, any one or more of the effects can be observed in a subject following administration after a period of one hour, one day, one week, one month or more than one month.

2. Therapeutically or Prophylactic Amounts

The range for a therapeutically or prophylactically effective amount of an inhibitor of NAMPT can vary according to one or more of the type of inhibitor, the mechanism of action, the route of administration, the type and severity of the condition to be alleviated, and physiological parameters relating to the recipient, such as age, weight, etc.

An exemplary, non-limiting range for a therapeutically or prophylactically effective amount of an antibody or antibody binding fragment is between about 10 mg and 200 mg, inclusive, more preferably between about 20 mg and 100 mg and most preferably about 40 mg. It is to be noted that dosage values may vary with the type and severity of the condition to be alleviated.

In some embodiments, one or more antibody or antigen binding fragments thereof inhibitors of NAMPT or NAMPT receptors is administered via intravenous infusion to a human subject diagnosed with PAH to treat one or more of the signs or symptoms of chronic PAH. In some embodiments, one or more antibody or antigen binding fragments thereof inhibitors of NAMPT or NAMPT ligands is administered via endotracheal administration in an amount between 10 mg and 400 mg body weight, inclusive, to treat one or more of the signs or symptoms of chronic PAH.

In some embodiments, one or more small molecule inhibitors of NAMPT are administered to a human subject diagnosed with PAH, via oral administration, or via intravenous infusion in an amount between 0.1 and 3 mg/kg body weight, inclusive, for example, 10 µg/kg, 100 µg/kg, or 1 mg/kg body weight. The one or more small molecule inhibitors of NAMPT can be administered alone, or contained within liposomes. Oral administration of small molecule inhibitors of NAMPT can be repeated daily or weekly.

In some embodiments, one or more cell-permeable inhibitors of signal transducer and activator of transcription (STAT5), such as nicotinoyl hydrazine, SPI, or pimozide are administered to a human subject diagnosed with PAH intravenous infusion in an amount between 10 µg/kg and 3.5 mg/kg recipient, inclusive. The one or more inhibitors of STAT5 can be administered alone, or contained within liposomes.

In some embodiments, one or more inhibitors of the NAMPT receptor, such as TLR4, are administered to a human subject diagnosed with PAH, or at risk of PAH. An exemplary agent is Lipopolysaccharide from the photosynthetic bacterium *Rhodobacter sphaeroides* (LPS-RS), which is a potent antagonist of lipopolysaccharide (LPS) from pathogenic bacteria. For example, in some embodiments, LPS-RS is administered to a subject with PAH or at risk of PAH in an amount between 1 mg and 400 mg per day.

3. Timing of Administration and Dosage Regimens

The disclosed NAMPT inhibitors can be administered during a period during, or after onset of disease symptoms, or any combination of periods during or after diagnosis of one or more disease symptoms. For example, the subject can be administered one or more doses of the composition every 1, 2, 3, 4, 5, 6, 7, 14, 21, 28, 35, or 48 days after the onset or diagnosis of disease symptoms. In some embodiments, the multiple doses of the compositions are administered before an improvement in disease condition is evident. For example, in some embodiments, the subject receives 1, 2, 3, 4, 5, 6 7, 14, 21, 28, 35, or 48, over a period of 1, 2, 3, 4, 5, 6 7, 14, 21, 28, 35, or 48 days or weeks before an improvement in the disease or condition is evident.

Thus, compositions including one or more NAMPT inhibitors can be administered at different times in relation to a diagnosis, prognosis, surgery or injury depending on the disease or disorder to be treated. The timing of commencement of anti-NAMPT therapy should be determined based upon the needs of the subject, and can vary from at the time of diagnosis, time of injury, to one or more days, weeks or months after diagnosis, or injury. Methods for using formulations for delayed release of NAMPT inhibitors are provided. In some embodiments, therapy using inhibitors of NAMPT can be discontinued once physiological signs of vascular remodeling, or symptoms or PAH have abated, but may be needed foe extended durations.

It may be that PAH is associated with an underlying vascular disease, autoimmune disease such as scleroderma and systemic lupus, fibrotic lung disorder (COPD, sarcoidosis, IPF), drug toxicity such as fenfluramine exposure, or is associated with an injury. In the case of injury involving the lungs, the NAMPT inhibitors can be administered immediately, as well as subsequently throughout the healing and regeneration of the lung tissue/vascular surface.

In some embodiments, the subject is a patient in intensive care. In the intensive care setting, the compositions including one or more NAMPT inhibitors can be administered over the course of an hour, for example, as a rescue therapy or salvage therapy. Administration may be repeated hourly, daily, weekly, or monthly, as required. In a particular embodiment, the inhibitors are delivered to the patient via intravenous infusion over the course of one hour.

4. Routes of Administration

Parenteral administration of the composition, if used, is generally characterized by injection. Injectable formulations can be prepared in conventional forms, either as liquid solutions or suspensions, solid forms suitable for solution of suspension in liquid prior to injection, or as emulsions. Administration involving use of a slow release or sustained release system, such that a constant dosage is maintained, is also discussed.

In some embodiments a single dose of one or more inhibitors of NAMPT is delivered to a subject as one or more doses to raise the blood concentration of the one or more inhibitors to a desired level. The dose can be given by any appropriate means, such as via injection or infusion. The repeating regimen of the dose can be varied depending upon the desired effect and the symptoms of the subject to be treated. Thus, the desired blood concentration of one or more NAMPT inhibitors can be maintained for a desired period of time.

Pharmaceutical compositions including one or more NAMPT inhibitors can be administered in a variety of manners. For example, the compositions of antibodies or fragments thereof can be administered via intravenous infusion (i.v.), intraperitoneally (i.p.), intramuscularly (i.m.), subcutaneously (s.c.), or by endotracheal (i.t.) delivery. In some preferred embodiments, antibodies and antigen binding fragments thereof are delivered to a subject by intravenous infusion (i.v.). The compositions may be administered parenterally (e.g., i.v. infusion), by injection, or by other means appropriate to a specific dosage form, e.g., including administration by inhalation of a lyophilized powder. In other embodiments, small molecule inhibitors are administered orally. In some embodiments, oral administration of small molecules can be repeated daily, or weekly. In some embodiments, intravenous infusion of antibodies or fragments thereof is repeated monthly.

Any of the provided inhibitors can be administered without conjugation, or as ACE antibody-conjugated liposomes.

The rate of release of the inhibitor(s) may be controlled by a number of methods including varying one or more of the ratio of the absorbable material to the agent, the molecular weight of: the absorbable material, the composition of the inhibitor(s), the composition of the absorbable polymer, the coating thickness, the number of coating layers and their relative thicknesses, the inhibitor concentration, and/or physical or chemical binding or linking of the inhibitor(s) to the device or sealing material. Top coats of polymers and other materials, including absorbable polymers may also be applied to control the rate of release of the one or more inhibitors.

E. Combination Therapies

The disclosed compositions and devices including NAMPT inhibitors can be administered alone, or in combination with one or more additional active agent(s), as part of a therapeutic or prophylactic treatment regime.

The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). For example, one or more NAMPT inhibitors can be administered on the same day, or a different day than the second active agent. In some embodiments, the second active agent can be administered on the first, second, third, or fourth day, following or before one or more inhibitors of NAMPT.

A non-limiting list of exemplary additional therapeutic agents includes vasoactive agents, such as catecholamines (e.g., adrenaline, noradrenaline, dopamine, dobutamine, isoprenaline, dopexamine), phosphodiesterase inhibitors (e.g., sildenafil, milrinone, amrinone, levosimendan), calcium sensitizers (e.g., levosimendan, glucagon), vasopressors (phenylephrine, metaraminol, ephedrine, vasopressin, steroids), digoxin Ca2+, thyroid hormone, epinephrine and methylene blue.

In some embodiments, the additional therapeutic agent is a blood vessel dilator (vasodilator) such as epoprostenol (FLOLAN®, VELETRI®). The drawback to epoprostenol is that its effects last only a few minutes. Epoprostenol is continuously injected through an intravenous (IV) catheter, for example via a small pump. Potential side effects of epoprostenol include jaw pain, nausea, diarrhea and leg cramps, as well as pain and infection at the IV site. In other embodiments, the additional therapeutic agent is iloprost (VENTAVIS®). Iloprost is inhaled six to nine times a day through a nebulizer. Because it's inhaled, it goes directly to the lungs. Side effects associated with iloprost include chest pain, often accompanied by a headache and nausea, and breathlessness. In other embodiments, the additional therapeutic agent is Treprostinil (TYVASO®, REMODULIN®, ORENITRAM®). Treprostinil is administered by injection, inhaled or taken orally up to four times a day. It can cause side effects such as a headache, nausea and diarrhea. In other embodiments, the additional therapeutic agent is Oral Uptravi (SELEXIPAG®).

In some embodiments, the additional therapeutic agent is a Endothelin receptor antagonist, such as bosentan (TRACLEER®), macitentan (OPSUMIT®), and ambrisentan (LETAIRIS®).

In some embodiments, the additional therapeutic agent is sildenafil (REVATIO®, VIAGRA®) or tadalafil (CIALIS®, ADCIRCA®). These drugs work by opening the blood vessels in the lungs to allow blood to flow through more easily. Side effects can include an upset stomach, headache and vision problems.

In some embodiments, the additional therapeutic agent is a high-dose calcium channel blocker, such as amlodipine (NORVASC®), diltiazem (CARDIZEM®, TIAZAC®) and nifedipine (PROCARDIA®). Although calcium channel blockers can be effective, only a small number of people with pulmonary hypertension respond to them.

In some embodiments, the additional therapeutic agent is a soluble guanylate cyclase (SGC) stimulator. Soluble guanylate cyclase (SGC) stimulators (ADEMPAS®) interact with nitric oxide and help relax the pulmonary arteries and lower the pressure within the arteries. These medications can sometimes cause dizziness or nausea.

In some embodiments, the additional therapeutic agent is an anticoagulant, such as warfarin (COUMADIN®, JANTOVEN®) to help prevent the formation of blood clots within the small pulmonary arteries. Because anticoagulants prevent normal blood coagulation, they increase risk of bleeding complications.

In some embodiments, the additional therapeutic agent is digoxin (LANOXIN®). Digoxin can help control heart rate and preclude arrhythmias.

In some embodiments, the additional therapeutic agent is a diuretic (commonly known as water pills), to help eliminate excess fluid from the body and reduce the amount of work the heart has to do. They may also be used to limit fluid buildup in the lungs.

In some embodiments, the additional therapeutic agent is oxygen. Some people who have pulmonary hypertension eventually require continuous oxygen therapy.

Additional classes of drugs that can be combined with one or more inhibitors of NAMPT, and/or inhibitors of NAMPT receptors include anti-neointima agents, chemotherapeutic agents, antibiotics, antivirals, steroidal and non-steroidal anti-inflammatories, conventional immunotherapeutic agents, immune-suppressants, cytokines, chemokines and/or growth factors, anti-proliferatives or anti-migration agents designed for treating or preventing PAH, agents which affect migration and extracellular matrix production, agents which affect platelet deposition or formation of thrombus, and agents that promote vascular healing and re-endothelialization.

Exemplary anti-proliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Exemplary agents modulating cell replication/proliferation include targets of rapamycin (TOR) inhibitors (including sirolimus, everolimus and ABT-578), paclitaxel and antineoplastic agents, including alkylating agents (e.g., cyclophosphamide, mechlorethamine, chlorambucil, melphalan, carmustine, lomustine, ifosfamide, procarbazine, dacarbazine, temozolomide, altretamine, cisplatin, carboplatin and oxaliplatin), antitumor antibiotics (e.g., bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (e.g., deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase), antimitotic agents (e.g., vincristine, vinblastine, vinorelbine, docetaxel, estramustine) and molecularly targeted agents (e.g., imatinib, tretinoin, bexarotene, bevacizumab, gemtuzumab ogomicin and denileukin diftitox).

Exemplary anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, abciximab, ticlopidine, clopidogrel, heparin.

The additional therapeutic agents can be administered locally or systemically to the subject, or coated or incorporated onto, or into a device or graft. The additional therapeutic reagents can be administered by the same, or by different routes and by different means. For example, one or more NAMPT inhibitors can be delivered via infusion with one or more of paclitaxel, taxotere and other taxoid compounds, methotrexate, anthracyclines such as doxorubicin, everolimus, serolimus, rapamycin or rapamycin derivatives delivered by different means.

F. Methods for Diagnostic and Prophylactic Treatment

Given their ability to bind to NAMPT, in some embodiments, inhibitors of NAMPT are useful to detect eNAMPT (e.g., in a biological sample, such as blood, serum or plasma), using a conventional immunoassay, such as an enzyme linked immunosorbent assays (ELISA), an radioimmunoassay (RIA) or tissue immunohistochemistry. Therefore, methods for detecting and/or quantitating the amount of NAMPT in a biological sample are provided. The methods include contacting a biological sample with one or more inhibitors of NAMPT and detecting either the inhibitor bound to NAMPT, or the unbound inhibitor, to detect and/or quantitate the NAMPT in the biological sample. In some embodiments, the NAMPT inhibitor is an antibody or fragment thereof. For example, the anti-NAMPT antibody is directly or indirectly labeled with a detectable substance to facilitate detection of the bound or unbound antibody. Suitable detectable substances include various enzymes, prosthetic groups, fluorescent materials, luminescent materials and radioactive materials. Alternative to labeling the inhibitor, NAMPT can be assayed in biological fluids by a competition immunoassay, for example, utilizing NAMPT standards labeled with a detectable substance and an unlabeled anti-NAMPT antibody. In this assay, the biological sample, the labeled NAMPT standards and the anti-NAMPT antibody are combined and the amount of labeled NAMPT standard bound to the unlabeled antibody is determined. The amount of NAMPT in the biological sample is inversely proportional to the amount of labeled NAMPT standard bound to the anti-NAMPT antibody.

Therefore, in some embodiments, the methods include the step of identifying a subject in need of anti-NAMPT treatment, for example, a subject at risk of a disease or disorder associated with detrimental NAMPT activity. An exemplary subject is a human at risk of PAH. The methods can include the step of assaying a biological fluid from the subject to determine the presence and/or quantity of NAMPT present in the sample, as compared to a normalized standard or control sample. An exemplary control sample includes a sample of equivalent biological fluid taken from a healthy individual.

The present invention will be further understood by reference to the following non-limiting examples.

EXAMPLES

Example 1: NAMPT-Mediated Contributions to PAH Vascular Remodeling

Materials and Methods
Animals.

Male mice (8-week old Nampt$^{-/-}$ mice in C57BL/6 background and their WT siblings) were exposed to hypoxia (10% $O_2$) in a ventilated chamber for four weeks. Right ventricular systolic pressure (RVSP) was determined by right heart catheterization using a Millar pressure transducer catheter. A weight ratio of the right ventricle divided by the sum of left ventricle and septum (RV/(LV+S)) was measured to determine the extent of right ventricular hypertrophy (RVH). Pulmonary artery remodeling was assessed using Aperio ImageScope software (version 11) after lungs were stained with hematoxylin and eosin. A minimum of 10 microscopic fields were examined for each slide. Approximately twenty muscular arteries with diameters (D) 50-100 µm or D<50 µm per lung section were outlined and measured. Vessel remodeling was calculated as ((external vessel area−internal vessel area)/external vessel area), as previously described (67).

Cell Proliferation Assays.

Cell proliferation was determined using either a 5-bromo-2'-deoxyuridine (BrdU) incorporation assay or cell counting. BrdU assays (QIA58, Calbiochem, San Diego, Calif.) were performed in a 96-well format according to manufacturer's instructions, using starting cell densities of 4000 cells/well. For cell counting, cells were trypsinized and resuspended after experimental procedures; densities were counted with a TC10™ automated cell counter (Bio-Rad). FBS or PDGF was used as positive controls.

Human Plasma NAMPT Measurements by ELISA.

Approval for the collection of human plasma was granted by Institutional Review Boards of participating centers. Plasma samples were obtained from patients with PAH defined by the 2013 Nice classification and controls. NAMPT plasma levels were obtained using an ELISA as we previously described.

Figure 2A:
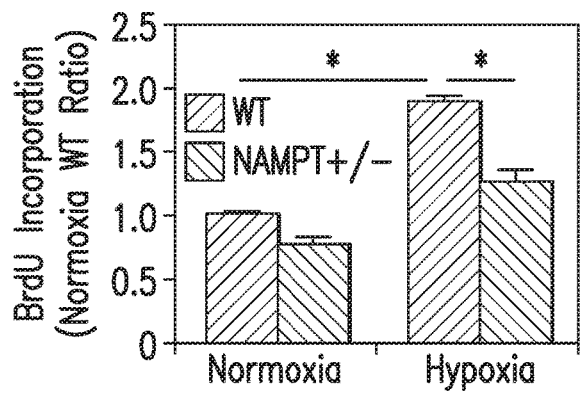
FIGS. 2A and 2B are bar graphs showing protective effect of reduced NAMPT expression on cell proliferation exhibited by heterozygous NAMPT+/− mice compared to WT controls (WT), with exposure to hypoxia. BrdU incorporation (FIG. 2A) and total cell numbers (FIG. 2B) of lung smooth muscle cells (SMC) were reduced NAMPT+/− mice exposed to hypoxia compared to WT controls. Results are expressed as mean SEM; n=10 per group. *p<0.05.
Figure 2B:
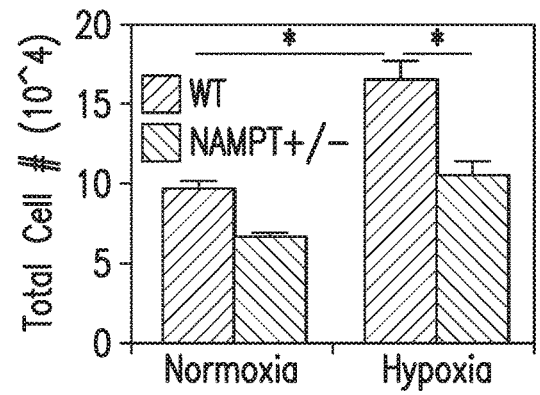

Results eNAMPT drives NAMPT-mediated EC and SMC proliferation in PH. NAMPT+/− mice exposed to chronic hypoxia exhibited reduced PH severity (FIGS. 1A-1D), with isolated lung SMCs exhibiting reduced proliferation (FIGS. 2A-2B). FIGS. 3A-3D depict that NAMPT secretion is increased in humans with PAH and in lung ECs collected from PAH patients and that culture medium from human PAH-derived lung ECs stimulate SMC proliferation.

Figure 3A:
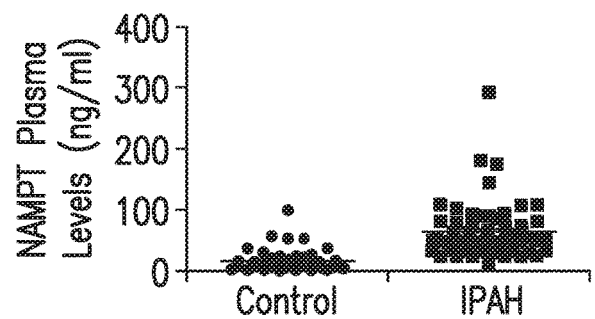
FIG. 3A is a scatterplot of plasma NAMPT values in patients with PAH and controls.
Figure 3B:
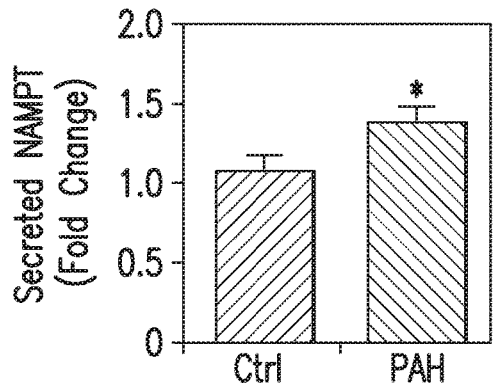
FIG. 3B-D are bar graphs showing increased secreted levels of NAMPT from human lung ECs from PAH patients compared to non-PAH controls (FIG. 3B); increased fold changes in BrdU incorporation in human SMCs and ECs with NAMPT overexpression with or without addition of FK866 (FIG. 3C); and increased fold changes in BrdU incorporation in human lung SMCs exposure to 1, 5, 20 µg/ml recombinant rNAMPT as well as 20 µg/ml rNAMPT and FK866 (FIG. 3D); fold changes in BrdU incorporation in cells treated with platelet-derived growth factor (PDGF) was used as a positive control. Mean±SEM. *p<0.05;  p<0.01; *P<0.001 vs controls.
Figure 3C:
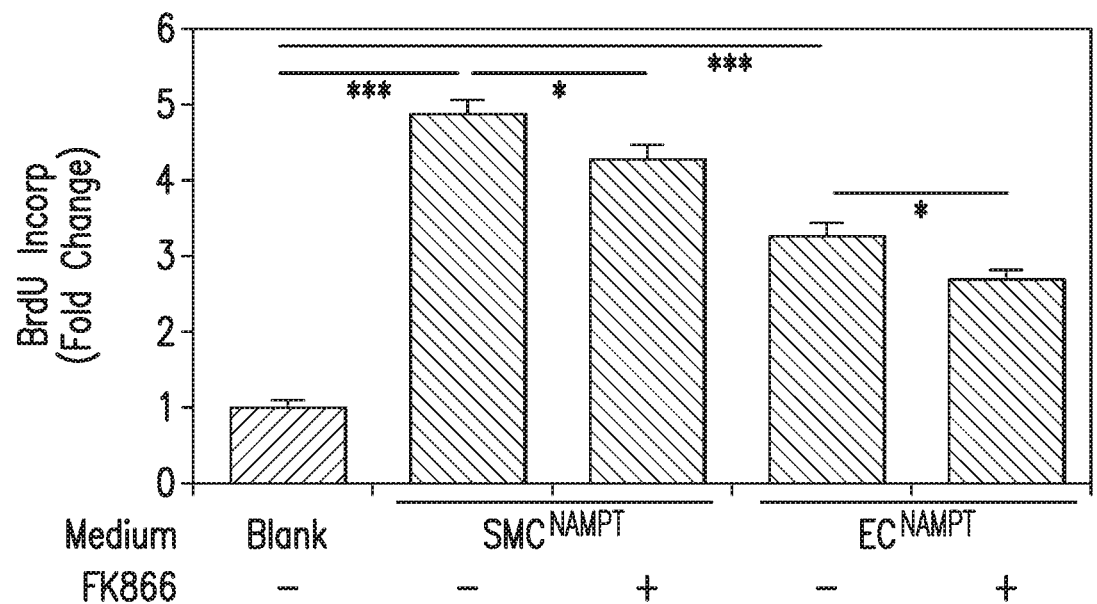
Figure 3D:
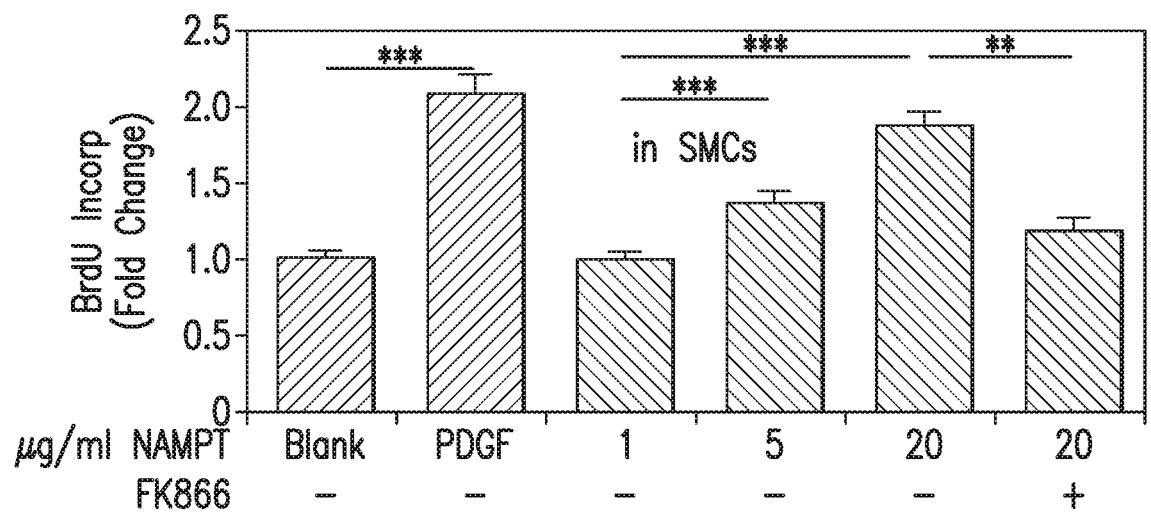

NAMPT overexpression in human lung EC or SMCs promoted cell proliferation (FIG. 3C). Cell culture media from EC overexpressing NAMPT (data not shown) or recombinant NAMPT protein (FIG. 3D) confirmed eNAMPT-mediated increased SMC proliferation with both sources of eNAMPT dose-dependently stimulating human lung SMC proliferation, confirming eNAMPT as the driver for PAH-associated cell proliferation.

The data demonstrate that NAMPT and NAMPT receptor TLR4, are targets for the prevention and attenuation of established PAH. Reduced NAMPT expression (NAMPT+/− mice) reduces hypoxia-mediated PH. NAMPT expression in lung tissues from three rodent PH models (HPH, MCT, HSU) was determined. FIGS. 1A-1D demonstrate that NAMPT+/− mice exposed to the HPH PAH model display significantly lower RVP and RVSP, and less severe vascular remodeling compared with WT siblings (C57BL6).

Example 2: eNAMPT Enhances Human Lung SMC Ca2+ Transients

Materials and Methods
Reagents.

Recombinant NAMPT protein (CY-E1251) was obtained from MBL Lifescience. Solubilized protein lysates isolated from lung tissues and cells were used to detect NAMPT, STIM2, ORAI2 and actin as previously described. Cells were lysed in a modified radioimmunoprecipitation assay (mRIPA) lysis buffer with a protease and phosphatase inhibitor cocktail (Sigma Aldrich, St. Louis, Mo.), and protein quantification and Western blot analysis were performed according to standard procedures.

Human Primary Pulmonary Artery Smooth Muscle Cells (hPASMCs) from control and PAH patients were obtained and isolated as previously described from Lonza (CC-2581 and CC-2530) were used for cell transfection and proliferation assays.

[Ca2+]Cyt Measurement.

[Ca2+]cyt was measured in PASMC loaded with fura-2 (4 mM) in a Nikon digital fluorescent imaging system. Cells were loaded with 4 µM fura-2 acetoxymethyl ester (fura-2/AM) for 60 min at 25° C. and [Ca2+]cyt was measured using a ratiometric method at 32° C. Cyclepiazonic acid (CPA, a specific Ca2+-ATPase inhibitor) was used to induce store-operated calcium entry (SOCE).

Results

Figure 4A:
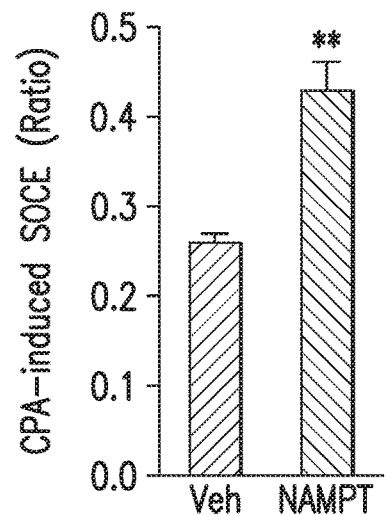
FIGS. 4A-4C are bar graphs showing effect of NAMPT on CPA (a calcium mobilizing agent)-mediated store-operated Ca2+ entry (SOCE) in human lung SMCs incubated with vehicle or rNAMPT protein at 20 µg/ml for 48 hr (FIG. 4A); and on protein levels of STIM2 (FIG. 4B) and ORAI2 (FIG. 4C) after rNAMPT exposure for 48 hr. n>3-5; * p<0.05; **p<0.01. CPA, STIM2, and ORAI2 are a calcium-mobilizing proteins.
Figure 4B:
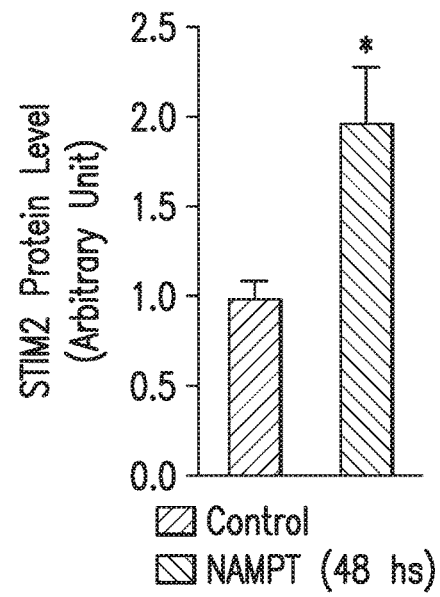
Figure 4C:
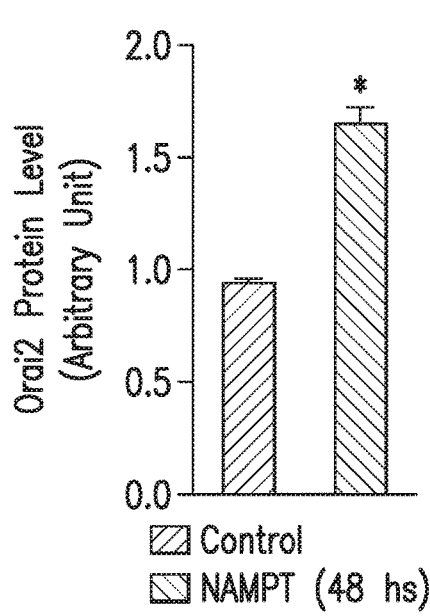
Figure 5A:
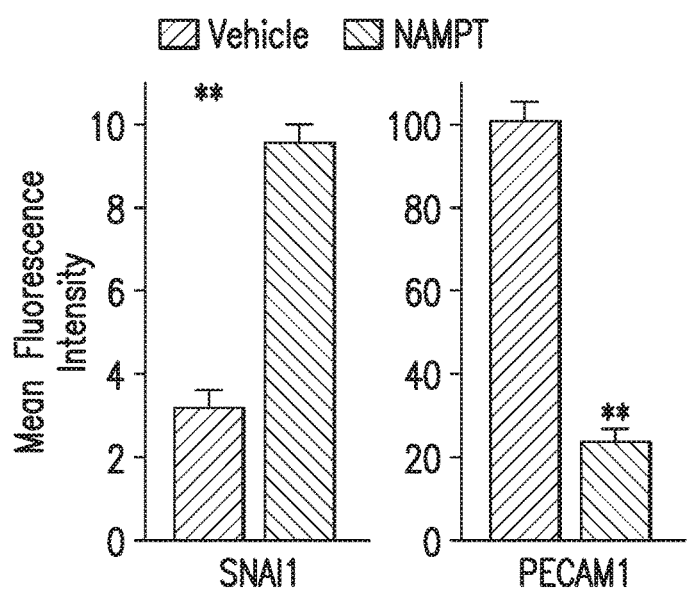
FIGS. 5A-5D are bar graphs showing effect of NAMPT on mean fluorescence intensity of SNAI1, a protein implicated in vascular remodeling, and PECAM1 (FIG. 5A), and % discontinuous adherens junctions (FIG. 5B) in lung EC after incubation with vehicle or rNAMPT; SNAI1 mRNA levels in lung ECs determined by RT-PCR with or without rNAMPT exposure in the presence or absence of addition of TGFβ (FIG. 5C)
Figure 5B:
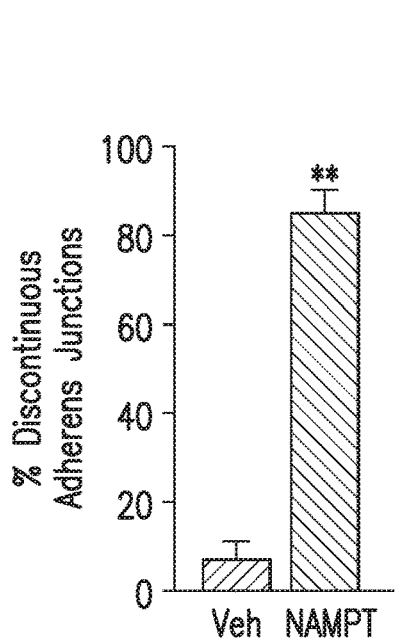
Figure 5C:
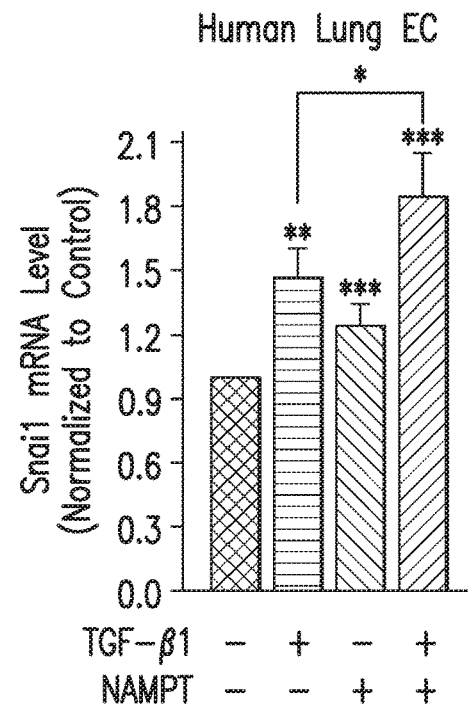
Figure 5D:
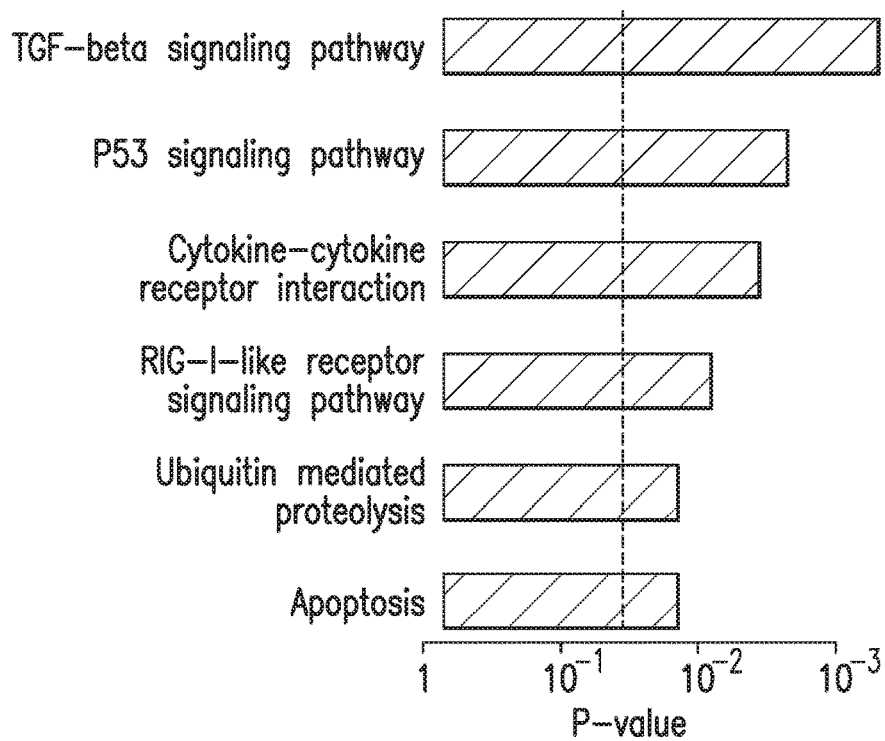

SMC activation is important in vascular remodeling. This can be reflected by increased Ca2+ signaling. Chronic exposure (48 hr, FIGS. 4A-4C) of eNAMPT (20 µg/ml) to human lung SMCs augments cyclopiazonic acid (CPA)-mediated store-operated Ca2+ entry or SOCE, suggesting that eNAMPT triggers EC remodeling of more sensitive Ca2+ signaling, leading to SMC proliferation and contraction, key PAH features. eNAMPT increases expression of stromal interaction molecule 2 (STIM2) and the Ca2+ release-activated Ca2+ modulator 2 (Orai2). These are key SOCE components whose expression is upregulated in SMCs from PAH patients, thus detailing NAMPT mechanisms that influence SMC Ca2+ transients.

Example 3: rNAMPT Stimulates Human Lung Endothelial-Mesenchymal Transition (EndMT)

Materials and Methods
Reagents.

Recombinant NAMPT protein (CY-E1251) and TGFβ1 was obtained from MBL Lifescience. Solubilized protein lysates isolated from lung tissues and cells were used to detect NAMPT, SNAIL PECAM and actin as previously described. Cells were lysed in a modified radioimmunoprecipitation assay (mRIPA) lysis buffer with a protease and phosphatase inhibitor cocktail (Sigma Aldrich, St. Louis, Mo.), and protein quantification and Western blot analysis were performed according to standard procedures.
Cell Culture, siRNA Transfection.

Human pulmonary artery endothelial cells (EC) were obtained from Lonza (Walkersville Md.) and were cultured in the manufacturer's recommended endothelial growth medium-2 (EGM-2). Cells were grown at 37° C. in a 5% $CO_2$ incubator, and passages 6 to 9 were used for experiments. Media was changed one day before experimentation. For RNA interference, On-Target Plus siRNAs against SNAI1 were obtained from Dharmacon (Lafayette Colo.) and transfected into EC at a final concentration of 100 nM.
Murine NAMPT-Induced Lung Gene Expression.

The transcriptomic analysis for NAMPT-exposed mice were based on the data generated by Affymetrix Mouse Genome 430 2.0 Array (NCBI GEO dataset ID: GSE9368 and GSE9314). The GeneChip Robust Multiarray Averaging (GCRMA) method was used to summarize the genome-wide gene expression levels. Only the probe sets present (determined by function "mas5calls" in the Bioconductor "affy" package) in all the samples of at least one group were retained. The robust multi-array average (RMA) function in the "affy" package of Bioconductor was used to summarize the expression level of each probe set. The significance analysis of microarrays (SAM) algorithm was used to identify the genes deregulated by NAMPT based on log 2-transformed gene expression levels. FDR was controlled using the q-value method.
Results EndMT is a key feature of vascular remodeling in PAH. FIGS. 5A-5D depict decreased expression of EC marker (PECAM1) (36) and increased expression of mesenchymal cell markers (Snai1, Snai2) (37) in human lung ECs isolated from PAH patients, reflecting the loss of cell-cell adhesion and conversion of ECs to a fibroblast phenotype. The PAH-inducing agonist, TGFβ1, upregulates Snai1 (and Snai2 and reduces PECAM1) ex-pression (FIG. 5D), that is augmented by NAMPT. These results, suggesting eNAMPT is a novel modulator of EndMT involved in PAH vascular remodeling, are supported by microarray analyses of NAMPT-silenced lung ECs demonstrating TGFβ signaling pathway as the most heavily dysregulated gene ontology pathway.

Example 4: NAMPT-Mediated EC Resistance to Apoptosis Reflects eNAMPT Ligation of TLR4 and NFkB Activation Materials and Methods
Reagents.

Recombinant human TNF-α (R&D Systems, Minneapolis, Minn.); FasL, z-DEVD-fmk (Millipore, Burlington, Mass.); tBHP and immunoblotting antibodies (Sigma, St. Louis, Mo.); siRNAs against NAMPT were obtained from Invitrogen (Carlsbad, Calif.).
Cell Culture, siRNA Transfection.

Human pulmonary artery endothelial cells (EC) were obtained from Lonza (Walkersville Md.) and were cultured in the manufacturer's recommended endothelial growth medium-2 (EGM-2). Cells were grown at 37° C. in a 5% CO2 incubator, and passages 6 to 9 were used for experiments. Media was changed one day before experimentation. For RNA interference, siRNAs were transfected into EC at a final concentration of 100 nM for 72 hrs. Protein quantification and Western blot analysis were performed according to standard procedures.
NAMPT Expression Modulates EC Susceptibility to TNF-α-Induced Apoptosis.

(A) EC transfection with NAMPT gene siRNA (72 hrs) reduced NAMPT expression and resulted in marked increases in full length PARP-1 expression (compared to transfection with control siRNAs) in both vehicle- and TNF-α-challenged ECs (30 ng/ml, 5 hrs). TNF-α challenge of NAMPT-silenced ECs markedly increased PARP-1 cleavage proteolysis, whereas scrambled siRNA-treated EC exhibited minimal increases in PARP-1 cleavage. *, p<0.05. (B) ECs were pre-treated (6 hrs) with either vehicle (DMSO) or with a caspase-3 inhibitor (z-DEVD-fmk, 20 μM) prior to 24 hr challenge with TNF-α (30 ng/ml), FasL (100 ng/ml) or tBHP (5 mM). Inhibition of caspase-3 activity significantly reduced subsequent PARP-1 cleavage induced by TNF-α. (C) ECs were transfected with myc-tagged NAMPT plasmid resulting in marked NAMPT overexpression. Compared with EC transfected with myc-tag only, EC overexpressing NAMPT exhibited virtual abolishment of PARP cleavage after TNF-α challenge (30 ng/ml or 100 ng/ml, 24 hrs). Error bars indicate SEM of three independent experiments.
In Silico Computational Modeling.

Figure 6:
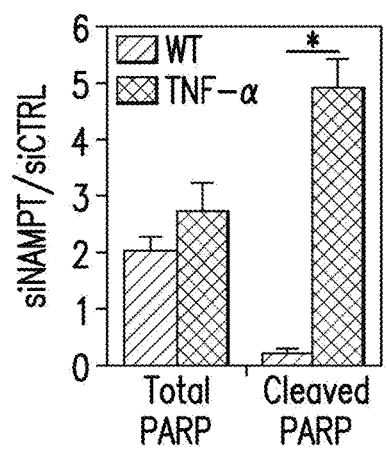
FIG. 6 is a bar graph of siNAMPT/isCYTL for total PARP and cleaved PARP.
Figure 7A:
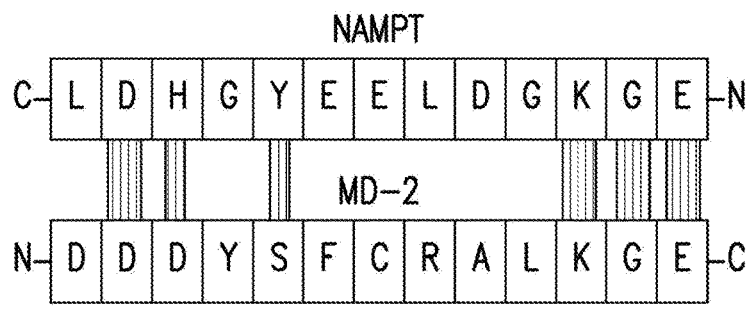
FIGS. 7A-7E are diagrams showing In silico modeling of eNAMPT and MD-2 interactions with the NAMPT receptor, TLR4, including sequence of the N-to-C order of the TLR4-binding loop of MD-2 is aligned with NAMPT loop in the reverse C-to-N order with residues involved in MD-2-TLR4 binding indicated (FIG. 7A). Wider bands indicate aligned identical residues, narrower bands indicate aligned residues with similar physicochemical properties.
Figure 7B:
Figure 7C:
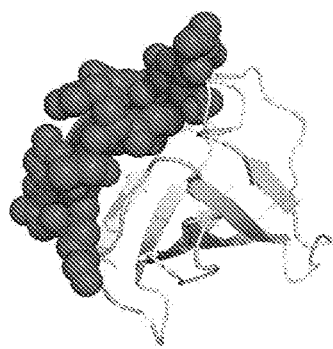
Figure 7D:
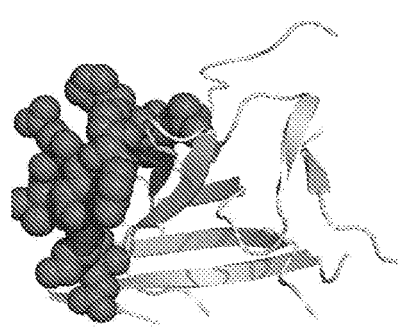
Figure 7E:

In silico analysis are as previously described. The structures of LPS binding pockets analyzed include: 1N12 (*E. coli*), 4GGM (*Caulobacter*), 3MU3 (jungle fowl), 3RGY (cattle), 3VQ1 (mouse), 4G8A and 2E59 (human).
Results Altered NAMPT expression significantly influences TNFα-mediated human lung endothelial cell (EC) apoptosis. To explore precise mechanisms by which NAMPT modulates cell survival and apoptosis, human lung ECs were transfected with a NAMPT-specific siRNA resulting in reduced NAMPT expression after 72 hrs (FIG. 6A). Poly (ADP-ribose) polymerase-1 or PARP-1 is a multifunctional regulator of transcription, chromatin structure and genomic integrity activated by DNA breaks using NAD as a substrate. During apoptosis, PARP-1 is cleaved by caspase-3 in two distinct fragments of 24 kDa and 89 kDa. NAMPT gene silencing in ECs for 72 hrs resulted in significant increases in PARP-1 expression reflecting increased EC apoptosis (compared to control-silenced/scrambled siRNA group). Identical increases in EC apoptosis were observed in NAMPT-silenced EC that were subsequently treated for 5 hrs with 30 ng/ml TNF-α with increased PARP-1 cleavage compared to control-silenced ECs. To confirm that PARP-1 cleavage was indeed dependent on caspase-3 activation, unsilenced ECs were pre-incubated (6 hrs) with the known caspase-3 inhibitor, z-DEVD-fmk, prior to exposure to TNF-α, FasL or tBPH (24 hrs), inducers of apoptosis. EC pretreated with z-DEVD-fmk and challenged with TNF-α demonstrated significantly reduced PARP-1 cleavage compared to EC pre-treated with vehicle alone (DMSO) (FIG. 6). In contrast to results obtained by NAMPT silencing in ECs that resulted in increased EC apoptosis, the transient plasmid-based overexpression of human NAMPT served to decrease levels of cleaved PARP-1 induced by TNF-α, indicating that increases in NAMPT expression and protein levels reduces EC apoptosis.

eNAMPT ligation of TLR4 and induced NFκB activation in mice and humans is primarily involved in NAMPT-mediated human lung EC resistance to apoptosis. Gel electrophoresis was used to demonstrate that reduced NAMPT expression (siRNA) increases susceptibility to TNFα-induced EC apoptosis, reflected by PARP-1 cleavage consistent with caspase-3 activation and enhanced apoptosis. In contrast, NAMPT overexpression reduced TNFα-induced EC apoptosis. Inhibition of NAMPT enzymatic activity by the NAMPT inhibitor, FK866, failed to alter TNFα-induced EC apoptosis, whereas NAMPT neutralizing Ab did attenuate EC apoptosis suggesting secreted NAMPT and subsequent eNAMPT regulates lung EC apoptosis and lung remodeling (reported in Novel Mechanism for Nicotinamide Phosphoribosyltransferase Inhibition of TNF-α-Mediated Apoptosis in Human Lung Endothelial Cells. Oita R C, Camp S M, Ma W, Ceco E, Harbeck M, Singleton P, Messana J, Sun X, Wang T, Garcia J G N. Am J Respir Cell Mol Biol. 2018 Jan. 16. doi: 10.1165/rcmb.2017-0155OC. PMID: 29337590).

MD-2 is a critical LPS- and TLR4-binding protein necessary for TLR4 activation. Whereas only~30% sequence identity exists between NAMPT and MD-2, FIGS. 7A-7E depict striking structural similarity and N-to-C order alignment between loop regions in NAMPT and MD-2 involved in MD-2LPS-TLR4 binding and TLR4 activation. This NAMPT loop region contains six of the seven MD-2 residues important for TLR4 binding and a prominent MD-2 motif consisting of a consecutive triplet of fully conserved residues (Lys109, Gly110, Glu111). A computational model (Camp, et al., *Scientific Report,* 5,13135(2015)) characterizes LPS-binding regions and identified Phe119, Leu74, Leu94, and Ile52 as the most important MD-2 signature residues for LPS binding. Direct LPS binding by NAMPT via this signature is unlikely as the distance between LPS-binding MD-2 residues Phe119 and Ile52 for Phe399 is 3.8 Å whereas corresponding NAMPT residue distance and Ile114 is 9.3 Å. NAMPT dimerization is required for enzymatic activity.

Example 5: TLR4 Inhibition Reduces eNAMPT-Induced PAH In Vivo

Materials and Methods
Animal Work.

A rodent (Sprague-Dawley male rats, 150-200 grams) monocrotaline (MCT) model was utilized to mimic PAH and test the effect of blocking NAMPT receptor, TLR4, with the TLR4 agonist, RS-LPS (Invivogen, San Diego, Calif.). Daily IP injections of RS-LPS (4 weeks) were administered (250 ug/kg). Four groups were compared for treatment efficacy: Control, RS-LPS alone, MCT with vehicle control, MCT with RS-LPS. At the end of the 4 week protocol, assessment of right ventricular systolic pressures (RVSP) were achieved in anesthetized animals (125 mg/kg ketamine and 1.25 mg/kg acepromazine mixture) injected intraperitoneally. RVSP was measured by a catheter (Millar Instruments) positioned in the RV via the external jugular vein and a 1.4-French pressure transducer (Millar Instruments, SPF 1030). RVSP was recorded and analyzed using the Acg-Knowledge software (Biopac Systems). RVSP was used as a surrogate for pulmonary arterial systolic pressure. After pressures were recorded, animals were euthanized by exsanguination, and the heart and lungs were removed en bloc. RV hypertrophy (RVH) was determined by the ratio of the weight of the RV wall divided by the sum of the weights of the left ventricle and the septum as previously reported (Moreno-Vinasco et al., 2008; Tang et al., 2016). Lungs were perfused with PBS, removed, and frozen in liquid nitrogen for Western blotting analysis and real-time RT-PCR analysis, as well as fixed in a 10% normalized formalin solution overnight for morphometric analysis.

Results.

Figure 8A:
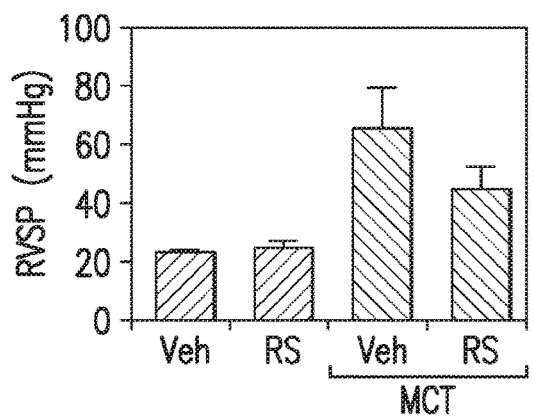
FIGS. 8A-8B are bar graphs showing RVSP (FIG. 8A) and in Fulton's Index, RV/(LV+S) (FIG. 8B) in vehicle-treated and RS-LPS (an inhibitor of TLR4)-treated with or without monocrotaline (MCT) to induce PAH in rats. RS-LPS (20 µg/kg/day, IP) was administered beginning on the second day after MCT injection, and analysis was carried out at 28 days post MCT injection. p<0.001 compared to controls; ***p<0.001 compared to MCT group.
Figure 8B:
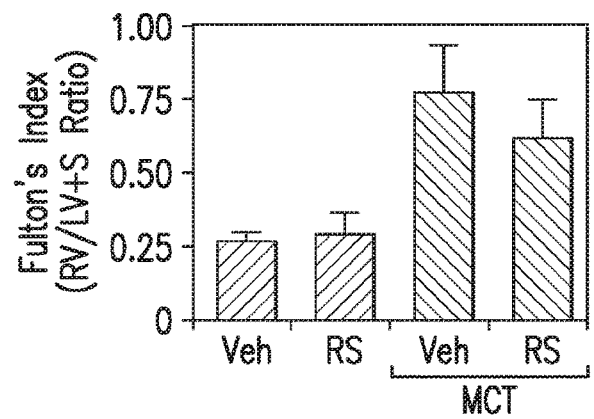

The TLR4 antagonist, RS-LPS, attenuated eNAMPT-induced NFkB phosphorylation and acute lung injury. FIGS. 8A-8B reflect partial attenuation of MCT-induced PAH (RVSP and RV remodeling), suggesting that TLR4 activation by eNAMPT is key in PAH development in this model.

Example 6: NAMPT Enzymatic Inhibition Reduces PAH In Vivo

Materials and Methods
Inhibition of NAMPT Enzymatic Activities with Novel FK-866 Analogs.

CycLex NAMPT Colorimetric Assay Kit was purchased from MBL International (Woburn, Mass.) and utilized to screen the effect of putative NAMPT inhibitors on NAMPT enzymatic activity. Three doses (0.1, 1, 10 uM) of each NAMPT inhibitors was used following the manufacturer's instruction.

Figure 9A:
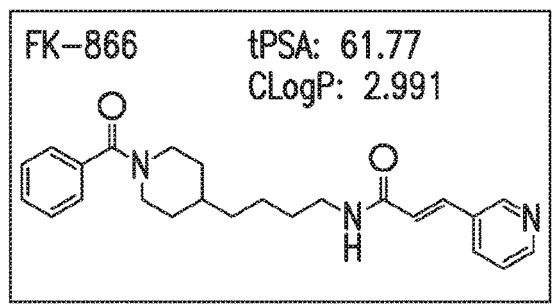
FIGS. 9A-9E are chemical drawings showing NAMPT inhibitor, FK-866 (FIG. 9A), structure is divided into three regions (FIG. 9B) and varied by replacing with N-heterocycles to generate novel FK866 analogs: MS-1-82 (FIG. 9C), Rari049 (FIG. 9D), Alpii135 (FIG. 9E).
Figure 9B:
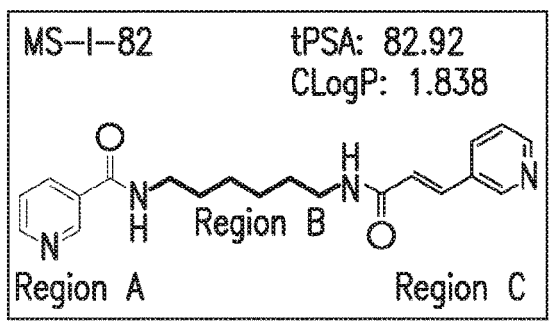
Figure 9C:
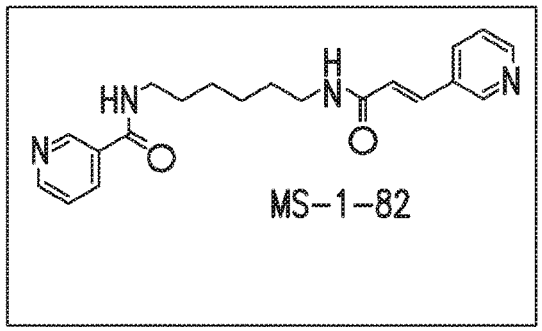
Figure 9D:
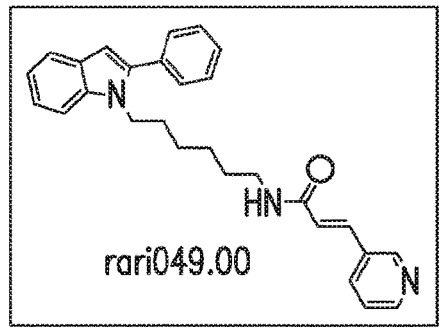
Figure 9E:
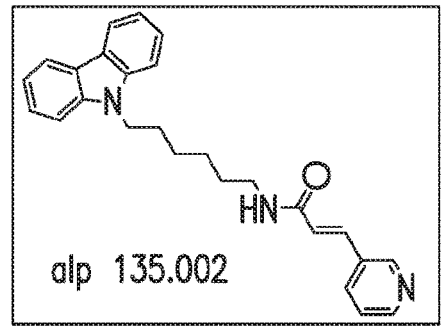
Figure 10A:
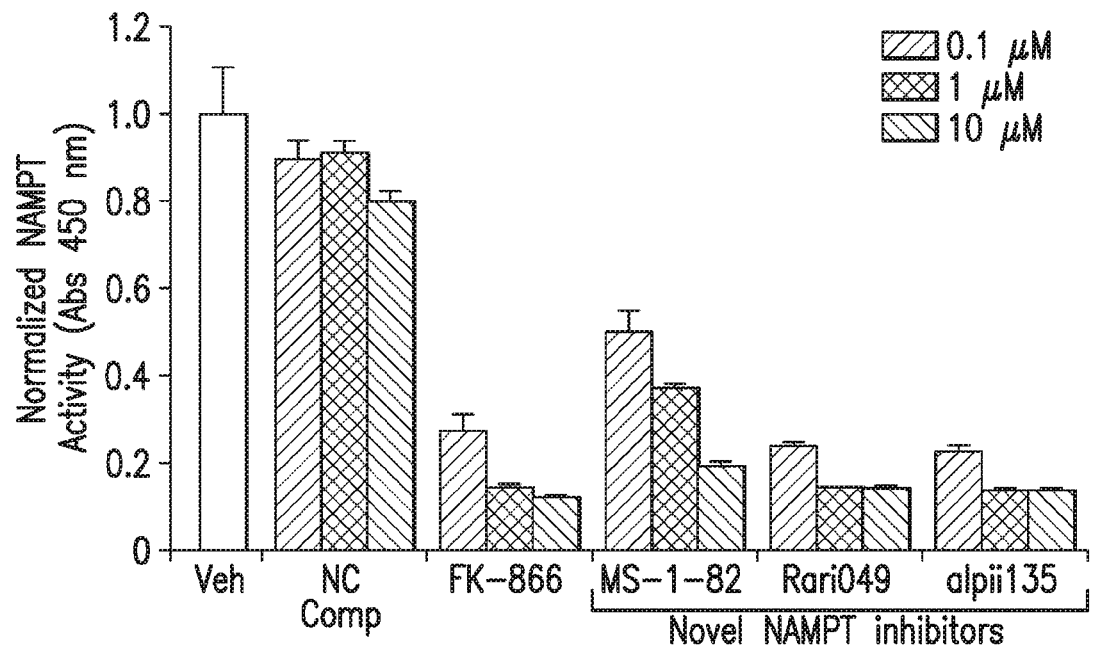
FIG. 10A is a bar graph showing normalized NAMPT activity in the present of FK866 and FK analogues MS-1-82, Rari049, Alp-135 at 0.1, 1, and 10 µM concentrations.
Figure 10B:
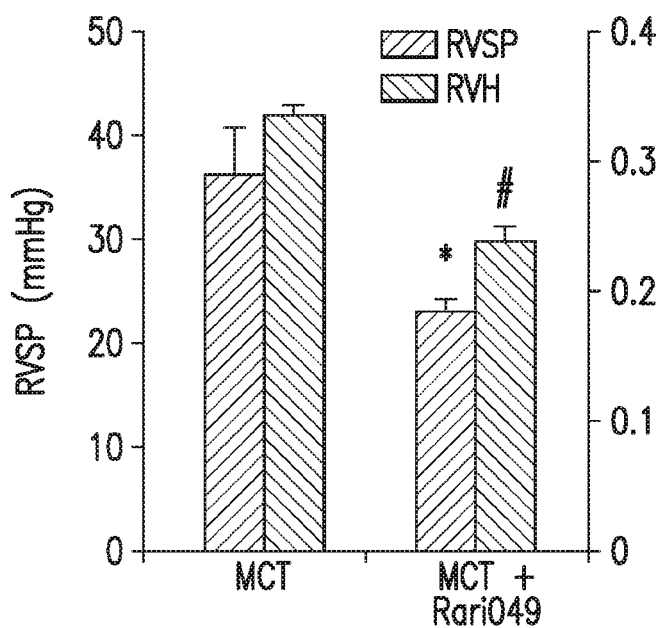
FIG. 10B is a bar graph showing RVSP in MCT-induced PH in rats and in MCT-induced PH in rats with Rari049 (2.5 mg/kg, i.p. BID, ×2 wks) (RVSP-right ventricular systolic pressure, RVH-RV hypertrophy-ratio of RV and LV plus septal-S weight).
Figure 11A:
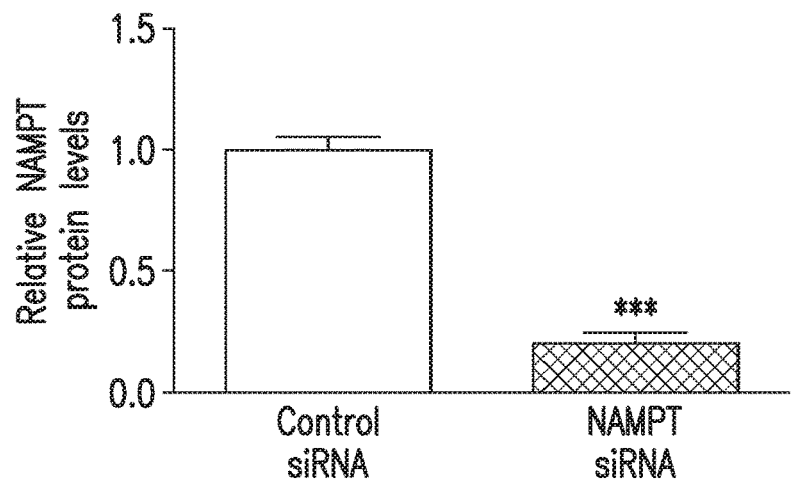
FIGS. 11A-11C are bar graphs showing the effect of NAMPT silencing on cell proliferation.
Figure 11B:
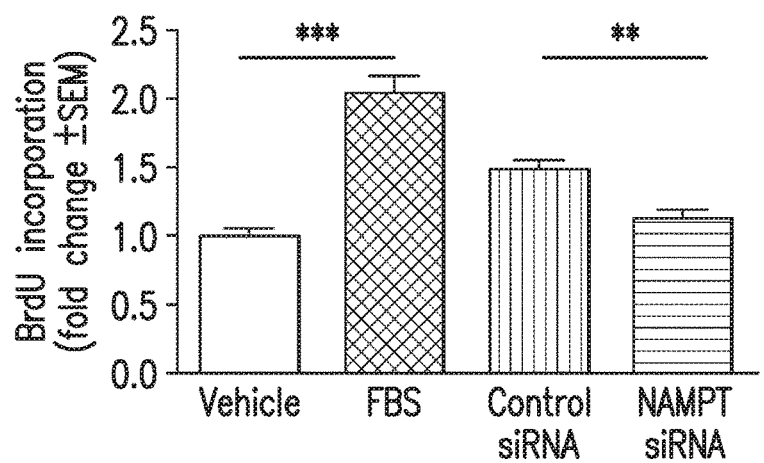
Figure 11C:
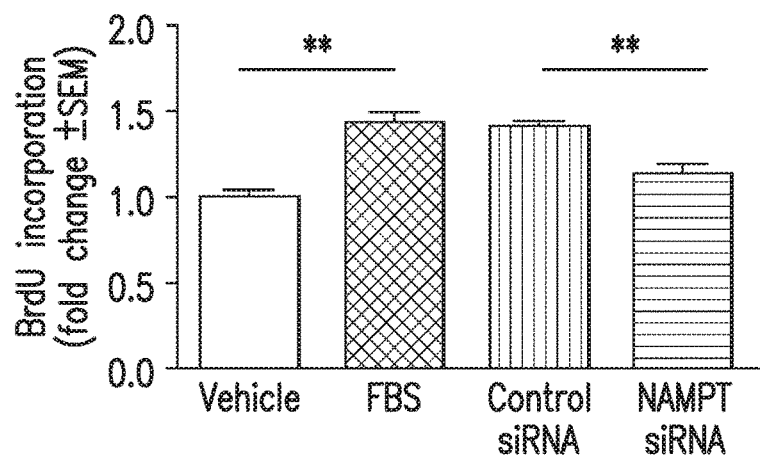
Figure 11D:
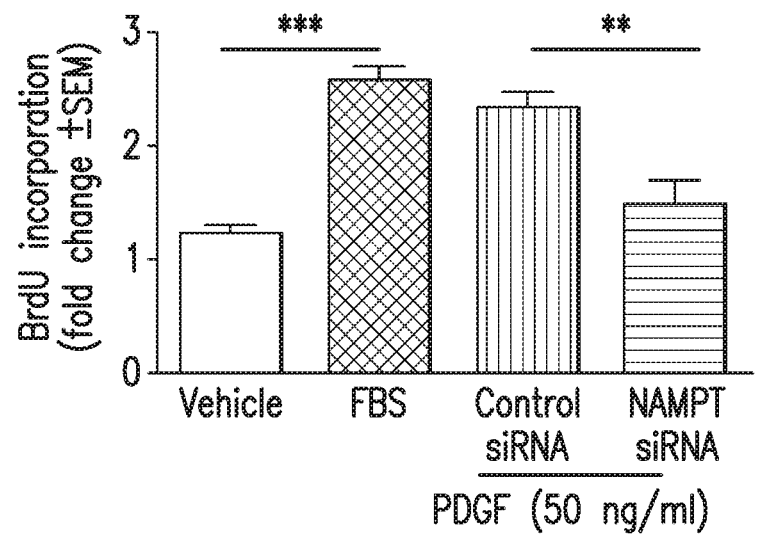
FIG. 11D is a bar graph showing BrdU incorporation for each of vehicle, FBS, and Control groups, as well as siRNA, and NAMPT iRNA groups in presence of PDGF (50 ng/ml).

FIG. 9A depicts the structure of the NAMPT inhibitor, FK-866, the three FK domains (FIG. 9B), and three novel FK-866 analogues: MS-1-82 (FIG. 9B), Rari049 (FIG. 9C), and Alp135 (FIG. 9D), with excellent dose-dependent enzyme inhibitory properties (FIG. 9E). Studies in MCT-PH show that Rari049 (2.5 mg/kg, i.p. BID, ×2 wks) show it should be useful in preventive therapy reducing both RVSP and RVH (FIG. 10A, 10B).

Example 7: NAMPT Downregulation Via siRNA Attenuates Human Muscle Cell (PASMC) Proliferation Materials and Methods
Reagents, Pharmacologic Inhibitors and Antibodies.

Recombinant NAMPT protein (CY-E1251) was obtained from MBL International (Woburn, Mass.). The NAMPT specific inhibitor (FK866, Cat. #F8557) and monoclonal anti-J3-actin-peroxidase antibody (cat. #A3854) were from Sigma. Rabbit anti-NAMPT (cat. #A300-372A), STIM2 (cat. #4917S), anti-ORA12 (cat. #ab180146) and PCNA (cat. #SC-7907) antibodies were purchased from Bethyl Laboratories, Inc, Cell Signaling, ABCAM, Santa Cruz, respectively. NAD/NADH Quantitation Colorimetric Kit (cat. #K337 100) was from BioVision, Inc. Cell death assays were performed using a cytotoxicity detection Kit (LDH, cat. #11644793001, Sigma) and cell viability was examined using CeliTiter 96 Aqueous One Solution Cell Proliferation Assay kit (Cat. #G3580, Promega). Cell migration was conducted using Falcon™ Cell Culture Inserts (Fisher, Cat.

08-771-12) and migrated cells were stained by 1% aqueous Crystal Violet solution (Electron Microscopy Sciences, Cat. #RT 26088-10). H2O2 (100~M, Sigma, Cat. #ab66110) was used as an apoptosis stimulus for hPASMCs. Cell apoptosis was examined using an in situ BrdU-Red DNA fragmentation (TUNEL) kit. Verapamil hydrochloride (Sigma, Cat #V4629-1 G), a phenylalkylamine Ca2+channel blocker, was used to study the effect of Ltype Calcium channel on the SOCE in hPASMCs.

Human Primary Pulmonary Artery Smooth Muscle Cells (hPASMCs) from control and PAH patients were obtained and isolated as previously described from Lonza (CC-2581 and CC-2530) were used for cell transfection and proliferation assays.

Using Lipofectamine™ RNAiMAX Reagent (Invitrogen, cat. #13778-150), hPASMCs were transfected with NAMPT siRNA (L-000458-00) or scrambled siRNA (0-001810-02), which were purchased from Oharmacon (Thermo Fisher Scientific, Lafayette, Colo., USA) according to the manufacturer's protocol. (3-actin was used for normalization. Experiments were repeated more than three times.

Results

BrdU incorporation assays demonstrated that silencing NAMPT via its specific siRNA attenuated hPAMSC proliferation under normoxia, hypoxia or POGF stimulation. (see FIGS. 11A-11D). Results are expressed as mean±SEM; n=6 per group. P<0.01; *P<0.001. FBS was used as a positive control for BrdU proliferation assays.

Example 8: Transwell Migration and Wound Healing Assays Demonstrate that Recombinant NAMPT Protein (rNAMPT) Promotes Human PASMC Migration Materials and Methods For quantitative data from transwell migration assays (ANOVA P<0.05). 50,000 cells were added into Falcon™ Cell Culture Inserts (Fisher, Cat. #08-771-12) with 8-μm pores in 1 ml of basal medium and 250 μl on the top of the transwell. Cells were then stimulated by vehicle, rhNAMPT (20 μg/ml) with or without FK866 (10 μM) for 48 hrs. Unmigrated cells were then scraped from the top of the filter and the migrated bottom layer of cells were stained by 1% aqueous Crystal Violet solution (Electron Microscopy Sciences, Cat. #RT 26088-10). The transwell bottom was gently separated by a blade and put on a glass slide for imaging.

The migrated cells were counted and quantified. Images were taken by an Olympus BX51Fluorescence Microscope and processed by DPController Software (Oylmpus IMS).

In wound healing assays, approximately 0.5 million human Primary Pulmonary Artery Smooth Muscle Cells (hPASMCs) were seeded to 6-well cell culture plates, a straight line was scratched using a 200-μl pipette tip after cells reached 100% confluence. Three dots were labelled beside each line. The cells were immediately washed by culture medium and then starved with M199 medium including 0.1% FBS for 3 hours, followed by stimulation with vehicle or rhNAMPT (20 μg/ml) with or without FK866 (10 μM). The cells were imaged at 6 hrs after stimulation.

Image J software was used to measure the wound line width for all the three spots labeled in each line. Wound closure %={[width (start point)-width (end point)]/width (start point)}×100% was calculated (ANOVA P<0.05).

Results

Figure 12A:
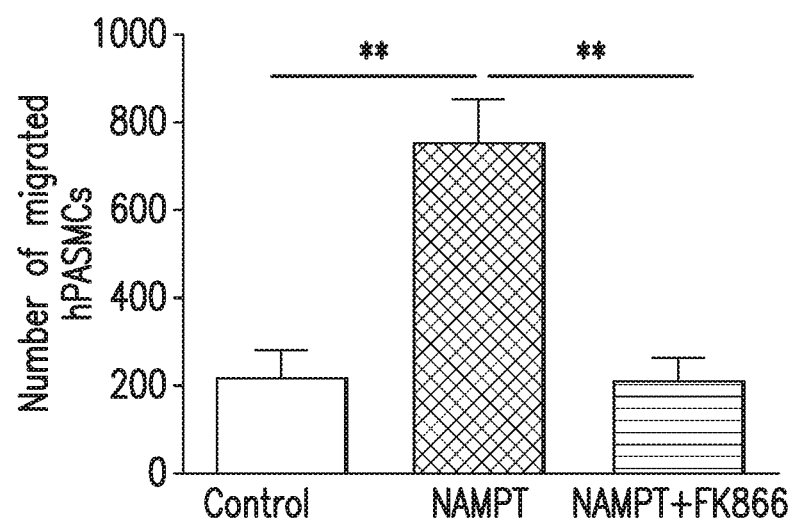
FIGS. 12A-12B are bar graphs depicting the effect of the NAMPT enzymatic inhibitor, FK-866.
Figure 12B:
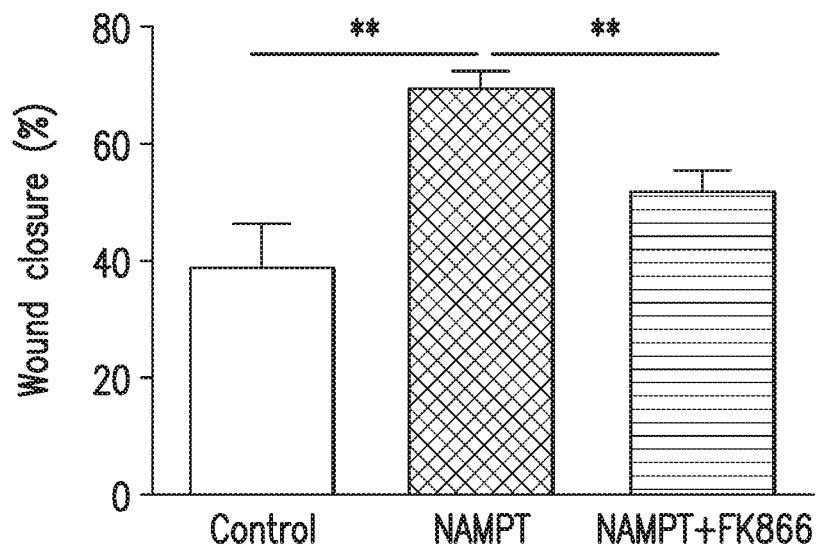

The data indicated that recombinant NAMPT protein (rNAMPT) promotes human PASMC migration. These data are presented in FIGS. 12A and 12B, showing the numbers of migrated hPASMCs and % wound closure, respectively, in control vs NAMPT, as well as an inhibitor of NAMPT, FK866 (**P<0.01).

Example 9: NAMPT Protein Inhibits hPASMC Apoptosis and FK866 Promotes Cell Apoptosis Materials and Methods hPASMCs were cultured on a coverslip in a 6-well cell culture plate. H2O2 (100 μM, Sigma, Cat. #ab66110) was used as an apoptosis stimulus for hPASMCs.

When cell confluence reached 95%, cells were starved for 3 hrs and stimulated by H2O2, FK866 (10 μM), H2O2+ rhNAMPT (20 μg/ml) or H2O2+rhNAMPT (20 μg/ml) with FK866 (10 μM) for 24 hrs. Cell apoptosis was examined using an in situ BrdU-Red DNA fragmentation (TUNEL) kit. The cells on the coverslips were examined using a Nikon Eclipse E800 fluorescence microscope, and the images were processed by MetaMorph software (Molecular Devices, Inc.). Approximately ten images were taken from each condition, and over 500 cells were counted according to DAPI staining.

Results

Figure 13:
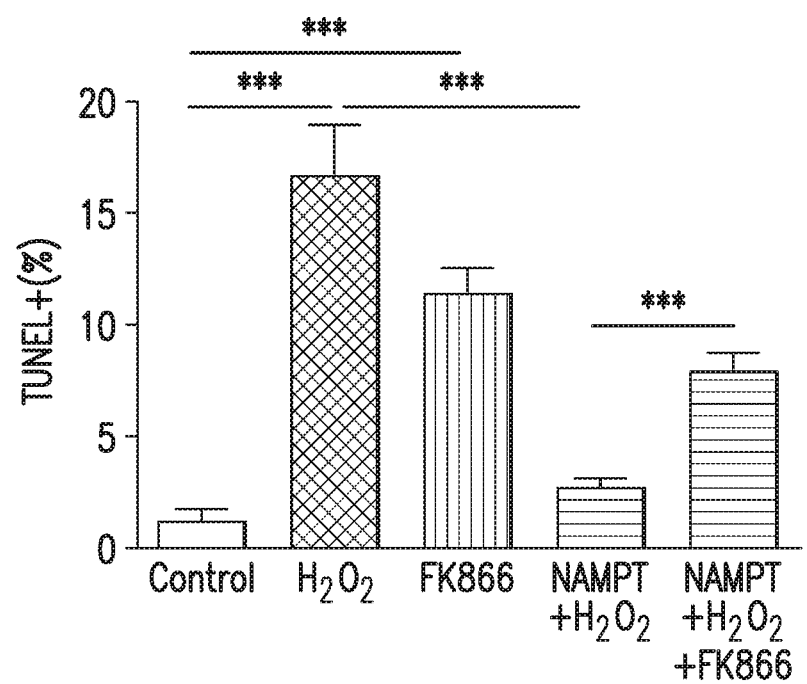
FIG. 13 is a bar graph depicting the effect of the NAMPT enzymatic inhibitor, FK-866, on apoptosis Shown is the % TUNEL for each of Control, H202, FK-866, NAMPT+H202 and NAMPT+FK866+H202 groups, respectively.

The data from the TUNEL assay revealed that the NAMPT protein inhibits hPASMC apoptosis, and FK866 promotes cell apoptosis. The number of TUNEL positive cells was quantified, as shown in FIG. 13. (***P<0.001).

Example 10: Anti-NAMPT Polyclonal Antibodies are Effective in PAH

Materials and Methods
Monocrotaline (MCT) Model of PAH.

Male Sprague-Dawley rats (190-200 g) were used for the MCT and SU5416-hypoxia induced PH studies. In the MCT-induced PH model, MCT was dissolved in 0.5N HCl to 200 mg/ml, neutralized to pH 7.4 with 0.5N NaOH, and then diluted with sterile water to 60 mg/ml. One dose of MCT (60 mg/kg body weight) was subcutaneously injected to rats. Control rats were injected with the equivalent volume of dissolvent solution according to their weights. Food and water were provided ad libitum and the rats are checked once per day. For the prevention experiment, FK866 (2.5 mg/kg) was started in day 2 after the MCT injection and continued for two weeks (Figure S6A); for the reversal experiment, FK866 (2.5 mg/kg every 48 hours) was started day 14 after the MCT injection and continued for two weeks (Figure S6B). Each group included 6 to 8 rats. In the SU5416-hypoxia PH model, one dose of SU5416 (20 mg/kg) was given subcutaneously at the first day of hypoxia exposure (10% $O_2$). After three-week chronic hypoxia exposure, the rats were placed back to room air. FK866 (2.5 mg/kg every 48 hours) was then started two weeks after reoxygenation and continued for three weeks (Figure S6C). Each group included 10 to 12 rats.

Right ventricular systolic pressure (RVSP) was determined by right heart catheterization using a Millar pressure transducer catheter. A weight ratio of the right ventricle divided by the sum of left ventricle and septum (RV/(LV+S)) was measured to determine the extent of right ventricular hypertrophy (RVH). Pulmonary artery remodeling was assessed using Aperio ImageScope software (version 11) after lungs were stained with hematoxylin and eosin. A minimum of 10 microscopic fields were examined for each slide. Approximately twenty muscular arteries with diameters (D) 50-100 μm or D<50 μm per lung section were outlined and measured. Vessel remodeling was calculated as (external vessel area−internal vessel area)/external vessel area).

Results

Administration of a polyclonal antibody to NAMPT was effective in treating elevated RVSP, as shown in FIGS. 14A-14D and 15.

Figure 14A:
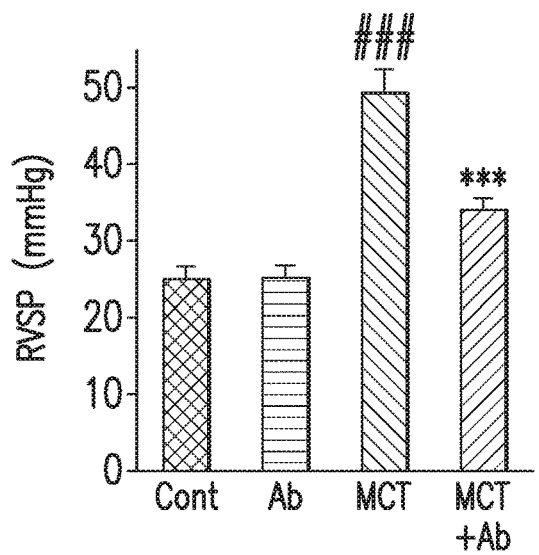
FIGS. 14A-14D are graphs depicting the protective effect of a polyclonal anti-NAMPT neutralizing antibody.
Figure 14B:
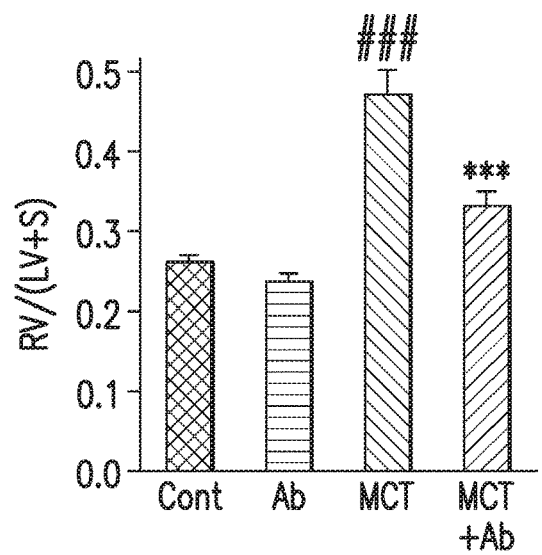
Figure 14C:
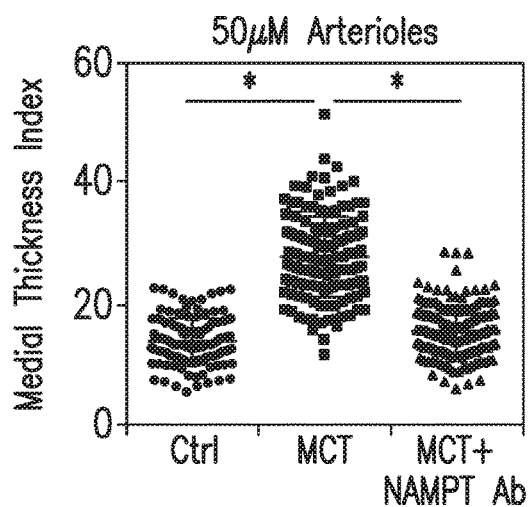
Figure 14D:
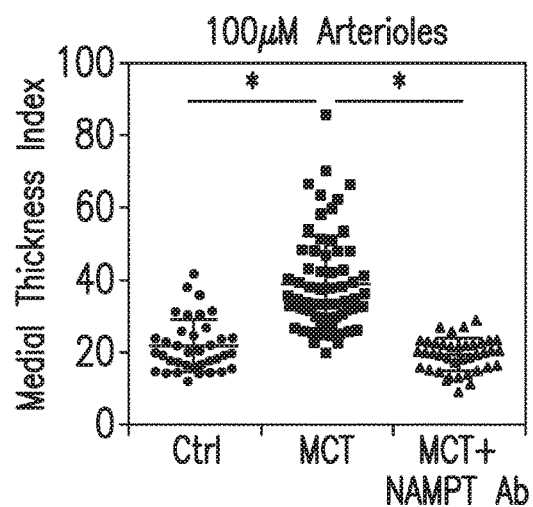

FIG. 14A is a graph of RVSP (mm Hg); FIG. 14B is a graph of RV/(LV+S) (mm Hg); and FIGS. 14C and 14C are graphs of medial thickness index for 50 μM (FIG. 14C) and 100 μM (FIG. 14D) arterioles, for control, anti-NAMPT antibody treated control, MCT and MCT treated with anti-NAMPT antibody.

Figure 15:
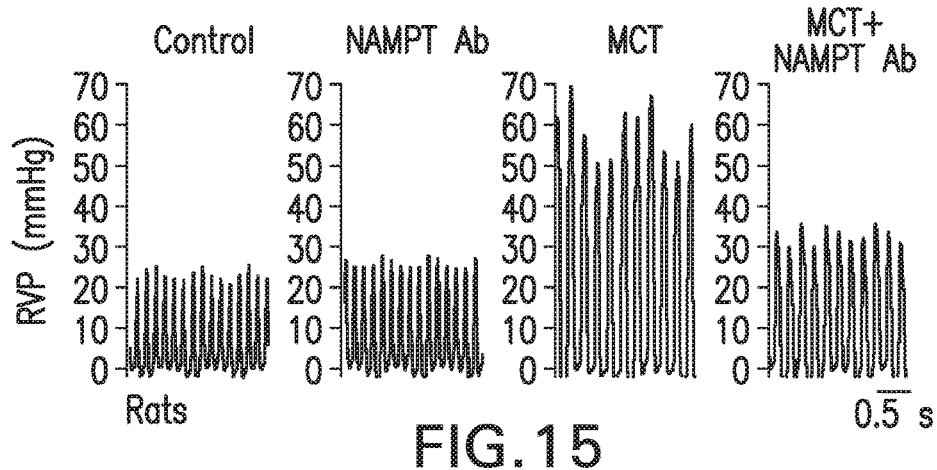
FIG. 15 is a graph of RVP (mm Hg) over time (0.5 seconds) for control rats, NAMPT antibody treated control rats, MCT and MCT rats treated with NAMPT antibodies.

FIG. 15 is a graph of RVP (mm Hg) over time (0.5 seconds) for control rats, NAMPT antibody treated control rats, MCT and MCT rats treated with NAMPT antibodies.

I claim:

1. A method to reduce Pulmonary Arterial Hypertension (PAH) in a human patient in need thereof comprising systemically administering an effective amount of one or more inhibitors of nicotinamide phosphoribosyltransferase (NAMPT), one or more inhibitors of a NAMPT receptor, or combinations thereof.

2. The method of claim 1 wherein an effective amount of one or more inhibitors of NAMPT, one or more inhibitors of the NAMPT receptor, or combinations thereof, is administered in an amount of between 0.1 mg/kg and 10 mg/kg body weight of the patient.

3. The method of claim 1 wherein the amount is effective to reduce or prevent vascular remodeling in the patient relative to a control subject.

4. The method of claim 1 wherein the amount is effective to reduce or prevent smooth muscle cell activation and proliferation in the patient relative to a control subject.

5. The method of claim 1 wherein the one or more inhibitors of NAMPT, inhibitors of a NAMPT receptor, or combinations thereof are antibodies, antibody fragments thereof, or proteins having the binding specificity thereof.

6. The method of claim 5, wherein the inhibitor is an F(Ab) fragment of an antibody that binds to NAMPT, or to a NAMPT ligand.

7. The method of claim 5, wherein the inhibitor of NAMPT is a divalent F(Ab)2' fragment of an antibody that binds to NAMPT, or to a NAMPT ligand.

8. The method of claim 5, wherein the antibodies, antibody fragments, or proteins having the binding specificity of an anti-NAMPT antibody prevent or reduce interaction between NAMPT and one or more receptors of NAMPT.

9. The method of claim 8, wherein the antibodies, antibody fragments, or proteins having the binding specificity of an anti-NAMPT antibody prevent or reduce interaction between NAMPT and TLR4 or inhibit enzymatic activity.

10. The method of claim 5 comprising administering by intravenous infusion between about 10 mg and about 400 mg, inclusive, of antibody.

11. The method of claim 1 wherein one or more inhibitors of NAMPT, or inhibitors of TLR4, or combinations thereof is a functional nucleic acid selected from the group consisting of an antisense molecule, siRNA, miRNA, aptamers, ribozymes, triplex forming molecules, RNAi, and external guide sequences.

12. The method of claim 11 wherein the one or more functional nucleic acids are expressed from an expression vector.

13. The method of claim 1 wherein the one or more inhibitors of NAMPT is a small molecule.

14. The method of claim 12 wherein the small molecule is selected from the group consisting of FK-866, MS-1-82, Rari049, and Al-pii135.

15. The method of claim 13 comprising administering between about 0.1 mg/kg and 3.5 mg/kg body weight of the patient, inclusive.

16. The method of claim 15 comprising administering Rari049 in an amount of about 2.5 mg/kg body weight of the patient.

17. The method of claim 1 further comprising administering the inhibitor in a delivery vehicle selected from the group consisting of nanoparticles, microparticles, micelles, emulsions, synthetic lipoprotein particles, liposomes, carbon nanotubes, gels, or coatings.

18. The method of claim 1 further comprising one or more additional therapeutic agents selected from the group consisting of other anti-neointima agents, chemotherapeutic agents, steroidal and non-steroidal anti-inflammatories, conventional immunotherapeutic agents, immune-suppressants, cytokines, chemokines, and growth factors.

19. The method of claim 1, wherein the inhibitor is a small molecule administered orally, and wherein the administration is repeated daily or weekly.

20. The method of claim 1, wherein the inhibitor is administered via intravenous infusion over the course of one hour.

21. The method of claim 1, wherein the administration is repeated once per month, or less frequently.

22. The method of claim 21, further comprising administering one or more additional active agents to the patient.

* * * * *

SEQUENCE LISTING

```
<160> NUMBER OF SEQ ID NOS: 5

<210> SEQ ID NO 1
<211> LENGTH: 1476
<212> TYPE: DNA
<213> ORGANISM: Homo sapiens

<400> SEQUENCE: 1
atgaatcctg cggcagaagc cgagttcaac atcctcctgg ccaccgactc ctacaaggtt      60
actcactata aacaatatcc acccaacaca agcaaagttt attcctactt tgaatgccgt     120
gaaaagaaga cagaaaactc caaattaagg aaggtgaaat atgaggaaac agtattttat     180
gggttgcagt acattcttaa taagtactta aaaggtaaag tagtaaccaa agagaaaatc     240
caggaagcca aagatgtcta caaagaacat ttccaagatg atgtctttaa tgaaaaggga     300
tggaactaca ttcttgagaa gtatgatggg catcttccaa tagaaataaa agctgttcct     360
gagggctttg tcattcccag aggaaatgtt ctcttcacgg tggaaaacac agatccagag     420
tgttactggc ttacaaattg gattgagact attcttgttc agtcctggta tccaatcaca     480
gtggccacaa attctagaga gcagaagaaa atattggcca aatatttgtt agaaacttct     540
ggtaacttag atggtctgga atacaagtta catgattttg ctacagagg agtctcttcc      600 caagagactg ctggcatagg agcatctgct cacttggtta acttcaaagg aacagataca     660
gtagcaggac ttgctctaat taaaaaatat tatggaacga aagatcctgt tccaggctat     720
tctgttccag cagcagaaca cagtaccata acagcttggg ggaaagacca tgaaaaagat     780
gcttttgaac atattgtaac acagttttca tcagtgcctg tatctgtggt cagcgatagc     840
tatgacattt ataatgcgtg tgagaaaata tggggtgaag atctaagaca tttaatagta     900
tcgagaagta cacaggcacc actaataatc agacctgatt ctggaaaccc tcttgacact     960
gtgttaaagg ttttggagat tttaggtaag aagtttcctg ttactgagaa ctcaaagggt    1020
tacaagttgc tgccacctta tcttagagtt attcaagggg atggagtaga tattaatacc    1080
ttacaagaga ttgtagaagg catgaaacaa aaaatgtgga gtattgaaaa tattgccttc    1140
ggttctggtg gaggtttgct acagaagttg acaagagatc tcttgaattg ttccttcaag    1200
tgtagctatg ttgtaactaa tggccttggg attaacgtct tcaaggaccc agttgctgat    1260
cccaacaaaa ggtccaaaaa gggccgatta tctttacata ggacgccagc agggaatttt    1320
gttacactgg aggaaggaaa aggagacctt gaggaatatg gtcaggatct tctccatact    1380
gtcttcaaga atggcaaggt gacaaaaagc tattcatttg atgaaataag aaaaaatgca    1440
cagctgaata ttgaactgga agcagcacat cattag                              1476

<210> SEQ ID NO 2
<211> LENGTH: 491
<212> TYPE: PRT
<213> ORGANISM: Homo sapiens

<400> SEQUENCE: 2
```

-continued

```
Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
            35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
            115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
            165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
    195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
            245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
    275                 280                 285

Lys Ile Trp Gly Glu Asp Leu Arg His Leu Ile Val Ser Arg Ser Thr
            290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
            325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
    355                 360                 365

Lys Gln Lys Met Trp Ser Ile Glu Asn Ile Ala Phe Gly Ser Gly Gly
    370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
            405                 410                 415

Pro Val Ala Asp Pro Asn Lys Arg Ser Lys Lys Gly Arg Leu Ser Leu
```

```
            420             425             430
His Arg Thr Pro Ala Gly Asn Phe Val Thr Leu Glu Glu Gly Lys Gly
                435                 440                 445

Asp Leu Glu Glu Tyr Gly Gln Asp Leu Leu His Thr Val Phe Lys Asn
    450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490

<210> SEQ ID NO 3
<211> LENGTH: 2520
<212> TYPE: DNA
<213> ORGANISM: Homo sapiens

<400> SEQUENCE: 3
```

| | | | | | |
|---|---|---|---|---|---|
| atgatgtctg | cctcgcgcct | ggctgggact | ctgatcccag | ccatggcctt | cctctcctgc | 60 |
| gtgagaccag | aaagctggga | gccctgcgtg | gaggtggttc | ctaatattac | ttatcaatgc | 120 |
| atggagctga | atttctacaa | aatccccgac | aacctcccct | tctcaaccaa | gaacctggac | 180 |
| ctgagcttta | atccctgag | gcatttaggc | agctatagct | tcttcagttt | cccagaactg | 240 |
| caggtgctgg | atttatccag | gtgtgaaatc | cagacaattg | aagatggggc | atatcagagc | 300 |
| ctaagccacc | tctctacctt | aatattgaca | ggaaacccca | tccagagttt | agccctggga | 360 |
| gccttttctg | gactatcaag | tttacagaag | ctggtggctg | tggagacaaa | tctagcatct | 420 |
| ctagagaact | tccccattgg | acatctcaaa | actttgaaag | aacttaatgt | ggctcacaat | 480 |
| cttatccaat | ctttcaaatt | acctgagtat | ttttctaatc | tgaccaatct | agagcacttg | 540 |
| gacctttcca | gcaacaagat | tcaaagtatt | tattgcacag | acttgcgggt | tctacatcaa | 600 |
| atgcccctac | tcaatctctc | tttagacctg | tccctgaacc | ctatgaactt | atccaacca | 660 |
| ggtgcattta | agaaaattag | gcttcataag | ctgactttaa | gaaataattt | tgatagttta | 720 |
| aatgtaatga | aaacttgtat | tcaaggtctg | gctggtttag | aagtccatcg | tttggttctg | 780 |
| ggagaattta | gaaatgaagg | aaacttggaa | aagtttgaca | atctgctct | agagggcctg | 840 |
| tgcaatttga | ccattgaaga | attccgatta | gcatacttag | actactacct | cgatgatatt | 900 |
| attgacttat | ttaattgttt | gacaaatgtt | tcttcatttt | ccctggtgag | tgtgactatt | 960 |
| gaaagggtaa | aagacttttc | ttataatttc | ggatggcaac | atttagaatt | agttaactgt | 1020 |
| aaatttggac | agtttcccac | attgaaactc | aaatctctca | aaaggcttac | tttcacttcc | 1080 |
| aacaaaggtg | ggaatgcttt | ttcagaagtt | gatctaccaa | gccttgagtt | tctagatctc | 1140 |
| agtgaaaatg | gcttgagttt | caaaggttgc | tgttctcaaa | gtgattttgg | gacaaccagc | 1200 |
| ctaaagtatt | tagatctgag | cttcaatggt | gttattacca | tgagttcaaa | cttcttgggc | 1260 |
| ttagaacaac | tagaacatct | ggatttccag | cattccaatt | tgaaacaaat | gagtgagttt | 1320 |
| tcagtattcc | tatcactcag | aaacctcatt | taccttgaca | tttctcatac | tcacaccaga | 1380 |
| gttgctttca | atggcatctt | caatggcttg | tccagtctcg | aagtcttgaa | aatggctggc | 1440 |
| aattcttttc | caggaaaactt | ccttccagat | atcttcacag | agctgagaaa | cttgaccttc | 1500 |
| ctggacctct | ctcagtgtca | actggagcag | ttgtctccaa | cagcatttaa | ctcactctcc | 1560 |
| agtcttcagg | tactaaatat | gagccacaac | aacttctttt | cattggatac | gtttccttat | 1620 |
| aagtgtctga | actccctcca | ggttcttgat | tacagtctca | atcacataat | gacttccaaa | 1680 |
| aaacaggaac | tacagcattt | tccaagtagt | ctagctttct | taaatcttac | tcagaatgac | 1740 |

```
tttgcttgta cttgtgaaca ccagagtttc ctgcaatgga tcaaggacca gaggcagctc  1800
ttggtggaag ttgaacgaat ggaatgtgca acaccttcag ataagcaggg catgcctgtg  1860
ctgagtttga atatcacctg tcagatgaat aagaccatca ttggtgtgtc ggtcctcagt  1920
gtgcttgtag tatctgttgt agcagttctg gtctataagt tctatttca cctgatgctt  1980 cttgctggct gcataaagta tggtagaggt gaaaacatct atgatgcctt tgttatctac  2040
tcaagccagg atgaggactg ggtaaggaat gagctagtaa agaatttaga agaaggggtg  2100
cctccatttc agctctgcct tcactacaga gactttattc ccggtgtggc cattgctgcc  2160
aacatcatcc atgaaggttt ccataaaagc gaaaggtga ttgttgtggt gtcccagcac  2220
ttcatccaga gccgctggtg tatctttgaa tatgagattg ctcagacctg cagtttctg  2280 agcagtcgtg ctggtatcat cttcattgtc ctgcagaagg tggagaagac cctgctcagg  2340
cagcaggtgg agctgtaccg ccttctcagc aggaacactt acctggagtg ggaggacagt  2400
gtcctggggc ggcacatctt ctggagacga ctcagaaaag ccctgctgga tggtaaatca  2460
tggaatccag aaggaacagt gggtacagga tgcaattggc aggaagcaac atctatctga  2520
```

```
<210> SEQ ID NO 4
<211> LENGTH: 839
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|
| Met | Met | Ser | Ala | Ser | Arg | Leu | Ala | Gly | Thr | Leu | Ile | Pro | Ala | Met | Ala |
| 1 | | | | 5 | | | | | 10 | | | | | 15 | |
| Phe | Leu | Ser | Cys | Val | Arg | Pro | Glu | Ser | Trp | Glu | Pro | Cys | Val | Glu | Val |
| | | | 20 | | | | | 25 | | | | | 30 | | |
| Val | Pro | Asn | Ile | Thr | Tyr | Gln | Cys | Met | Glu | Leu | Asn | Phe | Tyr | Lys | Ile |
| | | | 35 | | | | | 40 | | | | | 45 | | |
| Pro | Asp | Asn | Leu | Pro | Phe | Ser | Thr | Lys | Asn | Leu | Asp | Leu | Ser | Phe | Asn |
| | 50 | | | | | 55 | | | | | 60 | | | | |
| Pro | Leu | Arg | His | Leu | Gly | Ser | Tyr | Ser | Phe | Phe | Ser | Phe | Pro | Glu | Leu |
| 65 | | | | | 70 | | | | | 75 | | | | | 80 |
| Gln | Val | Leu | Asp | Leu | Ser | Arg | Cys | Glu | Ile | Gln | Thr | Ile | Glu | Asp | Gly |
| | | | | 85 | | | | | 90 | | | | | 95 | |
| Ala | Tyr | Gln | Ser | Leu | Ser | His | Leu | Ser | Thr | Leu | Ile | Leu | Thr | Gly | Asn |
| | | | 100 | | | | | 105 | | | | | 110 | | |
| Pro | Ile | Gln | Ser | Leu | Ala | Leu | Gly | Ala | Phe | Ser | Gly | Leu | Ser | Ser | Leu |
| | | | 115 | | | | | 120 | | | | | 125 | | |
| Gln | Lys | Leu | Val | Ala | Val | Glu | Thr | Asn | Leu | Ala | Ser | Leu | Glu | Asn | Phe |
| | 130 | | | | | 135 | | | | | 140 | | | | |
| Pro | Ile | Gly | His | Leu | Lys | Thr | Leu | Lys | Glu | Leu | Asn | Val | Ala | His | Asn |
| 145 | | | | | 150 | | | | | 155 | | | | | 160 |
| Leu | Ile | Gln | Ser | Phe | Lys | Leu | Pro | Glu | Tyr | Phe | Ser | Asn | Leu | Thr | Asn |
| | | | | 165 | | | | | 170 | | | | | 175 | |
| Leu | Glu | His | Leu | Asp | Leu | Ser | Ser | Asn | Lys | Ile | Gln | Ser | Ile | Tyr | Cys |
| | | | 180 | | | | | 185 | | | | | 190 | | |
| Thr | Asp | Leu | Arg | Val | Leu | His | Gln | Met | Pro | Leu | Leu | Asn | Leu | Ser | Leu |
| | | | 195 | | | | | 200 | | | | | 205 | | |
| Asp | Leu | Ser | Leu | Asn | Pro | Met | Asn | Phe | Ile | Gln | Pro | Gly | Ala | Phe | Lys |
| | 210 | | | | | 215 | | | | | 220 | | | | |
| Glu | Ile | Arg | Leu | His | Lys | Leu | Thr | Leu | Arg | Asn | Asn | Phe | Asp | Ser | Leu |
| 225 | | | | | 230 | | | | | 235 | | | | | 240 |

-continued

Asn Val Met Lys Thr Cys Ile Gln Gly Leu Ala Gly Leu Glu Val His
            245             250             255

Arg Leu Val Leu Gly Glu Phe Arg Asn Glu Gly Asn Leu Glu Lys Phe
        260             265             270

Asp Lys Ser Ala Leu Glu Gly Leu Cys Asn Leu Thr Ile Glu Glu Phe
        275             280             285

Arg Leu Ala Tyr Leu Asp Tyr Tyr Leu Asp Asp Ile Ile Asp Leu Phe
        290             295             300

Asn Cys Leu Thr Asn Val Ser Ser Phe Ser Leu Val Ser Val Thr Ile
305             310             315             320

Glu Arg Val Lys Asp Phe Ser Tyr Asn Phe Gly Trp Gln His Leu Glu
            325             330             335

Leu Val Asn Cys Lys Phe Gly Gln Phe Pro Thr Leu Lys Leu Lys Ser
            340             345             350

Leu Lys Arg Leu Thr Phe Thr Ser Asn Lys Gly Gly Asn Ala Phe Ser
            355             360             365

Glu Val Asp Leu Pro Ser Leu Glu Phe Leu Asp Leu Ser Arg Asn Gly
        370             375             380

Leu Ser Phe Lys Gly Cys Cys Ser Gln Ser Asp Phe Gly Thr Thr Ser
385             390             395             400

Leu Lys Tyr Leu Asp Leu Ser Phe Asn Gly Val Ile Thr Met Ser Ser
            405             410             415

Asn Phe Leu Gly Leu Glu Gln Leu Glu His Leu Asp Phe Gln His Ser
            420             425             430

Asn Leu Lys Gln Met Ser Glu Phe Ser Val Phe Leu Ser Leu Arg Asn
            435             440             445

Leu Ile Tyr Leu Asp Ile Ser His Thr His Thr Arg Val Ala Phe Asn
450             455             460

Gly Ile Phe Asn Gly Leu Ser Ser Leu Glu Val Leu Lys Met Ala Gly
465             470             475             480

Asn Ser Phe Gln Glu Asn Phe Leu Pro Asp Ile Phe Thr Glu Leu Arg
            485             490             495

Asn Leu Thr Phe Leu Asp Leu Ser Gln Cys Gln Leu Glu Gln Leu Ser
            500             505             510

Pro Thr Ala Phe Asn Ser Leu Ser Ser Leu Gln Val Leu Asn Met Ser
            515             520             525

His Asn Asn Phe Phe Ser Leu Asp Thr Phe Pro Tyr Lys Cys Leu Asn
            530             535             540

Ser Leu Gln Val Leu Asp Tyr Ser Leu Asn His Ile Met Thr Ser Lys
545             550             555             560

Lys Gln Glu Leu Gln His Phe Pro Ser Ser Leu Ala Phe Leu Asn Leu
            565             570             575

Thr Gln Asn Asp Phe Ala Cys Thr Cys Glu His Gln Ser Phe Leu Gln
            580             585             590

Trp Ile Lys Asp Gln Arg Gln Leu Leu Val Glu Val Glu Arg Met Glu
            595             600             605

Cys Ala Thr Pro Ser Asp Lys Gln Gly Met Pro Val Leu Ser Leu Asn
            610             615             620

Ile Thr Cys Gln Met Asn Lys Thr Ile Ile Gly Val Ser Val Leu Ser
625             630             635             640

Val Leu Val Val Ser Val Ala Val Leu Val Tyr Lys Phe Tyr Phe
            645             650             655

```
His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
        690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
                740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
        770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
                820                 825                 830

Trp Gln Glu Ala Thr Ser Ile
        835

<210> SEQ ID NO 5
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 5

Glu Gly Lys Gly Asp Leu Glu Glu Tyr Gly His Asp Leu
1               5                   10
```